(12) United States Patent
Dang et al.

(10) Patent No.: US 7,807,630 B2
(45) Date of Patent: Oct. 5, 2010

(54) TARGETING OF NOTCH3 RECEPTOR FUNCTION FOR CANCER THERAPY

(75) Inventors: Thao P. Dang, Nashville, TN (US); David P. Carbone, Franklin, TN (US); Ray Mernaugh, Franklin, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 12/208,875

(22) Filed: Sep. 11, 2008

(65) Prior Publication Data

US 2009/0092615 A1    Apr. 9, 2009

Related U.S. Application Data

(60) Provisional application No. 60/972,584, filed on Sep. 14, 2007.

(51) Int. Cl.
   *A61K 38/00* (2006.01)
(52) U.S. Cl. .......................................... 514/2
(58) Field of Classification Search ...................... None
   See application file for complete search history.

(56) References Cited

FOREIGN PATENT DOCUMENTS

| WO | WO 98/05775 | | 2/1998 |
|---|---|---|---|
| WO | WO 02/20722 | * | 3/2002 |
| WO | WO 03/042246 | | 5/2003 |
| WO | WO 2005/017096 | * | 2/2005 |
| WO | WO 2006/047878 | * | 5/2006 |
| WO | WO 2008/076960 | | 6/2008 |

OTHER PUBLICATIONS

Peters et al. "Solid-phase synthesis of a fucosylated glycopeptide of human factor IX with a fucose- -( I->O)-serine linkage." J. Chem. Soc. Perkins Trans., 1995, p. 3017-3022.*
Viveros et al. "Characterization of a Novel Human Immunodeficiency Virus Type 1 Neutralizable Epitope within the Immunodominant Region of gp41," Virology, 2000, 270, 135-145.*
Rebay et al. "Specific EGF Repeats of Notch Mediate Interactions with Delta and Serrate: Implications for Notch as a Multifunctional Receptor," Cell, 1991, 67, 687-699.*
Hambleton et al. "Structural and Functional Properties of the Human Notch-1 Ligand Binding Region," Structure, 2004, 12, 2173-2183.*
Ahmad et al., "Involvement of Mash1 in EGF-mediated regulation of differentiation in the vertebrate retina," *Dev. Biol.*, 194:86-98, 1998.
Alves da Costa et al., "Presenilin-directed inhibitors of gamma-secretase trigger caspase 3 activation in presenilin-expressing and presenilin-deficient cells," *J. Neurochem.*, 90:800-806, 2004.
Artavanis-Tsakonas et al., "Notch signaling: cell fate control and signal integration in development.," *Science*, 284:770-776, 1999.
Barry et al., "Constitutive ERK1/2 activation in esophagogastric rib bone marrow micrometastatic cells in MEK-independent," *J. Biol. Chem.*, 276: 15537-15546, 2001.
Beatus and Lendahl, "Notch and neurogenesis," *J. Neurosci. Res.*, 54:125-136, 1998.
Bellavia et al., "Combined expression of pTalpha and Notch3 in T cell leukemia identifies the requirement of preTCR for leukemogenesis," *Proc. Natl. Acad. Sci. USA*, 99:3788-3793, 2002.
Bellavia et al., "Constitutive activation of NF-kappaB and T-cell leukemia/lymphoma in Notch3 transgenic mice," *EMBO J.*, 19:3337-3348, 2000.
Berset et al., "Notch inhibition of RAS signaling through MAP kinase phosphatase LIP-1 during *C. elegans* vulval development," *Science*, 291:1055-1058, 2001.
Brondello et al., "The dual specificity mitogen-activated protein kinase phosphate-1 and -2 are induced by the p42/p44MAPK cascade," *J. Biol. Chem.*, 272:1368-1376, 1997.
Callahan and Egan, "Notch signaling in mammary development and oncogenesis," *J. Mammary Gland Biol. Neoplasia.*, 9:145-163, 2004.
Campos et al., "Determinants of Notch-3 receptor expression and signaling in vascular smooth muscle cells: implications in cell-cycle regulation," *Circ. Res.*, 91:999-1006, 2002.
Curry et al., "Gamma secretase inhibitor blocks Notch activation and induces apoptosis in Kaposi's sarcoma tumor cells," *Oncogene*, 24:6333-6344, 2005.
Dang et al., "Chromosome 19 translocation, overexpression of notch3, and human lung cancer," *Journal of the National Institute*, 92:1355-1357, 2000.
Domenga et al., "Notch3 is required for arterial identity and maturation of vascular smooth muscle cells," *Genes Dev.*, 18:2730-2735, 2004.
Dovey et al., "Functional gamma-secretase inhibitors reduce beta-amyloid peptide levels in brain," *J. Neurochem.*, 76:173-181, 2001.
Ellisen et al., "TAN-1, the human homolog of the *Drosophila* notch gene, is broken by chromosomal translocations in T lymphoblastic neoplasms," *Cell*, 66:649-661, 1991.
Faux et al., "Interactions between fibroblast growth factors and Notch regulate neuronal differentiation," *J. Neurosci.*, 21:5587-5596, 2001.
Fitzgerald et al., "Ras pathway signals are required for notch-mediated oncogenesis," *Oncogene*, 19:4191-4198, 2000.
Haneda et al., "Mitogen-activated protein kinase phosphatase: a negative regulator of the mitogen-activated protein kinase cascade," *Eur. J. Pharmacol.*, 365:1-7, 1999.
Haruki et al., "Dominant-negative notch3 receptor inhibits mitogen-activated protein kinase pathway and the growth of human lung cancers," *Cancer Res.*, 65:3555-3561, 2005.
Hirsch et al., "Evaluation of HER-2/neu gene amplification and protein expression in non-small cell lung carcinomas," *Br. J. Cancer*, 86:1449-1456, 2002.
Hrabe de Angelis et al., "Maintenance of somite borders in mice requires the Delta homologue DII1," *Nature*, 386:717-721, 1997.
Jhappan et al., "Expression of an activated Notch-related int-3 transgene interferes with cell differentiation and induces neoplastic transformation in mammary and salivary glands," *Genes Dev.*, 6:345-355, 1992.

(Continued)

*Primary Examiner*—Christina Bradley
(74) *Attorney, Agent, or Firm*—Fulbright & Jaworski

(57) ABSTRACT

The present invention involves the use of peptides from Notch3, and antibodies that recognize epitopes represented by those peptides, as anti-cancer agents. Methods of combination therapy using standard anti-cancer protocols in conjunction with Notch3 peptides and antibodies also are provided.

21 Claims, 17 Drawing Sheets

OTHER PUBLICATIONS

Konishi et al., "γ-secretase inhibitor prevents notch3 activation and reduces proliferation in human lung cancers," *Cancer Res.*, 67:8051-8057, 2007.

Krebs et al., "Notch signaling is essential for vascular morphogenesis in mice," *Genes Dev.*, 14:1343-1352, 2000.

Lanford et al., "Notch signalling pathway mediates hair cell development in mammalian cochlea," *Nat. Genet.*, 21:289-292, 1999.

Levitan and Greenwald, "Facilitation of lin-12-mediated signalling by sel-12, a *Caenorhabditis elegans* S182 Alzheimer's disease gene," *Nature*, 377:351-354, 1995.

Li et al., "Modulation of notch signaling by antibodies specific for the extracellular negative regulatory region of NOTCH3," *Journal of Biological Chemistry*, 283:8046-8054, 2008.

Linggi et al., "The ErbB-4 s80 intracellular domain is a constitutively active tyrosine kinase," *Oncogene*, 25:160-163, 2006.

Lu et al., "Selection of potential markers for epithelial ovarian cancer with gene expression arrays and recursive descent partition analysis," *Clin. Cancer Res.*, 10:3291-3300, 2004.

Ma et al., "Hematological features and treatment outcome in acute myeloid leukemia with t(8;21)," *Hematol. Oncol.*, 15:93-103, 1997.

Meert et al., "The role of EGF-R expression on patient survival in lung cancer: a systematic review with meta-analysis," *Eur. Respir. J.*, 20:975-981, 2002.

Miyamoto et al., "Notch mediates TGF alpha-induced changes in epithelial differentiation during pancreatic tumorigenesis," *Cancer Cell*, 3:565-576, 2003.

Mumm and Kopan, "Notch signaling: from the outside in," *Dev. Biol.*, 228:151-165, 2000.

Paris et al., "Inhibition of angiogenesis and tumor growth by beta and gamma-secretase inhibitors," *Eur. J. Pharmacol.*, 514:1-15, 2005.

Pear et al., "Exclusive development of T cell neoplasms in mice transplanted with bone marrow expressing activated Notch alleles," *J. Exp. Med.*, 183:2283-2291, 1996.

Pelletier et al., "Gamma-secretase-dependent proteolysis of CD44 promotes neoplastic transformation of rat fibroblastic cells," *Cancer Res.*, 66:3681-3687, 2006.

Purow et al., "Expression of Notch-1 and its ligands, Delta-like-1 and Jagged-1, is critical for glioma cell survival and proliferation," *Cancer Res.*, 65:2353-2363, 2005.

Qin et al., "p53-independent NOXA induction overcomes apoptotic resistance of malignant melanomas," *Mol. Cancer Ther.*, 3:895-902, 2004.

Robey et al., "An activated form of Notch influences the choice between CD4 and CD8 T cell lineages," *Cell*, 87:483-492, 1996.

Rodenhuis et al., "Mutational activation of the K-ras oncogene and the effect of chemotherapy in advanced adenocarcinoma of the lung: a prospective study," *J. Clin. Oncol.*, 15:285-291, 1997.

Rohn et al., "Transduction of Notch2 in feline leukemia virus-induced thymic lymphoma," *J. Virol.*, 70:8071-8080, 1996.

Santagata et al., "JAGGED1 expression is associated with prostate cancer metastasis and recurrence," *Cancer Res.*, 64:6854-6857, 2004.

Shelly et al., "Notch-1 inhibits apoptosis in murine erythroleukemia cells and is necessary for differentiation induced by hybrid polar compounds," *J. Cell Biochem.*, 73:164-175, 1999.

Sivaraman et al., "Hyperexpression of mitogen-activated protein kinase in human breast cancer.," *J. Clin. Invest.*, 99:1478-1483, 1997.

Small et al., "Notch activation suppresses fibroblast growth factor-dependent cellular transformation," *J. Biol. Chem.*, 278:16405-16413, 2003.

Sundaram, "The love-hate relationship between Ras and Notch," *Genes Dev.*, 19:1825-1839, 2005.

Sweeney et al., "Notch 1 and 3 receptor signaling modulates vascular smooth muscle cell growth, apoptosis, and migration via a CBF-1/RBP-Jk dependent pathway," *FASEB J.*, 18:1-29, 2004.

Traverse et al., "Sustained activation of the mitogen-activated protein (MAP) kinase cascade may be required for differentiation of PC12 cells. Comparison of the effects of nerve growth factor and epidermal growth factor," *Biochem. J.*, 288(Pt. 2):351-355, 1992.

Wang et al., "Coordinate Notch3-hairy-related transcription factor pathway regulation in response to arterial injury. Mediator role of platelet-derived growth factor and ERK," *J. Biol. Chem.*, 277:23165-23171, 2002.

Wang et al., "Overexpression of mitogen-activated protein kinase phosphatases MKP1, MKP2 in human breast cancer," *Cancer Letters*, xx:229-237, 2002.

Weng et al., "Activating mutations of NOTCH1 in human T cell acute lymphoblastic leukemia," *Science*, 306:269-271, 2004.

Williams et al., "Up-regulation of the Notch ligand Delta-like 4 inhibits VEGF-induced endothelial cell function," *Blood*, 107:931-939, 2006.

Xue et al., "Embryonic lethality and vascular defects in mice lacking the Notch ligand Jagged1," *Hum. Mol. Genet.*, 8:723-730, 1999.

Yoo et al., "Crosstalk between the EGFR and LIN-12/Notch pathways in *C. elegans* vulval development," *Science*, 303:663-666, 2004.

Zeng et al., "Crosstalk between tumor and endothelial cells promotes tumor angiogenesis by MAPK activation of Notch signaling," *Cancer Cell*, 8:12-23, 2005.

Lin et al., "Targeting specific regions of the Notch3 ligand-binding domain induces apoptosis and inhibits tumor growth in lung cancer," *Cancer Res.*, 70:632-8, 2010.

* cited by examiner

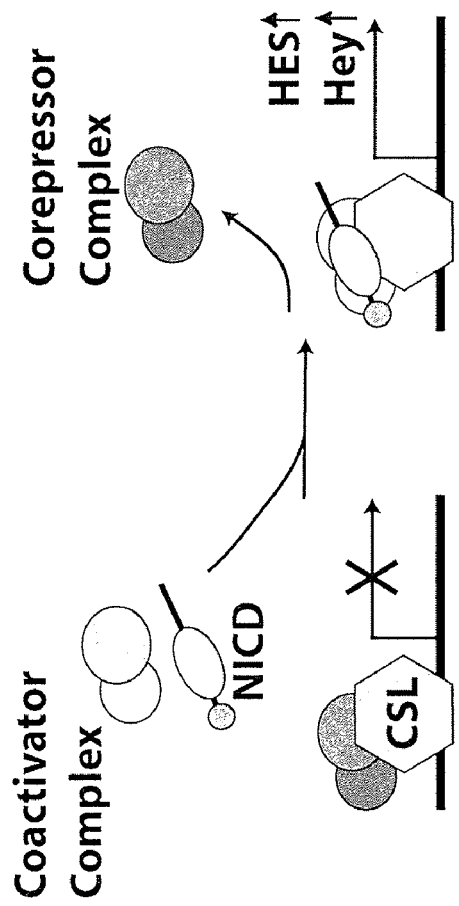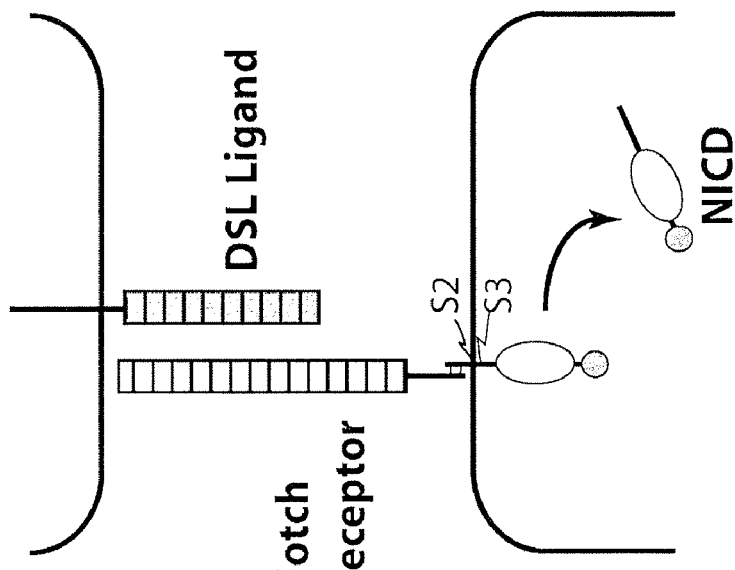
FIG. 1A-B

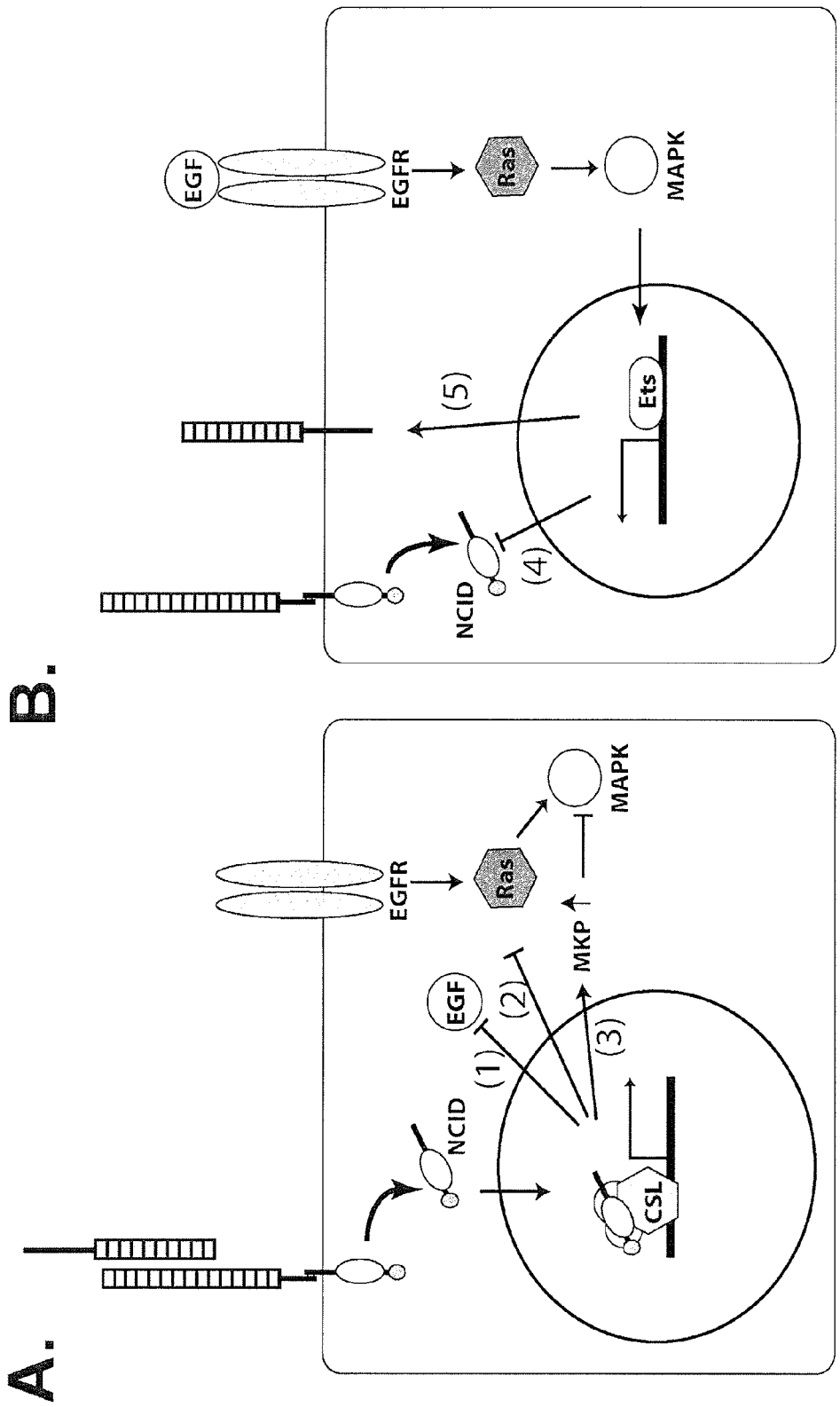
FIG. 2A-B

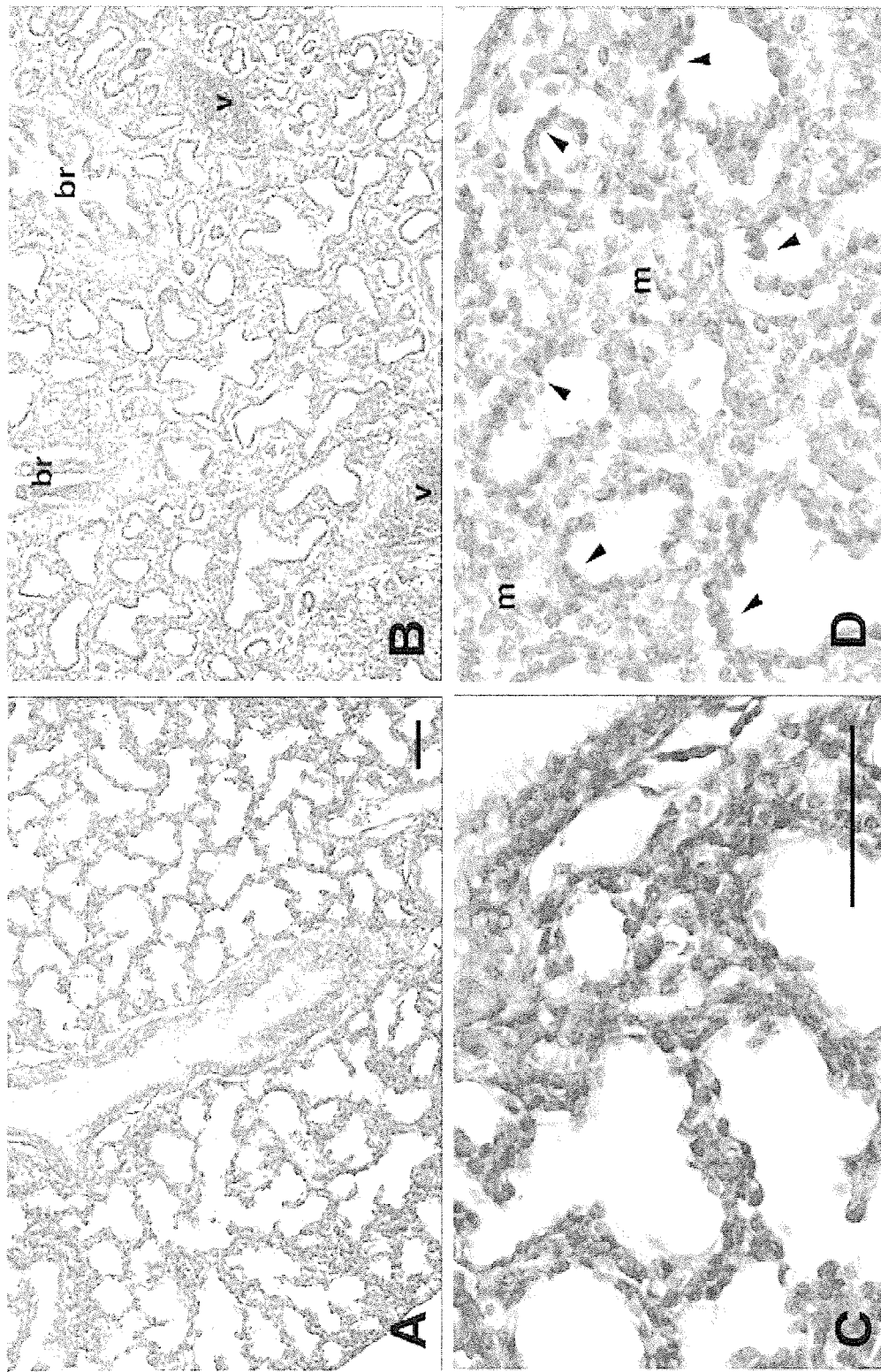
FIG. 4A-D

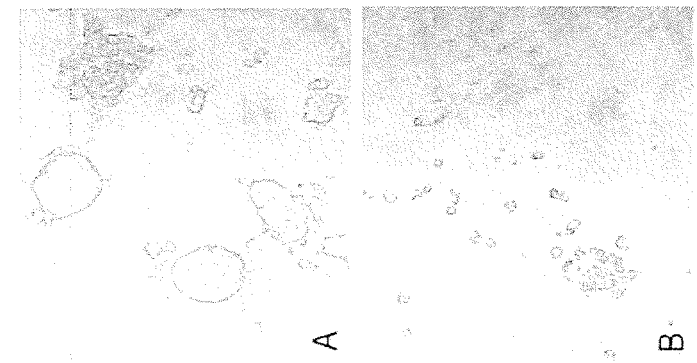
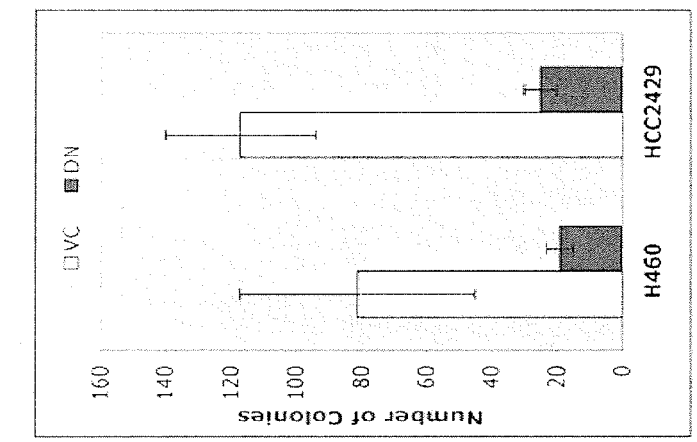
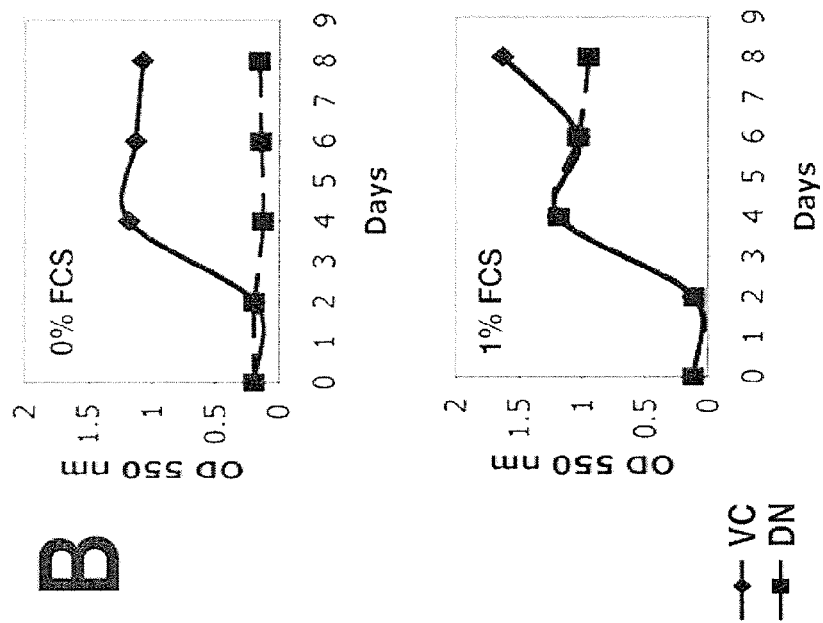
FIG. 5A-B

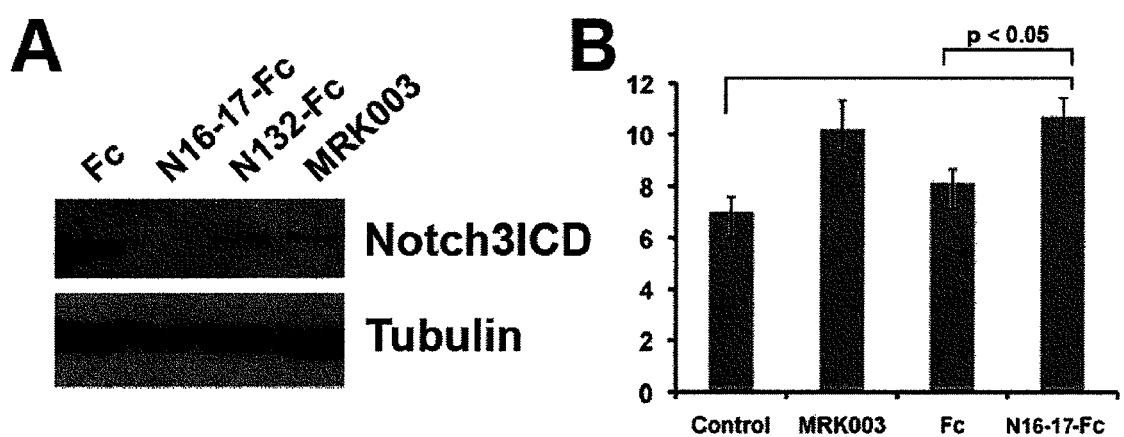
FIG. 17A-B

TARGETING OF NOTCH3 RECEPTOR FUNCTION FOR CANCER THERAPY

This application claims benefit of priority to U.S. Prov. Appln. Ser. No. 60/972,584, filed Sep. 14, 2007, the entire contents of which are hereby incorporated by reference.

This invention was made with government support under grant no. 2P50 CA090949 awarded by the National Cancer Institute. The government has certain rights in the invention.

BACKGROUND OF THE INVENTION

I. Field of the Invention

The present invention relates to the fields of oncology and molecular biology. More particular the invention relates to the targeting of the Notch3 receptor.

II. Related Art

Lung cancer is the most common cause of cancer-related deaths in the United States. The cure rate for patients with lung cancer remains low—15%—and has not changed significantly during the past 30 years (Jermal et al., 2005). A better understanding of the signaling pathways important in driving and maintaining the malignant state allows the identification of new therapeutic targets and is thus imperative for continued progress in the treatment of these patients. Genes involved in cell fate determination often contribute to tumorigenesis when they are aberrantly expressed. The family of Notch receptors is one such family where there are now strong data linking it to cancer pathogenesis.

All four members of the Notch receptor family are known to be dysregulated in the majority of human cancers. The inventors were the first to link dysregulation of the Notch3 pathway to human lung cancer (Dang et al., 2000). They demonstrated that Notch3 is highly expressed in 40% of all resected lung cancers and that, in the developing lung, constitutive activation of Notch3 results in inhibition of terminal differentiation. Furthermore, they showed that inhibiting this pathway in human lung tumors results in the loss of the malignant phenotype in vitro and tumor inhibition in xenograft models. This anti-tumor effect is enhanced in the presence of low serum and in combination with an EGFr tyrosine kinase inhibitor. Taken together, these data support an important role for Notch3 and its interaction with the EGF and Ras pathways in lung cancer. However, methods for therapeutic intervention in Notch3 related cancers has not yet been reported.

SUMMARY OF THE INVENTION

Thus, in accordance with the present invention, there is provided an isolated and purified peptide of no more than about 50 residues and comprising the sequence of CFNTLGGHS (SEQ ID NO:3), CVCVNGWTGES (SEQ ID NO:4), CATAV (SEQ ID NO:5), CFHGAT (SEQ ID NO:6), CVSNP (SEQ ID NO:7) or CLNGGS (SEQ ID NO:8). More particular peptides include the sequences CFNTLGGHSCVCVNGWTGESCSQNIDDCATAVCFHGAT (SEQ ID NO:9) or CTNLAGSFSCTCHGGYTGPSCDQDINDCDPNPCLNGGS (SEQ ID NO:10). The peptide may be no more than about 25 residues, or no more than about 20 residues, or no more than about 15 residues. The peptide may consist of the sequence of CFNTLGGHS (SEQ ID NO:3), CVCVNGWTGES (SEQ ID NO:4), CATAV (SEQ ID NO:5), CFHGAT (SEQ ID NO:6), CVSNP (SEQ ID NO:7), CLNGGS (SEQ ID NO:8), CFNTLGGHSCVCVNGWTGESCSQNIDDCATAVCFHGAT (SEQ ID NO:9) or CTNLAGSFSCTCHGGYTGPSCDQDINDCDPNPCLNGGS (SEQ ID NO:10). The peptide may further be comprised in a pharmaceutically acceptable diluent, buffer or excipient.

In another embodiment, there is provided a method of inhibiting Notch3 receptor signaling comprising contacting a cell expressing Notch3 with a peptide of no more than about 50 residues and comprising the sequence of CFNTLGGHS (SEQ ID NO:3), CVCVNGWTGES (SEQ ID NO:4), CATAV (SEQ ID NO:5), CFHGAT (SEQ ID NO:6), CVSNP (SEQ ID NO:7) or CLNGGS (SEQ ID NO:8). The cell may be a cancer cell, such as a lung cancer cell and/or an adenocarcinoma. More particular peptides include the sequences CFNTLGGHSCVCVNGWTGESCSQNIDDCATAVCFHGAT (SEQ ID NO:9) or CTNLAGSFSCTCHGGYTGPSCDQDINDCDPNPCLNGGS (SEQ ID NO:10). The peptide may be no more than about 25 residues, or no more than about 20 residues, or no more than about 15 residues. The peptide may consist of the sequence of CFNTLGGHS (SEQ ID NO:3), CVCVNGWTGES (SEQ ID NO:4), CATAV (SEQ ID NO:5), CFHGAT (SEQ ID NO:6), CVSNP (SEQ ID NO:7), CLNGGS (SEQ ID NO:8), CFNTLGGHSCVCVNGWTGESCSQNIDDCATAVCFHGAT (SEQ ID NO:9) or CTNLAGSFSCTCHGGYTGPSCDQDINDCDPNPCLNGGS (SEQ ID NO:10). The method may further comprise contacting the cell with two or more peptides comprising sequences of at least two of CFNTLGGHS (SEQ ID NO:3), CVCVNGWTGES (SEQ ID NO:4), CATAV (SEQ ID NO:5), CFHGAT (SEQ ID NO:6), CVSNP (SEQ ID NO:7), CLNGGS (SEQ ID NO:8), CFNTLGGHSCVCVNGWTGESCSQNIDDCATAVCFHGAT (SEQ ID NO:9) or CTNLAGSFSCTCHGGYTGPSCDQDINDCDPNPCLNGGS (SEQ ID NO:10). The method may also further comprises contacting the cancer cell with a second agent that inhibits cancer cell growth, differentiation, metastasis or drug resistance.

In yet another embodiment, there is provided a method of treating a subject having a Notch3-expressing cancer comprising administering to said subject a peptide of no more than about 50 residues and comprising the sequence of CFNTLGGHS (SEQ ID NO:3), CVCVNGWTGES (SEQ ID NO:4), CATAV (SEQ ID NO:5), CFHGAT (SEQ ID NO:6), CVSNP (SEQ ID NO:7) or CLNGGS (SEQ ID NO:8). The subject may a human. The cancer cell may be a lung cancer cell and/or an adenocarcinoma. More particular peptides include the sequences CFNTLGGHSCVCVNGWTGESCSQNIDDCATAVCFHGAT (SEQ ID NO:9) or CTNLAGSFSCTCHGGYTGPSCDQDINDCDPNPCLNGGS (SEQ ID NO:10). The peptide may be no more than about 25 residues, or no more than about 20 residues, or no more than about 15 residues. The peptide may consist of the sequence of CFNTLGGHS (SEQ ID NO:3), CVCVNGWTGES (SEQ ID NO:4), CATAV (SEQ ID NO:5), CFHGAT (SEQ ID NO:6), CVSNP (SEQ ID NO:7), CLNGGS (SEQ ID NO:8), CFNTLGGHSCVCVNGWTGESCSQNIDDCATAVCFHGAT (SEQ ID NO:9) or CTNLAGSFSCTCHGGYTGPSCDQDINDCDPNPCLNGGS (SEQ ID NO:10). The method may further comprise contacting the cell with two or more peptides comprising sequences of at least two of CFNTLGGHS (SEQ ID NO:3), CVCVNGWTGES (SEQ ID NO:4), CATAV (SEQ ID NO:5), CFHGAT (SEQ ID NO:6), CVSNP (SEQ ID NO:7), CLNGGS (SEQ ID NO:8), CFNTLGGHSCVCVNGWTGESCSQNIDDCATAVCFHGAT (SEQ ID NO:9) or CTNLAGSFSCTCHGGYTGPSCDQDINDCDPNPCLNGGS (SEQ ID NO:10). The method may also further comprises contacting the cancer cell with a second agent that inhibits cancer cell growth, differentiation, metastasis or drug resistance.

Also provided are an isolated and purified antibody that binds to an epitope comprising the sequence of CFNTLGGHS (SEQ ID NO:3), CVCVNGWTGES (SEQ ID NO:4), CATAV (SEQ ID NO:5), CFHGAT (SEQ ID NO:6), CVSNP (SEQ ID NO:7) or CLNGGS (SEQ ID NO:8), as well as methods of using such antibodies to inhibit Notch3 receptor signaling in a cell expressing Notch3.

In still another embodiment, there is provided a method of treating a subject having a Notch3-expressing cancer comprising administering to said subject an antibody that binds to an epitope comprising the sequence of CFNTLGGHS (SEQ ID NO:3), CVCVNGWTGES (SEQ ID NO:4), CATAV (SEQ ID NO:5), CFHGAT (SEQ ID NO:6), CVSNP (SEQ ID NO:7) or CLNGGS (SEQ ID NO:8).

Yet another embodiment comprises a pharmaceutical formulation comprising two or more of CFNTLGGHS (SEQ ID NO:3), CVCVNGWTGES (SEQ ID NO:4), CATAV (SEQ ID NO:5), CFHGAT (SEQ ID NO:6), CVSNP (SEQ ID NO:7), CLNGGS (SEQ ID NO:8), CFNTLGGHSCVCVNGWT-GESCSQNIDDCATAVCFHGAT (SEQ ID NO:9) or CTNLAGSFSCTCHGGYTGPSCDQDIND-CDPNPCLNGGS (SEQ ID NO:10) including three, four, five, six, seven or all of CFNTLGGHS (SEQ ID NO:3), CVCVNGWTGES (SEQ ID NO:4), CATAV (SEQ ID NO:5), CFHGAT (SEQ ID NO:6), CVSNP (SEQ ID NO:7), CLNGGS (SEQ ID NO:8), CFNTLGGHSCVCVNGWT-GESCSQNIDDCATAVCFHGAT (SEQ ID NO:9) or CTNLAGSFSCTCHGGYTGPSCDQDIND-CDPNPCLNGGS (SEQ ID NO:10).

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIGS. 1A-B. Diagram demonstrates the major steps of the canonical Notch pathway. (FIG. 1A) Binding of a DSL ligand triggers proteolysis (S2 and S3) of the Notch receptor and releases the C-terminal NICD fragment. (FIG. 1B) NICD translocates to the nucleus, recruits coactivators, and binds to CSL factors to promote target gene transcription. In the absence of NICD, the CSL factor associates with the corepressor complex and inhibits target gene transcription.

FIGS. 2A-B. Proposed mechanisms of antagonistic and cooperative interactions between Ras and Notch pathways. (FIG. 2A) Notch antagonizes Ras signaling by preventing expression of active EGF (1). Notch activation can also directly inhibit Ras activity (2) and induce expression MAPK inhibitors (3). (FIG. 2B) Ras activation in turn can induce expression of Notch inhibitors (4). Paradoxically, Ras activation has also been shown to induce DSL ligand expression (5). These observation further support the hypothesis that Notch activation is highly context dependent. However, in a majority of cancers, Notch and ras appear to be cooperative. Adapted from Sundaram (2005).

FIGS. 5A-B. Notch inhibition inhibits the tumor phenotype. (FIG. 5A) Inhibition of the Notch3 signaling pathway markedly reduces the size of the colonies formed in soft agar (panel B), compared with vector controls (panel A) in HCC2429 and H460. (FIG. 5B) In serum-starved conditions, the growth of the DN transfectant is severely inhibited in comparison with that of VC. However, with the addition of exogenous growth factors, the growth rate is equal to that of VC.

(FIG. 7A) GSI inhibits HCC2429 cells in a serum-dependent manner. HCC2429 cells are sensitive to GSI, and the sensitivity increases in low serum, similarly to that observed with clones expressing the DN construct. Tumor cells treated with DMSO alone had no change in cell viability. (FIG. 7B) Inhibition of S3 proteolytic processing results in the decrease of Notch3 intracellular domain (N3ICD) and accumulation of S2 product (N3ΔE) after 3 hours. (FIG. 7C) In this experiment, HCC2429 was stably transfected with plasmid vector expressing Notch3 siRNA. Control C is the parental HCC2429, whereas siRNA-C clones 5, 6, 8 expressed high level of HCC2429 and siRNA-N3 clones 12, 15, 17 and 20 expressed significantly lower level of Notch3 (FIG. 7D). Loss of Notch3 results in no loss in cell survival when treated with MRK003.

(FIG. 8A) Xenografts injected with HCC2429 were treated with MRK003 once the tumors became palpable. After 2 weeks of treatment, the inventors observed about a 50% reduction in tumor size. (FIG. 8B) Loss of activated Notch3 (N3ICD) can be seen in tumor treated with MRK003. Histological examination of resected tumors from xenografts at the end of treatment. Marked necrosis can be seen in the MRK003 treated animal (FIG. 8D) as compare to control (FIG. 8C).

(FIG. 9A) After 72 hours of exogenous growth factor deprivation, cell lines transfected with DN show a higher percentage of apoptosis as measured by Apo-BrdU analysis. (FIG. 9B) Expression levels of phospho-Akt protein decrease in the Notch3-overexpressing cell line HCC2429 when it is stably transfected with the DN construct, particularly with serum starvation. (FIG. 9C) Transfection with Notch3 SiRNA resulted in loss of Bcl-xL expression and induction of apoptotic product PARP.

(FIG. 10A) Inhibition of Notch3 signaling in HCC2429 downregulates phospho-p44/42 (ERK?) under serum-starved conditions and after induction with 10% FCS. (FIG. 10B) When the immortalized lung epithelial cell line BEAS-2B was transfected with the DA construct, the inventors observed higher levels of phospho-p44/p42 under serum-starved conditions as well as after serum induction. (FIG. 10C) One mechanism of MAPK modulation includes transcriptional regulation of MKP1 in HCC2429. The DN clones demonstrate significantly higher transcriptional level of MKP1 under serum-starved conditions and at 30 minutes and 1 hour after serum induction, when compared with VC (*).

(FIG. 11A) In HCC2429, inhibition of the Notch3 pathway increases sensitivity to AG1478 nearly 40-fold. In H460, a cell line that is markedly resistant to AG1478 ($IC_{50}$=23.8 µM) when compared to HCC2429 ($IC_{50}$=8.3 µM), inhibition of Notch3 also increases sensitivity to the inhibitor. (FIG. 11B) A similar observation is made in H460 when the inventors combine AG1478 with L-685,458, a γ-secretase inhibitor, further supporting the hypothesis that EGF cooperates with the Notch pathway in oncogenesis.

(FIG. 12A) Photographs showing that MRK003 not only decreases colony formation, but also enhances the effect of AG1478 on growth. (FIG. 12B) Graph depicts the quantitative decrease in colony formation.

(FIG. 14A) HCC2429 was treated with Notch3 peptides N16, N17, N102, N103, N132. Induction of apoptosis by peptides is observed as compared to control. MRK003-treated cell is used as positive control. After treatment, cells were labeled with annexin V and detected using flow cytometry. (FIG. 14B) Treatment with peptides also reduced transcription of Notch3-dependent gene Hey1 as determined by real-time RT-PCR. Of note, N17 peptide both demonstrates highest apoptotic activity and best reduction in Hey1 transcription. MRK003-treated cells were used as positive control. Sequences N16: CFNTLGGHS, N17: CVCVNGWTGES, N102: CATAV, N103: CFHGAT, N132: CLNGGS.

FIGS. 17A-B. Recombinant Fc-fusion Notch3 proteins inhibit Notch3 activation and induces apoptosis in vitro. (FIG. 17A) Fc-fusion protein comprised for N16-17 and N132 sequences inhibits Notch3 activation. HCC2429 was treated with purified Fc-fusion protein 10 µg/ml for 24 hrs. (FIG. 17B) Purified recombinant N16-17-Fc protein induces apoptosis as compared to control and Fc control after 40 hrs treatment. Apoptosis was determined by percentage of annexin V positive cells. Sequences N16: CFNTLGGHS, N17: CVCVNGWTGES, N132: CLNGGS.

DETAILED DESCRIPTION OF THE PREFERRED EMBODIMENTS

I. The Present Invention

Figure 3:
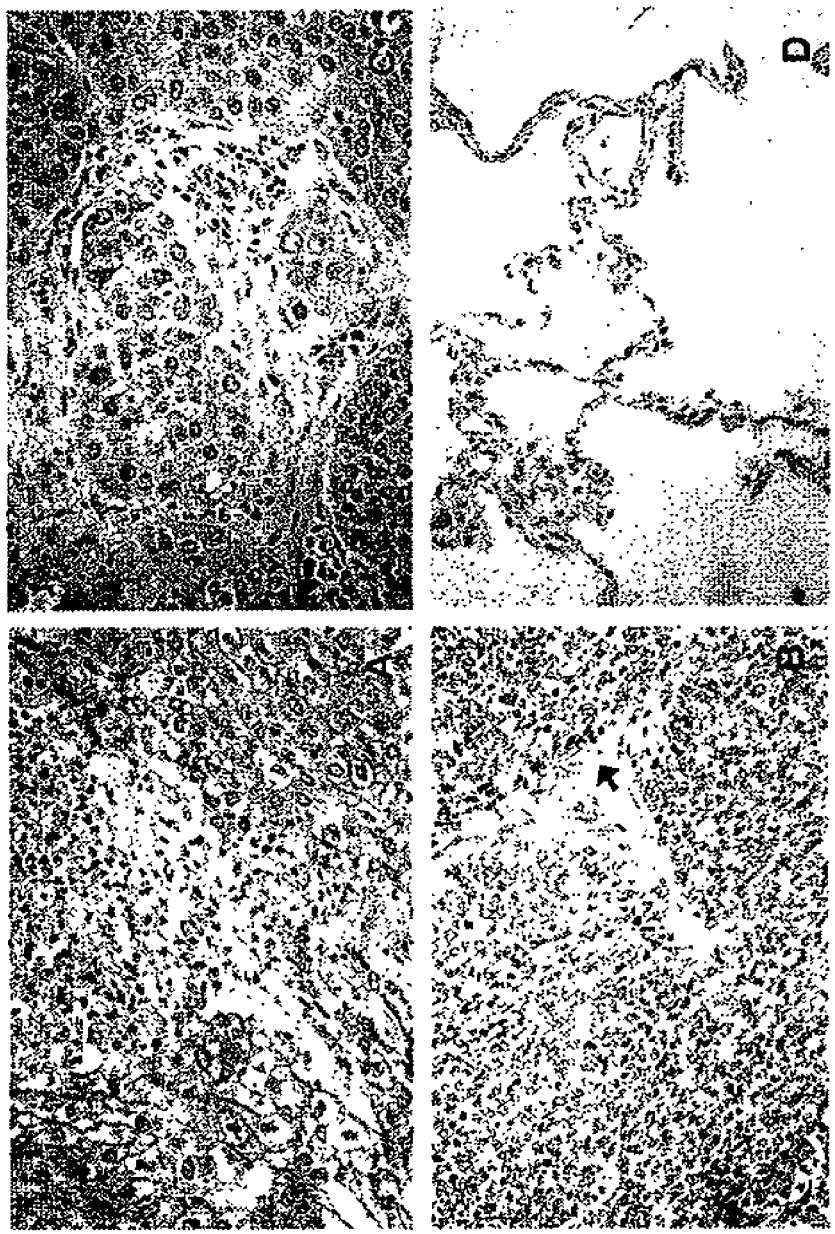
FIG. 3. Immunohistochemistry with an antibody to extracellular domain of Notch3. Cytoplasmic and membranous staining is observed in squamous cell carcinoma (A) and adenocarcinoma (C) of the lung as compared to aneuroendocrine tumor (B) and normal lung (D). In panel B, slight staining is seen in blood vessels (arrow) within the tumor, consistent with other studies demonstrating normal staining of Notch3 in blood vessels FIGS. 4A-D. Notch3 alters lung morphology of SP-C-N3IC transgenic mice at E18.5. Five μm-thick lung sections of wild-type littermate controls (FIGS. 4A, 4C) show that epithelial layer of terminal airways are thin and comprised mostly of type I pneumocytes. The terminal lung epithelium of transgenic embryos (FIGS. 4B, 4D) demonstrates severe metaplasia, composed mostly of undifferentiated cuboidal cells (arrowheads). No type I pneumocyte was found. The mesenchyme is abnormally abundant compared to that seen in the wild-type littermate. Bars=50 μm; br., bronchiole; m, mesenchyme; v, vessel.

Many genes that are important in tumor initiation, progression, or survival play crucial roles in normal development. The Notch receptors are members of an evolutionarily conserved family that is essential for the control of cell fate determination during the development of many multicellular organisms. The core components of the Notch pathway are listed in Table 1. Their functions were first discovered in *Drosophila melanogaster* almost 80 years ago, when a heterozygous deletion was found to result in "notches" at the wing margins. Mutations in Notch genes alter cell fate determination, causing cells destined to become epidermis to instead give rise to neural tissue (reviewed in Artavanis-Tsakonas, 1999). Notch signaling is classically divided into two fundamental types: inductive and lateral signaling. Induction occurs between two nonequivalent cells, where one cell expresses the receptor and the other expresses the ligand, and through their interaction one cell adopts a different fate. In contrast, lateral signaling occurs between equivalent cells, and through competitive inhibition, adjacent cells are forced to follow a different fate. The role of Notch pathway signaling in mammals has been studied extensively in lymphogenesis, ondotogenesis, neurogenesis, hair and sensory development (Beatus and Leandahl, 1998; Mitsiadis et al., 1998; Lanford et al., 1999; Robey et al., 1996).

TABLE 1

Core components of the Notch pathway in worms, flies, and mammals

| Component | C. elegans | Drosophila | Mammals |
|---|---|---|---|
| DSL Ligands | LAG-2, APX-1, DSL-1 | Delta, Serrate | Delta-like-1, -3 and -4 Jagged1, Jagged 2 |
| Notch Receptors | LIN-12, Glp-1 | Notch | Notch 1-4 |
| CSL Factors | LAG-1 | Suppressor of Hairless | CBF-1 |
| Corepressor | | Hairless, Groucho, dCTBP, SMRTER | SMRT, NcoR, CIR |
| Coactivators | | Mastermind | Mastermind |
| Target Genes | | Enhancer of Split, Hey | HES1-7, Hey1-2 |

*adapted from Sundaram (2005).

II. Notch3

Notch Plays A Key Role In Vascular Development and Homeostasis. In adult mammals, the expression of Notch receptors is restricted to the vascular systems. Mice with targeted mutations of the Notch pathway components, such as Jagged1, Delta-like-1 and the Notch1 receptor, die during embryogenesis from defects in vascular morphogenesis (Krebs et al., 2000; Xue et al., 1999; Hrabe de Angelis et al., 1997). While Notch3–/– mice are fertile and viable, these adult mice exhibit structural defects in the distal arteries and arterial myogenic response, reflecting the lack of proper development in vascular smooth muscle cells (Domenga et al., 2004). These observations indicate that the Notch signaling pathway is important in both vascular development and homeostasis. Not surprisingly, many of the processes involved in embryonic vascular development are mirrored in tumor angiogenesis. For example, induction of Notch ligand Jagged1 promotes capillary-like sprout formation in tumor cells (Zeng et al., 2005). Finally, inhibition of Notch activation by γ-secretase inhibitors also inhibits angiogenesis and tumor proliferation (Paris et al., 2005; Williams et al., 2005). These observations support a role of Notch pathway in normal and tumor angiogenesis.

Activation of Notch Signaling requires Proteolytic Cleavage of the Receptor. While *Drosophila* possesses a single Notch gene, there are four members of the Notch family in mammals: Notch1 (TAN1), Notch2, Notch3 and Notch4/Int-4. The core components of the Notch pathway are listed in Table 1. Notch is expressed on cell surfaces as a single-pass, heterodimeric receptor. The ligands are also transmembrane proteins of the DSL (Delta/Serrate/LAG-2) family that can be expressed not only on adjacent cells but also on the very same cell expressing the Notch receptors. Receptor-ligand interaction triggers proteolysis at the extracellular S2 site near the transmembrane domain and at the S3 site (FIG. 1). A TNF-α converting enzyme (TACE) and a presenillin-1-dependent γ-secretase are believed to be responsible for the proteolytic processing at sites S2 and S3, respectively. The final cleavage releases the C-terminal, intracellular domain (NICD), which then translocates to the nucleus, recruits coactivators such as mastermind and p300, and binds to CSL (CBF/Suppressor of Hairless/LAG-1) factors. In the absence of Notch signaling, CSL proteins in association with corepressors repress target gene transcription. Thus, Notch signaling causes a switch from transcriptional repression to transcriptional activation of CSL target genes (a review of Notch processing in Mumm and Kopan (2000).

The Notch Signaling Pathway Is Oncogenic. Many key pathways in development play important roles in tumorigenesis when altered. Notch1 was first identified in association with a t(7:9) translocation found in a subset of human T-cell acute lymphoblastoid leukemias (T-ALLs) (Ellisen et al., 1991). While less than 1% of human T-ALLs exhibit the t(7:9), Notch activating mutations have been observed in 50% of human T-ALLs (Weng et al., 2004; Ma et al., 1999). The expression of the constitutively activated intracellular domain (NICD) of Notch1 in bone marrow cells confers an oncogenic phenotype (Pear et al., 1996). Similar observations have been made linking Notch family members with cancer pathogenesis as well (Jhappan et al., 1992; Rohn et al., 1996). Constitutive activation of Notch3 in transgenic mice results in T-cell lymphoblastic leukemia, and in human T-ALL, loss of Notch3 expression correlates with clinical remission Bellavia et al., 2002; Bellavia et al., 2000). Moreover, activated Notch3 confers resistance to apoptosis and loss of contact inhibition in smooth muscle cells (Wang et al., 2002; Sweeney et al., 2004; Campos et al., 2002). Notch3 has been found to be highly expressed in other tumors, including lung, pancreatic and ovarian carcinoma, using gene expression microarray (Dang et al., 2000; Miyamoto et al., 2003; Lu et al., 2004). Similar studies demonstrate correlations between aberrant Notch ligand/receptor expression and tumor development in various systems (Miyamoto et al., 2003; Santagata et al., 2004; Purow et al., 2005; Callahan and Egan, 2004). The inventors published data demonstrating that inhibition of Notch3 activation using a dominant-negative receptor reduces tumor phenotype (Haruki et al., 2005). Taken together, these observations suggest that the Notch pathway is functionally significant in solid tumors and can serve as a target for therapeutic intervention.

Notch Crosstalks with the Ras Pathway. In both mammals and invertebrates such as *Drosophila* and *C. elegans*, Notch receptors signal primarily by the binding to members of the CSL family of transcription factors and related transcription co-activators. However, Notch is known to interact with other pathways including the Wingless/B-catenin and NF-κB pathways (Johnston and Edgar, 1998; Oswald et al., 1998). One pathway that plays prominently in both development and neoplastic transformation is the EGF/ras/MAPK pathway. Notch has been shown in developing organisms to antagonize EGF signaling in cell fate determination through modulation of the MAPK pathway (Faux et al., 2001; Ahmad and Dooley, 1998; Berset et al., 2001). In other cases, however, the Ras and Notch pathways cooperate in promoting certain cell fates (Yoo et al., 2004). As in flies and worms, specific outcomes of EGF and Notch pathways in mammals are context dependent. In mammals, Wang et al. demonstrated that Notch3 induces phosphorylation of ERK1/ERK2 (p44/p42) in vascular smooth muscle cells (Wang et al., 2002). Current evidence indicates that malignant transformation by Notch requires activated Ras (Haruki et al., 2005; Fitzgerald et al., 2000). On the other hand, activated Notch1 was found to inhibit Fgfdependent malignant transformation of NIH3T3 cells (Small et al., 2003). While further work is required to fully understand the mechanism of interactions between Ras and Notch pathways, the preliminary data demonstrate a cooperative relationship between Notch3 signaling and the ras pathway. This observation suggests that combinatorial therapeutic approach will have better efficacy in the treatment of patients with lung cancers. FIG. 2 summarizes known potential Notch-ras interactions in both the development and cancer context.

γ-Secretase Inhibitors Demonstrate Antitumor Effects. Proteolytic processing of Notch receptors following ligand binding is necessary for their activation. The final proteolytic cleavage by the γ-secretase protein complex releases the Notch intracellular domain required for target gene transcription. Thus, pharmacologic intervention that inhibits the activity of any of the proteases can potentially inhibit tumor growth in Notch-dependent cancer. Interestingly, at the same time that presenilins were shown to be essential for Notch signaling, they were discovered as susceptibility loci for Alzheimer's disease (Levitan and Greenwald, 1995). The pathogenesis of Alzheimer's disease is believed to be the accumulation of amyloid β-peptides (Aβ) and formation of amyloid plaques. These peptides are derived from the proteolytic processing of the β-amyloid precursor protein (APP) through an intermediate fragment (C99) by γ-secretases (Dovey et al., 2001). Given the great need for better treatment of patients with Alzheimer's disease, inhibitors targeting γ-secretase are being aggressively pursued by many pharmaceutical companies. Predictably, many of these compounds were found to inhibit Notch processing as well. Furthermore, γ-secretase inhibitors block Notch activation and induce apoptosis in multiple cancer cell lines (Qin et al., 2004; Curry et al., 2005; Alves da Costa, 2004). In vivo, these compounds inhibit angiogenesis and tumor growth (Paris et al., 2005). These inhibitors are known to have non-Notch targets, such as erb-4 and CD44, but our data suggest that Notch inhibition may be a component of the observed antitumor effects (Pelletier et al., 2006; Linggi et al., 2006). However, from a practical standpoint, since erb-4 and CD44 are known to be oncogenic, these inhibitors may actually have increased efficacy by virtue of their multiple targets. In fact, a γ-secretase inhibitor by Merck & Co., Inc, is currently in Phase I trials for patients with metastatic or locally advanced breast cancer and for patients with T-cell acute leukemias.

A. Features of the Polypeptide

Notch3 is a 2321 amino acid protein (243659 Da Q9UM47; SEQ ID NO:2) that exists as a heterodimer of a C-terminal fragment (TM) and an N-terminal fragment (EC) which are probably linked by disulfide bonds. It has been shown to iteract with MAML1, MAML2 and MAML3 which act as transcriptional coactivators for NOTCH3. It is localized in the cell membrane and is a single-pass type I membrane protein. Following proteolytical processing, the notch intracellular domain (NICD) causes translocation to the nucleus. Its only known post-translational modification is glycosylation.

Notch3 functions as a receptor for membrane-bound ligands Jagged1, Jagged2 and Delta1 to regulate cell-fate determination. Upon ligand activation through the released NICD, it forms a transcriptional activator complex with CBF-1 and activates genes of the enhancer of split locus. As discussed above, it has effects the implementation of differentiation, proliferation and apoptosis programs. It is located at 19p13.2-p13.1.

B. Peptides

Notch3 peptides will comprise molecules of 5 to no more than about 50 residues in length. A particular length may be less than 39 residues, less than 35 residues, less than 30 residues, less than 25 residues, less than 20 residues, less than 15 residues, or less than 13, including 5, 6, 7, 8, 9, 10, 11 or 12 residues, and ranges of 5-11 residues, 5-15 residues, 5-20 residues, 5-25 residues, 5-30 residues, 5-35 residues, 5-38 residues, or 5-40 residues. The peptides may be generated synthetically or by recombinant techniques, and are purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration), as described in further detail below.

The peptides may be labeled using various molecules, such as fluorescent, chromogenic or colorimetric agents. The peptides may also be linked to other molecules, including other anti-cancer agents. The links may be direct or through distinct linker molecules. The linker molecules in turn may be subject, in vivo, to cleavage, thereby releasing the agent from the peptide. Peptides may also be rendered multimeric by linking to larger, and possibly inert, carrier molecules.

C. Variants

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent or improved molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 2 shows the codons that encode particular amino acids.

TABLE 2

| Amino Acids   |     |   | Codons                      |
|---------------|-----|---|-----------------------------|
| Alanine       | Ala | A | GCA GCC GCG GCU             |
| Cysteine      | Cys | C | UGC UGU                     |
| Aspartic acid | Asp | D | GAC GAU                     |
| Glutamic acid | Glu | E | GAA GAG                     |
| Phenylalanine | Phe | F | UUC UUU                     |
| Glycine       | Gly | G | GGA GGC GGG GGU             |
| Histidine     | His | H | CAC CAU                     |
| Isoleucine    | Ile | I | AUA AUC AUU                 |
| Lysine        | Lys | K | AAA AAG                     |
| Leucine       | Leu | L | UUA UUG CUA CUC CUG CUU     |
| Methionine    | Met | M | AUG                         |
| Asparagine    | Asn | N | AAC AAU                     |
| Proline       | Pro | P | CCA CCC CCG CCU             |
| Glutamine     | Gln | Q | CAA CAG                     |
| Arginine      | Arg | R | AGA AGG CGA CGC CGG CGU     |
| Serine        | Ser | S | AGC AGU UCA UCC UCG UCU     |
| Threonine     | Thr | T | ACA ACC ACG ACU             |
| Valine        | Val | V | GUA GUC GUG GUU             |
| Tryptophan    | Trp | W | UGG                         |
| Tyrosine      | Tyr | Y | UAC UAU                     |

In making substitutional variants, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, for example, Johnson et al., (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of Notch3, but with altered and even improved characteristics.

D. Fusions

A specialized kind of insertional variant is the fusion protein. This molecule generally has all or a substantial portion (e.g., an intracellular, transmembrane or extracellular domain) of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

E. Purification of Proteins/Peptides

It will be desirable to purify Notch3 or fragments thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fuctose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

F. Synthesis

Because of their relatively small size, the peptides of the invention can also be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

G. Antigen Compositions

The present invention also provides for the use of Notch3 proteins or peptides as antigens for the immunization of animals relating to the production of antibodies. It is envisioned that either Notch3, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Particular agents are the carriers are keyhole limpet hemocyannin (KLH) or bovine serum albumin (BSA).

III. Nucleic Acids

The present invention also provides, in another embodiment, genes encoding Notch3 or fragments (peptides) thereof. A gene for the human Notch3 molecule has been identified. The present invention is not limited in scope to this gene, however, as one of ordinary skill in the could readily identify related homologs in various other species (e.g., mouse, rat, rabbit, dog. monkey, gibbon, chimp, ape, baboon, cow, pig, horse, sheep, cat and other species).

In addition, it should be clear that the present invention is not limited to the specific nucleic acids disclosed herein. As discussed below, a "Notch3 gene" may contain a variety of different bases and yet still produce a corresponding polypeptide that is functionally indistinguishable from, and in some cases structurally identical to, the human gene disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the function of Notch3.

A. Nucleic Acids Encoding Notch3

Nucleic acids according to the present invention may encode an entire Notch3 coding sequence (Accession No. U97669; SEQ ID NO:1), a domain of Notch3 that expresses a tumor suppressing function, or any other fragment of the Notch3 sequences set forth herein. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given Notch3 from a given species may be represented by natural variants that have slightly different nucleic acid sequences but, nonetheless, encode the same protein (see Table 1, above).

As used in this application, the term "a nucleic acid encoding a Notch3" refers to a nucleic acid molecule that has been isolated free of total cellular nucleic acid. In certain embodiments, the invention concerns a nucleic acid sequence essentially as set forth in SEQ ID NO:2. The term "as set forth in SEQ ID NO:2" means that the nucleic acid sequence substantially corresponds to a portion of SEQ ID NO:2. The term "functionally equivalent codon" is used herein to refer to codons that encode the same amino acid, such as the six codons for arginine or serine, and also refers to codons that encode biologically equivalent amino acids, as discussed in the following pages.

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NO:2. Sequences that are essentially the same as those set forth in SEQ ID NO:2 also may be functionally defined as sequences that are capable of hybridizing to a nucleic acid segment containing the complement of SEQ ID NO:2 under standard conditions.

The DNA segments of the present invention include those encoding biologically functional equivalent Notch3 proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

B. Oligonucleotide Probes and Primers

Naturally, the present invention also encompasses DNA segments that are complementary, or essentially complementary, to the sequence set forth in SEQ ID NO:2. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:2 under relatively stringent conditions such as those described herein. Such sequences may encode the entire Notch3 protein or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, 90, 95, 100, 110, 114 or more base pairs will be used, although others are contemplated. Longer polynucleotides encoding 250, 500, 1000, 1212, 1500, 2000, 2500, 3000 or longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C. Formamide and SDS also may be used to alter the hybridization conditions.

One method of using probes and primers of the present invention is in the search for genes related to Notch3 or, more particularly, homologs of Notch3 from other species. Normally, the target DNA will be a genomic or cDNA library, although screening may involve analysis of RNA molecules. By varying the stringency of hybridization, and the region of the probe, different degrees of homology may be discovered. Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single-stranded and double-stranded form. Typical vectors useful in site-directed mutagenesis include vectors such as the M13 phage. These phage vectors are commercially available and their use is generally well known to those skilled in the art. Double-stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double-stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Vectors for Cloning, Gene Transfer and Expression

Within certain embodiments, expression vectors are employed to express the Notch3 polypeptide product, which can then be purified for various uses. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

(i) Regulatory Elements

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally-associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally-occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. One example is the native Notch3 promoter. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 3 lists several elements/promoters that may be employed, in the context of the present invention, to regulate the expression of a gene. This list is not intended to be exhaustive of all the possible elements involved in the promotion of expression but, merely, to be exemplary thereof. Table 4 provides examples of inducible elements, which are regions of a nucleic acid sequence that can be activated in response to a specific stimulus.

TABLE 3

| Promoter/Enhancer | Promoter and/or Enhancer References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |

TABLE 3-continued

| Promoter and/or Enhancer | |
|---|---|
| Promoter/Enhancer | References |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $α_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 4

| Inducible Elements | | |
|---|---|---|
| Element | Inducer | References |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |

TABLE 4-continued

| Inducible Elements | | |
|---|---|---|
| Element | Inducer | References |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996). Tumor specific promoters also will find use in the present invention. Some such promoters are set forth in Tables 4 and 5.

TABLE 5

| Candidate Tissue-Specific Promoters for Cancer Gene Therapy | | |
|---|---|---|
| Tissue-specific promoter | Cancers in which promoter is active | Normal cells in which promoter is active |
| Carcinoembryonic antigen (CEA)* | Most colorectal carcinomas; 50% of lung carcinomas; 40-50% of gastric carcinomas; most pancreatic carcinomas; many breast carcinomas | Colonic mucosa; gastric mucosa; lung epithelia; eccrine sweat glands; cells in testes |
| Prostate-specific antigen (PSA) | Most prostate carcinomas | Prostate epithelium |
| Vasoactive intestinal peptide (VIP) | Majority of non-small cell lung cancers | Neurons; lymphocytes; mast cells; eosinophils |
| Surfactant protein A (SP-A) | Many lung adenocarcinomas | Type II pneumocytes; Clara cells |
| Human achacte-scute homolog (hASH) | Most small cell lung cancers | Neuroendocrine cells in lung |
| Mucin-1 (MUC1)** | Most adenocarcinomas (originating from any tissue) | Glandular epithelial cells in breast and in respiratory, gastrointestinal, and genitourinary tracts |
| Alpha-fetoprotein | Most hepatocellular carcinomas; possibly many testicular cancers | Hepatocytes (under certain conditions); testis |
| Albumin | Most hepatocellular carcinomas | Hepatocytes |
| Tyrosinase | Most melanomas | Melanocytes; astrocytes; Schwann cells; some neurons |
| Tyrosine-binding protein (TRP) | Most melanomas | Melanocytes; astrocytes, Schwann cells; some neurons |
| Keratin 14 | Presumably many squamous cell carcinomas (e.g., Head and neck cancers) | Keratinocytes |

TABLE 5-continued

Candidate Tissue-Specific Promoters for Cancer Gene Therapy

| Tissue-specific promoter | Cancers in which promoter is active | Normal cells in which promoter is active |
|---|---|---|
| EBV LD-2 | Many squamous cell carcinomas of head and neck | Keratinocytes of upper digestive Keratinocytes of upper digestive tract |
| Glial fibrillary acidic protein (GFAP) | Many astrocytomas | Astrocytes |
| Myelin basic protein (MBP) | Many gliomas | Oligodendrocytes |
| Testis-specific angiotensin-converting enzyme (Testis-specific ACE) | Possibly many testicular cancers | Spermatazoa |
| Osteocalcin | Possibly many osteosarcomas | Osteoblasts |

TABLE 6

Candidate Promoters for Tissue-Specific Targeting of Tumors

| Promoter | Cancers in which Promoter is active | Normal cells in which Promoter is active |
|---|---|---|
| E2F-regulated promoter | Almost all cancers | Proliferating cells |
| HLA-G | Many colorectal carcinomas; many melanomas; possibly many other cancers | Lymphocytes; monocytes; spermatocytes; trophoblast |
| FasL | Most melanomas; many pancreatic carcinomas; most astrocytomas possibly many other cancers | Activated leukocytes: neurons; endothelial cells; keratinocytes; cells in immunoprivileged tissues; some cells in lungs, ovaries, liver, and prostate |
| Myc-regulated promoter | Most lung carcinomas (both small cell and non-small cell); most colorectal carcinomas | Proliferating cells (only some cell-types): mammary epithelial cells (including non-proliferating) |
| MAGE-1 | Many melanomas; some non-small cell lung carcinomas; some breast carcinomas | Testis |
| VEGF | 70% of all cancers (constitutive overexpression in many cancers) | Cells at sites of neovascularization (but unlike in tumors, expression is transient, less strong, and never constitutive) |
| bFGF | Presumably many different cancers, since bFGF expression is induced by ischemic conditions | Cells at sites of ischemia (but unlike tumors, expression is transient, less strong, and never constitutive) |
| COX-2 | Most colorectal carcinomas; many lung carcinomas; possibly many other cancers | Cells at sites of inflammation |
| IL-10 | Most colorectal carcinomas; many lung carcinomas; many squamous cell carcinomas of head and neck; possibly many other cancers | Leukocytes |
| GRP78/ BiP | Presumably many different cancers, since GRP7S expression is induced by tumor-specific conditions | Cells at sites of ishemia |
| CarG elements from Egr-1 | Induced by ionization radiation, so conceivably most tumors upon irradiation | Cells exposed to ionizing radiation; leukocytes |

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

(ii) IRES

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

(iii) Multi-Purpose Cloning Sites

Vectors can include a multiple cloning site (MCS), which is a nucleic acid region that contains multiple restriction enzyme sites, any of which can be used in conjunction with standard recombinant technology to digest the vector. See Carbonelli et al., 1999, Levenson et al., 1998, and Cocea, 1997, incorporated herein by reference. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

(iv) Splicing Sites

Most transcribed eukaryotic RNA molecules will undergo RNA splicing to remove introns from the primary transcripts.

Vectors containing genomic eukaryotic sequences may require donor and/or acceptor splicing sites to ensure proper processing of the transcript for protein expression (see Chandler et al., 1997, herein incorporated by reference.)

(v) Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

(vi) Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

(vii) Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

(viii) Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

(ix) Viral Vectors

The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simplex virus, retrovirus and adeno-associated virus vectors are being evaluated currently for treatment of diseases such as cancer, cystic fibrosis, Gaucher disease, renal disease and arthritis (Robbins and Ghivizzani, 1998; Imai et al., 1998; U.S. Pat. No. 5,670,488). The various viral vectors described below, present specific advantages and disadvantages, depending on the particular genetherapeutic application.

Adenoviral Vectors. In particular embodiments, an adenoviral expression vector is contemplated for the delivery of expression constructs. "Adenovirus expression vector" is meant to include those constructs containing adenovirus sequences sufficient to (a) support packaging of the construct and (b) to ultimately express a tissue or cell-specific construct that has been cloned therein.

Adenoviruses comprise linear, double-stranded DNA, with a genome ranging from 30 to 35 kb in size (Reddy et al., 1998; Morrison et al., 1997; Chillon et al., 1999). An adenovirus expression vector according to the present invention comprises a genetically engineered form of the adenovirus. Advantages of adenoviral gene transfer include the ability to infect a wide variety of cell types, including non-dividing cells, a mid-sized genome, ease of manipulation, high infectivity and the ability to be grown to high titers (Wilson, 1996). Further, adenoviral infection of host cells does not result in chromosomal integration because adenoviral DNA can replicate in an episomal manner, without potential genotoxicity associated with other viral vectors. Adenoviruses also are structurally stable (Marienfeld et al., 1999) and no genome rearrangement has been detected after extensive amplification (Parks et al., 1997; Bett et al., 1993).

Salient features of the adenovirus genome are an early region (E1, E2, E3 and E4 genes), an intermediate region (pIX gene, Iva2 gene), a late region (L1, L2, L3, L4 and L5 genes), a major late promoter (MLP), inverted-terminal-repeats (ITRs) and a ψ sequence (Zheng, et al., 1999; Robbins et al., 1998; Graham and Prevec, 1995). The early genes E1, E2, E3 and E4 are expressed from the virus after infection and encode polypeptides that regulate viral gene expression, cellular gene expression, viral replication, and inhibition of cellular apoptosis. Further on during viral infection, the MLP is activated, resulting in the expression of the late (L) genes, encoding polypeptides required for adenovirus encapsidation. The intermediate region encodes components of the adenoviral capsid. Adenoviral inverted terminal repeats (ITRs; 100-200 bp in length), are cis elements, and function as origins of replication and are necessary for viral DNA replication. The ψ sequence is required for the packaging of the adenoviral genome.

A common approach for generating an adenoviruses for use as a gene transfer vector is the deletion of the E1 gene (E1⁻), which is involved in the induction of the E2, E3 and E4 promoters (Graham and Prevec, 1995). Subsequently, a therapeutic gene or genes can be inserted recombinantly in place of the E1 gene, wherein expression of the therapeutic gene(s) is driven by the E1 promoter or a heterologous promoter. The E1⁻, replication-deficient virus is then proliferated in a "helper" cell line that provides the E1 polypeptides in trans (e.g., the human embryonic kidney cell line 293). Thus, in the present invention it may be convenient to introduce the transforming construct at the position from which the E1-coding sequences have been removed. However, the position of insertion of the construct within the adenovirus sequences is not critical to the invention. Alternatively, the E3 region, portions of the E4 region or both may be deleted, wherein a heterologous nucleic acid sequence under the control of a promoter operable in eukaryotic cells is inserted into the adenovirus genome for use in gene transfer (U.S. Pat. No. 5,670,488; U.S. Pat. No. 5,932,210, each specifically incorporated herein by reference).

Although adenovirus based vectors offer several unique advantages over other vector systems, they often are limited by vector immunogenicity, size constraints for insertion of recombinant genes and low levels of replication. The preparation of a recombinant adenovirus vector deleted of all open reading frames, comprising a full length dystrophin gene and the terminal repeats required for replication (Haecker et al., 1996) offers some potentially promising advantages to the above mentioned adenoviral shortcomings. The vector was grown to high titer with a helper virus in 293 cells and was capable of efficiently transducing dystrophin in mdx mice, in myotubes in vitro and muscle fibers in vivo. Helper-dependent viral vectors are discussed below.

A major concern in using adenoviral vectors is the generation of a replication-competent virus during vector production in a packaging cell line or during gene therapy treatment of an individual. The generation of a replication-competent virus could pose serious threat of an unintended viral infection and pathological consequences for the patient. Armentano et al. (1990), describe the preparation of a replication-defective adenovirus vector, claimed to eliminate the potential for the inadvertent generation of a replication-competent adenovirus (U.S. Pat. No. 5,824,544, specifically incorporated herein by reference). The replication-defective adenovirus method comprises a deleted E1 region and a relocated protein IX gene, wherein the vector expresses a heterologous, mammalian gene.

Other than the requirement that the adenovirus vector be replication defective, or at least conditionally defective, the nature of the adenovirus vector is not believed to be crucial to the successful practice of the invention. The adenovirus may be of any of the 42 different known serotypes and/or subgroups A-F. Adenovirus type 5 of subgroup C is the preferred starting material in order to obtain the conditional replication-defective adenovirus vector for use in the present invention. This is because adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Adenovirus growth and manipulation is known to those of skill in the art, and exhibits broad host range in vitro and in vivo (U.S. Pat. No. 5,670,488; U.S. Pat. No. 5,932,210; U.S. Pat. No. 5,824,544). This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. Many experiments, innovations, preclinical studies and clinical trials are currently under investigation for the use of adenoviruses as gene delivery vectors. For example, adenoviral gene delivery-based gene therapies are being developed for liver diseases (Han et al., 1999), psychiatric diseases (Lesch, 1999), neurological diseases (Smith, 1998; Hermens and Verhaagen, 1998), coronary diseases (Feldman et al., 1996), muscular diseases (Petrof, 1998), gastrointestinal diseases (Wu, 1998) and various cancers such as colorectal (Fujiwara and Tanaka, 1998; Dorai et al., 1999), pancreatic, bladder (Irie et al., 1999), head and neck (Blackwell et al., 1999), breast (Stewart et al., 1999), lung (Batra et al., 1999) and ovarian (Vanderkwaak et al., 1999).

Retroviral Vectors. In certain embodiments of the invention, the use of retroviruses for gene delivery are contemplated. Retroviruses are RNA viruses comprising an RNA genome. When a host cell is infected by a retrovirus, the genomic RNA is reverse transcribed into a DNA intermediate which is integrated into the chromosomal DNA of infected cells. This integrated DNA intermediate is referred to as a provirus. A particular advantage of retroviruses is that they can stably infect dividing cells with a gene of interest (e.g., a therapeutic gene) by integrating into the host DNA, without expressing immunogenic viral proteins. Theoretically, the integrated retroviral vector will be maintained for the life of the infected host cell, expressing the gene of interest.

The retroviral genome and the proviral DNA have three genes: gag, pol, and env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication.

A recombinant retrovirus of the present invention may be genetically modified in such a way that some of the structural, infectious genes of the native virus have been removed and replaced instead with a nucleic acid sequence to be delivered to a target cell (U.S. Pat. No. 5,858,744; U.S. Pat. No. 5,739,018, each incorporated herein by reference). After infection of a cell by the virus, the virus injects its nucleic acid into the cell and the retrovirus genetic material can integrate into the host cell genome. The transferred retrovirus genetic material is then transcribed and translated into proteins within the host cell. As with other viral vector systems, the generation of a replication-competent retrovirus during vector production or during therapy is a major concern. Retroviral vectors suitable for use in the present invention are generally defective retroviral vectors that are capable of infecting the target cell, reverse transcribing their RNA genomes, and integrating the reverse transcribed DNA into the target cell genome, but are incapable of replicating within the target cell to produce infectious retroviral particles (e.g., the retroviral genome transferred into the target cell is defective in gag, the gene encoding virion structural proteins, and/or in pol, the gene encoding reverse transcriptase). Thus, transcription of the provirus and assembly into infectious virus occurs in the presence of an appropriate helper virus or in a cell line containing appropriate sequences enabling encapsidation without coincident production of a contaminating helper virus.

The growth and maintenance of retroviruses is known in the art (U.S. Pat. No. 5,955,331; U.S. Pat. No. 5,888,502, each specifically incorporated herein by reference). Nolan et al. describe the production of stable high titre, helper-free retrovirus comprising a heterologous gene (U.S. Pat. No. 5,830,725, specifically incorporated herein by reference). Methods for constructing packaging cell lines useful for the generation of helper-free recombinant retroviruses with amphoteric or ecotrophic host ranges, as well as methods of using the recombinant retroviruses to introduce a gene of interest into eukaryotic cells in vivo and in vitro are contemplated in the present invention (U.S. Pat. No. 5,955,331).

Currently, the majority of all clinical trials for vector-mediated gene delivery use murine leukemia virus (MLV)-based retroviral vector gene delivery (Robbins et al., 1998; Miller et al., 1993). Disadvantages of retroviral gene delivery includes a requirement for ongoing cell division for stable infection and a coding capacity that prevents the delivery of large genes. However, recent development of vectors such as lentivirus (e.g., HIV), simian immunodeficiency virus (SIV) and equine infectious-anemia virus (EIAV), which can infect certain non-dividing cells, potentially allow the in vivo use of retroviral vectors for gene therapy applications (Amado and Chen, 1999; Klimatcheva et al., 1999; White et al., 1999; Case et al., 1999). For example, HIV-based vectors have been used to infect non-dividing cells such as neurons (Miyatake et al., 1999), islets (Leibowitz et al., 1999) and muscle cells (Johnston et al., 1999). The therapeutic delivery of genes via retroviruses are currently being assessed for the treatment of various disorders such as inflammatory disease (Moldawer et al., 1999), AIDS (Amado and Chen, 1999; Engel and Kohn, 1999), cancer (Clay et al., 1999), cerebrovascular disease (Weihl et al., 1999) and hemophilia (Kay, 1998).

Herpesviral Vectors. Herpes simplex virus (HSV) type I and type II contain a double-stranded, linear DNA genome of approximately 150 kb, encoding 70-80 genes. Wild type HSV are able to infect cells lytically and to establish latency in certain cell types (e.g., neurons). Similar to adenovirus, HSV also can infect a variety of cell types including muscle (Yeung et al., 1999), ear (Derby et al., 1999), eye (Kaufman et al., 1999), tumors (Yoon et al., 1999; Howard et al., 1999), lung (Kohut et al., 1998), neuronal (Gamido et al., 1999; Lachmann and Efstathiou, 1999), liver (Miyatake et al., 1999; Kooby et al., 1999) and pancreatic islets (Rabinovitch et al., 1999).

HSV viral genes are transcribed by cellular RNA polymerase II and are temporally regulated, resulting in the transcription and subsequent synthesis of gene products in roughly three discernable phases or kinetic classes. These phases of genes are referred to as the Immediate Early (IE) or alpha genes, Early (E) or beta genes and Late (L) or gamma genes. Immediately following the arrival of the genome of a virus in the nucleus of a newly infected cell, the IE genes are transcribed. The efficient expression of these genes does not require prior viral protein synthesis. The products of IE genes are required to activate transcription and regulate the remainder of the viral genome.

For use in therapeutic gene delivery, HSV must be rendered replication-defective. Protocols for generating replication-defective HSV helper virus-free cell lines have been described (U.S. Pat. No. 5,879,934; U.S. Pat. No. 5,851,826, each specifically incorporated herein by reference in its entirety). One IE protein, Infected Cell Polypeptide 4 (ICP4), also known as alpha 4 or Vmw175, is absolutely required for both virus infectivity and the transition from IE to later transcription. Thus, due to its complex, multifunctional nature and central role in the regulation of HSV gene expression, ICP4 has typically been the target of HSV genetic studies.

Phenotypic studies of HSV viruses deleted of ICP4 indicate that such viruses will be potentially useful for gene transfer purposes (Krisky et al., 1998a). One property of viruses deleted for ICP4 that makes them desirable for gene transfer is that they only express the five other IE genes: ICP0, ICP6, ICP27, ICP22 and ICP47 (DeLuca et al., 1985), without the expression of viral genes encoding proteins that direct viral DNA synthesis, as well as the structural proteins of the virus. This property is desirable for minimizing possible deleterious effects on host cell metabolism or an immune response following gene transfer. Further deletion of IE genes ICP22 and ICP27, in addition to ICP4, substantially improve reduction of HSV cytotoxicity and prevented early and late viral gene expression (Krisky et al., 1998b).

The therapeutic potential of HSV in gene transfer has been demonstrated in various in vitro model systems and in vivo for diseases such as Parkinson's (Yamada et al., 1999), retinoblastoma (Hayashi et al., 1999), intracerebral and intradermal tumors (Moriuchi et al., 1998), B-cell malignancies (Suzuki et al., 1998), ovarian cancer (Wang et al., 1998) and Duchenne muscular dystrophy (Huard et al., 1997).

Adeno-Associated Viral Vectors. Adeno-associated virus (AAV), a member of the parvovirus family, is a human virus that is increasingly being used for gene delivery therapeutics. AAV has several advantageous features not found in other viral systems. First, AAV can infect a wide range of host cells, including non-dividing cells. Second, AAV can infect cells from different species. Third, AAV has not been associated with any human or animal disease and does not appear to alter the biological properties of the host cell upon integration. For example, it is estimated that 80-85% of the human population has been exposed to AAV. Finally, AAV is stable at a wide range of physical and chemical conditions which lends itself to production, storage and transportation requirements.

The AAV genome is a linear, single-stranded DNA molecule containing 4681 nucleotides. The AAV genome generally comprises an internal non-repeating genome flanked on each end by inverted terminal repeats (ITRs) of approximately 145 bp in length. The ITRs have multiple functions, including origins of DNA replication, and as packaging signals for the viral genome. The internal non-repeated portion of the genome includes two large open reading frames, known as the AAV replication (rep) and capsid (cap) genes. The rep and cap genes code for viral proteins that allow the virus to replicate and package the viral genome into a virion. A family of at least four viral proteins are expressed from the AAV rep region, Rep 78, Rep 68, Rep 52, and Rep 40, named according to their apparent molecular weight. The AAV cap region encodes at least three proteins, VP1, VP2, and VP3.

AAV is a helper-dependent virus requiring co-infection with a helper virus (e.g., adenovirus, herpesvirus or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. Although AAV can infect cells from different species, the helper virus must be of the same species as the host cell (e.g., human AAV will replicate in canine cells co-infected with a canine adenovirus).

AAV has been engineered to deliver genes of interest by deleting the internal non-repeating portion of the AAV genome and inserting a heterologous gene between the ITRs. The heterologous gene may be functionally linked to a heterologous promoter (constitutive, cell-specific, or inducible) capable of driving gene expression in target cells. To produce infectious recombinant AAV (rAAV) containing a heterologous gene, a suitable producer cell line is transfected with a rAAV vector containing a heterologous gene. The producer cell is concurrently transfected with a second plasmid harboring the AAV rep and cap genes under the control of their respective endogenous promoters or heterologous promoters. Finally, the producer cell is infected with a helper virus.

Once these factors come together, the heterologous gene is replicated and packaged as though it were a wild-type AAV genome. When target cells are infected with the resulting rAAV virions, the heterologous gene enters and is expressed in the target cells. Because the target cells lack the rep and cap genes and the adenovirus helper genes, the rAAV cannot further replicate, package or form wild-type AAV.

The use of helper virus, however, presents a number of problems. First, the use of adenovirus in a rAAV production system causes the host cells to produce both rAAV and infectious adenovirus. The contaminating infectious adenovirus can be inactivated by heat treatment (56° C. for 1 hour). Heat treatment, however, results in approximately a 50% drop in the titer of functional rAAV virions. Second, varying amounts of adenovirus proteins are present in these preparations. For example, approximately 50% or greater of the total protein obtained in such rAAV virion preparations is free adenovirus fiber protein. If not completely removed, these adenovirus proteins have the potential of eliciting an immune response from the patient. Third, AAV vector production methods which employ a helper virus require the use and manipulation of large amounts of high titer infectious helper virus, which presents a number of health and safety concerns, particularly in regard to the use of a herpesvirus. Fourth, concomitant production of helper virus particles in rAAV virion producing cells diverts large amounts of host cellular resources away from rAAV virion production, potentially resulting in lower rAAV virion yields.

Lentiviral Vectors. Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx.

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

Lentiviral vectors are known in the art, see Naldini et al., (1996); Zufferey et al., (1997); U.S. Pat. Nos. 6,013,516; and 5,994,136. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest.

Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene, such as the STAT-1α gene in this invention, into that packaging cell yields a producer cell which releases infectious viral particles carrying the foreign gene of interest. The env preferably is an amphotropic envelope protein which allows transduction of cells of human and other species.

One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

The vector providing the viral env nucleic acid sequence is associated operably with regulatory sequences, e.g., a promoter or enhancer. The regulatory sequence can be any eukaryotic promoter or enhancer, including for example, the Moloney murine leukemia virus promoter-enhancer element, the human cytomegalovirus enhancer or the vaccinia P7.5 promoter. In some cases, such as the Moloney murine leukemia virus promoter-enhancer element, the promoter-enhancer elements are located within or adjacent to the LTR sequences.

The heterologous or foreign nucleic acid sequence, such as the STAT-1α encoding polynucleotide sequence herein, is linked operably to a regulatory nucleic acid sequence. Preferably, the heterologous sequence is linked to a promoter, resulting in a chimeric gene. The heterologous nucleic acid sequence may also be under control of either the viral LTR promoter-enhancer signals or of an internal promoter, and retained signals within the retroviral LTR can still bring about efficient expression of the transgene. Marker genes may be utilized to assay for the presence of the vector, and thus, to confirm infection and integration. The presence of a marker gene ensures the selection and growth of only those host cells which express the inserts. Typical selection genes encode proteins that confer resistance to antibiotics and other toxic substances, e.g., histidinol, puromycin, hygromycin, neomycin, methotrexate, etc., and cell surface markers.

The vectors are introduced via transfection or infection into the packaging cell line. The packaging cell line produces viral particles that contain the vector genome. Methods for transfection or infection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with a dominant selectable marker, such as neo, DHFR, Gln synthetase or ADA, followed by selection in the presence of the appropriate drug and isolation of clones. The selectable marker gene can be linked physically to the packaging genes in the construct.

Lentiviral transfer vectors Naldini et al. (1996), have been used to infect human cells growth-arrested in vitro and to transduce neurons after direct injection into the brain of adult rats. The vector was efficient at transferring marker genes in vivo into the neurons and long term expression in the absence of detectable pathology was achieved. Animals analyzed ten months after a single injection of the vector showed no decrease in the average level of transgene expression and no sign of tissue pathology or immune reaction (Blomer et al., 1997). Thus, in the present invention, one may graft or transplant cells infected with the recombinant lentivirus ex vivo, or infect cells in vivo.

Other Viral Vectors. The development and utility of viral vectors for gene delivery is constantly improving and evolving. Other viral vectors such as poxvirus; e.g., vaccinia virus (Gnant et al., 1999; Gnant et al., 1999), alpha virus; e.g., sindbis virus, Semliki forest virus (Lundstrom, 1999), reovirus (Coffey et al., 1998) and influenza A virus (Neumann et al., 1999) are contemplated for use in the present invention and may be selected according to the requisite properties of the target system.

In certain embodiments, vaccinia viral vectors are contemplated for use in the present invention. Vaccinia virus is a particularly useful eukaryotic viral vector system for expressing heterologous genes. For example, when recombinant vaccinia virus is properly engineered, the proteins are synthesized, processed and transported to the plasma membrane. Vaccinia viruses as gene delivery vectors have recently been demonstrated to transfer genes to human tumor cells, e.g., EMAP-II (Gnant et al., 1999), inner ear (Derby et al., 1999), glioma cells, e.g., p53 (Timiryasova et al., 1999) and various mammalian cells, e.g., P-450 (U.S. Pat. No. 5,506,138). The preparation, growth and manipulation of vaccinia viruses are described in U.S. Pat. No. 5,849,304 and U.S. Pat. No. 5,506,138 (each specifically incorporated herein by reference).

In other embodiments, sindbis viral vectors are contemplated for use in gene delivery. Sindbis virus is a species of the alphavirus genus (Garoff and Li, 1998) which includes such important pathogens as Venezuelan, Western and Eastern equine encephalitis viruses (Sawai et al., 1999; Mastrangelo et al., 1999). In vitro, sindbis virus infects a variety of avian, mammalian, reptilian, and amphibian cells. The genome of sindbis virus consists of a single molecule of single-stranded RNA, 11,703 nucleotides in length. The genomic RNA is infectious, is capped at the 5' terminus and polyadenylated at the 3' terminus, and serves as mRNA. Translation of a vaccinia virus 26S mRNA produces a polyprotein that is cleaved co-and post-translationally by a combination of viral and presumably host-encoded proteases to give the three virus structural proteins, a capsid protein (C) and the two envelope glycoproteins (E1 and PE2, precursors of the virion E2).

Three features of sindbis virus suggest that it would be a useful vector for the expression of heterologous genes. First, its wide host range, both in nature and in the laboratory. Second, gene expression occurs in the cytoplasm of the host cell and is rapid and efficient. Third, temperature-sensitive mutations in RNA synthesis are available that may be used to modulate the expression of heterologous coding sequences by simply shifting cultures to the non-permissive temperature at various time after infection. The growth and maintenance of sindbis virus is known in the art (U.S. Pat. No. 5,217,879, specifically incorporated herein by reference).

Chimeric Viral Vectors. Chimeric or hybrid viral vectors are being developed for use in therapeutic gene delivery and are contemplated for use in the present invention. Chimeric poxyiral/retroviral vectors (Holzer et al., 1999), adenoviral/retroviral vectors (Feng et al., 1997; Bilbao et al., 1999; Caplen et al., 1999) and adenoviral/adeno-associated viral vectors (Fisher et al., 1996; U.S. Pat. No. 5,871,982) have been described.

These "chimeric" viral gene transfer systems can exploit the favorable features of two or more parent viral species. For example, Wilson et al., provide a chimeric vector construct which comprises a portion of an adenovirus, AAV 5' and 3' ITR sequences and a selected transgene, described below (U.S. Pat. No. 5,871,983, specifically incorporate herein by reference).

The adenovirus/AAV chimeric virus uses adenovirus nucleic acid sequences as a shuttle to deliver a recombinant AAV/transgene genome to a target cell. The adenovirus nucleic acid sequences employed in the hybrid vector can range from a minimum sequence amount, which requires the use of a helper virus to produce the hybrid virus particle, to only selected deletions of adenovirus genes, which deleted gene products can be supplied in the hybrid viral production process by a selected packaging cell. At a minimum, the adenovirus nucleic acid sequences employed in the pAdA shuttle vector are adenovirus genomic sequences from which all viral genes are deleted and which contain only those adenovirus sequences required for packaging adenoviral genomic DNA into a preformed capsid head. More specifically, the adenovirus sequences employed are the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. The adenovirus sequences may be modified to contain desired deletions, substitutions, or mutations, provided that the desired function is not eliminated.

The AAV sequences useful in the above chimeric vector are the viral sequences from which the rep and cap polypeptide encoding sequences are deleted. More specifically, the AAV sequences employed are the cis-acting 5' and 3' inverted terminal repeat (ITR) sequences. These chimeras are characterized by high titer transgene delivery to a host cell and the ability to stably integrate the transgene into the host cell chromosome (U.S. Pat. No. 5,871,983, specifically incorporate herein by reference). In the hybrid vector construct, the AAV sequences are flanked by the selected adenovirus sequences discussed above. The 5' and 3' AAV ITR sequences themselves flank a selected transgene sequence and associated regulatory elements, described below. Thus, the sequence formed by the transgene and flanking 5' and 3' AAV sequences may be inserted at any deletion site in the adenovirus sequences of the vector. For example, the AAV sequences are desirably inserted at the site of the deleted E1a/E1b genes of the adenovirus. Alternatively, the AAV sequences may be inserted at an E3 deletion, E2a deletion, and so on. If only the adenovirus 5' ITR/packaging sequences and 3' ITR sequences are used in the hybrid virus, the AAV sequences are inserted between them.

The transgene sequence of the vector and recombinant virus can be a gene, a nucleic acid sequence or reverse transcript thereof, heterologous to the adenovirus sequence, which encodes a protein, polypeptide or peptide fragment of interest. The transgene is operatively linked to regulatory components in a manner which permits transgene transcription. The composition of the transgene sequence will depend upon the use to which the resulting hybrid vector will be put. For example, one type of transgene sequence includes a therapeutic gene which expresses a desired gene product in a host cell. These therapeutic genes or nucleic acid sequences typically encode products for administration and expression in a patient in vivo or ex vivo to replace or correct an inherited or non-inherited genetic defect or treat an epigenetic disorder or disease.

(x) Non-Viral Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

Injection. In certain embodiments, a nucleic acid may be delivered to an organelle, a cell, a tissue or an organism via one or more injections (i.e., a needle injection), such as, for example, either subcutaneously, intradermally, intramuscularly, intervenously or intraperitoneally. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into Xenopus oocytes (Harland and Weintraub, 1985).

Electroporation. In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Calcium Phosphate. In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

DEAE-Dextran: In another embodiment, a nucleic acid is delivered into a cell using DEAE-dextran followed by polyethylene glycol. In this manner, reporter plasmids were introduced into mouse myeloma and erythroleukemia cells (Gopal, 1985).

Sonication Loading. Additional embodiments of the present invention include the introduction of a nucleic acid by direct sonic loading. LTK⁻ fibroblasts have been transfected with the thymidine kinase gene by sonication loading (Fechheimer et al., 1987).

Liposome-Mediated Transfection. In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

Receptor-Mediated Transfection. Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

F. Expression Systems

Numerous prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'S COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented.

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk–, hgprt– or aprt– cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

G. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

H. Cell Propagation

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth). Non-anchorage dependent or suspension cultures from continuous established cell lines are the most widely used means of large scale production of cells and cell products. However, suspension cultured cells have limitations, such as tumorigenic potential and lower protein production than adherent T-cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Non-ionic salts are preferred, since other agents such as bile salts, precipitate at acid pH or in the presence of bivalent cations. Antibodies are and their uses are discussed further, below.

III. Generating Antibodies Reactive with Notch3

In another aspect, the present invention contemplates an antibody that is immunoreactive with a Notch3 molecule of the present invention, or any portion thereof. In particular, the invention contemplates using peptides having the sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8, optionally linked together or linked to a carrier molecule such as keyhole limpet hemocyanin (KLH) and bovine serum albumin (BSA). An antibody can be a polyclonal or a monoclonal antibody. In a preferred embodiment, an antibody is a monoclonal antibody. Means for preparing and characterizing antibodies are well known in the art (see, e.g., Harlow and Lane, 1988).

Briefly, a polyclonal antibody is prepared by immunizing an animal with an immunogen comprising a polypeptide, of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to Notch3-related antigen epitopes. Additionally, it is proposed that monoclonal antibodies specific to the particular Notch3 of different species may be utilized in other useful applications In general, both polyclonal and monoclonal antibodies against Notch3 may be used in a variety of embodiments. For example, they may be employed in antibody cloning protocols to obtain cDNAs or genes encoding other Notch3. They may also be used in inhibition studies to analyze the effects of Notch3 related peptides in cells or animals. Anti-Notch3 antibodies will also be useful in immunolocalization studies to analyze the distribution of Notch3 during various cellular events, for example, to determine the cellular or tissue-specific distribution of Notch3 polypeptides under different points in the cell cycle. A particularly useful application of such antibodies is in purifying native or recombinant Notch3, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are give in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196, 265, incorporated herein by reference. Typically, this technique involves immunizing a suitable animal with a selected immunogen composition, e.g., a purified or partially purified Notch3 protein, polypeptide or peptide or cell expressing high levels of Notch3. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 41, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

IV. Methods of Therapy

The present invention also involves, in another embodiment, the treatment of cancer. The types of cancer that may be treated, according to the present invention, is limited only by the involvement of Notch3. By involvement, it is not even a requirement that Notch3 be mutated or abnormal—the overexpression of this tumor suppressor may actually overcome other lesions within the cell. Thus, it is contemplated that a wide variety of tumors may be treated using Notch3 therapy, including cancers of the brain, lung, liver, spleen, kidney, lymph node, pancreas, small intestine, blood cells, colon, stomach, breast, endometrium, prostate, testicle, ovary, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

A. Peptide Therapy

Another therapy approach is the provision, to a subject, of Notch3 polypeptide, fragments, synthetic peptides, mimetics or other analogs thereof. The protein/peptide may be produced by recombinant expression means or, if small enough, generated by an automated peptide synthesizer. Formulations would be selected based on the route of administration and purpose including, but not limited to, liposomal formulations and classic pharmaceutical preparations.

B. Antibody Therapy

Applicants also contemplate the use of antibodies to Notch3, in particular, to epitopes comprised in or represented by SEQ ID NO:1, SEQ ID NO:2, SEQ ID NO:3, SEQ ID NO:4, SEQ ID NO:5, SEQ ID NO:6, SEQ ID NO:7, or SEQ ID NO:8. Antibodies will be administered according to standard protocols for passive immunotherapy. Administration protocols would generally involve intratumoral, local or regional (to the tumor) administration, as well as systemic administration.

In addition, the antibody reagent may be altered, such that it will have one or more improved properties. The antibody may be recombinant, i.e., an antibody gene cloned into an expression cassette which is then introduced into a cell in which the antibody gene was not initially created. The antibody may be single chain, a fragment (Fab, Fv, Vh, ScFv), chimeric or humanized.

C. Combined Therapies with Immunotherapy, Traditional Chemo- or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that Notch3 peptide or antibody therapy could be used similarly in conjunction with chemo- or radiotherapeutic intervention. It also may prove effective to combine a Notch3-directed therapy with another cancer therapy.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with a Notch3 peptide or antibody and at least one other agent. These compositions would be provided in a combined amount effective to kill or inhibit proliferation of the cell. This process may involve contacting the cells with a Notch3 peptide or antibody and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the Notch3 peptide or antibody therapy treatment may precede or follow the other agent treatment by intervals ranging from minutes to weeks. In embodiments where the other agent and expression construct are applied separately to the cell, one would generally ensure that a significant period of time did not expire between the time of each delivery, such that the agent and a Notch3 peptide or antibody would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either Notch3 peptide or antibody or the other agent will be desired. Various combinations may be employed, where Notch3 (peptide or antibody) is "A" and the other agent is "B", as exemplified below:

A/B/A B/A/B B/B/A A/A/B B/A/A A/B/B B/B/B/A

B/B/A/B A/A/B/B A/B/A/B A/B/B/A B/B/A/A B/A/B/A

B/A/A/B B/B/B/A A/A/A/B B/A/A/A A/B/A/A A/A/B/A

A/B/B/B B/A/B/B B/B/A/B

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with a Notch3 expression construct is particularly preferred as this compound.

In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with a Notch3 expression construct, as described above.

Agents that directly cross-link nucleic acids, specifically DNA, are envisaged to facilitate DNA damage leading to a synergistic, antineoplastic combination with Notch3. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the local or regional delivery of Notch3 expression constructs to patients with cancer will be a very efficient method for treating the clinical disease. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining Notch3 therapies with chemo- and radiotherapies, it also is contemplated that combination with other gene therapies will be advantageous. For example, targeting of Notch3 and p53 mutations at the same time may produce an improved anti-cancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf erb, src, fms, jun, trk, ret, gsp, hst, bcl and abl.

It also should be pointed out that any of the foregoing therapies may prove useful by themselves in treating a Notch3. In this regard, reference to chemotherapeutics and non-Notch3 gene therapy in combination should also be read as a contemplation that these approaches may be employed separately.

D. Formulations and Routes for Administration to Patients

Where clinical applications are contemplated, it will be necessary to prepare pharmaceutical compositions—a Notch3 peptide, or antibody—in a form appropriate for the intended application. Generally, this will entail preparing compositions that are essentially free of pyrogens, as well as other impurities that could be harmful to humans or animals.

One will generally desire to employ appropriate salts and buffers to render delivery compositions stable and allow for uptake by target cells. Aqueous compositions of the present invention comprise an effective amount of the Notch3 peptide or antibody to cells/a subject, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the Notch3 peptides or antibodies of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Notch3 Is Expressed in Resected Human Lung Cancers. The clinical relevance of a pathway to tumorigenesis often depends on the prevalence of its dysregulation. To begin to assess the prevalence of Notch3 involvement in lung cancer, the inventors investigated the frequency of Notch3 overexpression in resected lung cancer. They used immunohistochemistry (IHC), with a characterized and validated Notch3 antibody recognizing the extracellular domain (Joutel et al., 2000), in resected lung tumor tissues. For this experiment, the inventors used tumor tissue arrays produced as part of the Vanderbilt SPORE initiative. When the Notch3 antibody targeting the extracellular domain was used, a pattern of cytoplasmic and membranous staining was observed in the representative adenocarcinoma and squamous cell carcincoma (FIG. 3, panel A and C). No staining was observed in a neuroendocrine tumor and normal lung tissue (panel B and D), suggesting that Notch3 dysregulation is specific to cancer. The staining was scored on a composite scale of 0 to 4 by two independent investigators, including one pathologist. No staining was scored 0, whereas slight positivity equivalent to background stain was scored as 1. Tumors that scored 2 or higher were considered positive. Fractional positivity was nearly 100% in many tumors with high Notch3 expression. Of the 207 resected tumors, 39% had high Notch3 expression (Table 7). Each tumor was represented in triplicate, and the final score per tumor was calculated by averaging the score of three samples.

TABLE 7

Expression of Notch3 and EGFr By IHC Using Microtissue Arrays

|  | N | Notch3+ n | Notch3+ % | EGFr+ n | EGFr+ % |
|---|---|---|---|---|---|
| Adenocarcinomas | 87 | 32 | 37% | 69 | 79% |
| Neuroendocrine |  |  |  |  |  |
| Carcinoid | 10 | 2 | 20% | 5 | 50% |
| Large Cell | 7 | 1 | 14% | 2 | 29% |
| Small Cell | 4 | 1 | 25% | 3 | 75% |
| Squamous Cell Carcinomas | 88 | 40 | 45% | 81 | 92% |
| Large Cell | 11 | 4 | 36% | 8 | 73% |
|  | 207 | 80 | 39% | 168 | 81% |

The frequency of Notch3 overexpression in lung tumors is higher than the frequency of HER2/neu (16%) and k-Ras mutations (16%), and comparable to EGFr (13-80%) (Hirsch et al., 2002; Rodenhuis et al., 1997; Meert et al., 2002). No information is available with regard to the frequency of overexpression of other members of the Notch family or their receptors in human lung carcinomas. The lack of high quality antibodies to the Notch receptors, Jagged1, and Delta-like-1, -3 and -4 makes it difficult to determine their frequency in fresh tumor tissues. In both *C. elegans* and *Drosophila*, the Notch pathway crosstalks with the EGF pathway in cell fate determination during development. The inventors thus examined the correlation between Notch3 and EGFr expression. The frequency of EGFr expression in our tumor tissue arrays was 81%. 19% of EGFr positive tumors are Notch3 negative, whereas 43% of EGFr positive tumors are also Notch3 positive ($p<0.0001$ using Pearson correlation coefficient) (Haruki et al., 2005). This highly statistical association suggests that the Notch and EGF pathways are cooperative in lung tumorigenesis.

Ectopic Notch3 Expression Inhibits Terminal Differentiation in Developing Lungs of Transgenic Mice. To evaluate the potential transforming activity of Notch3 in vivo, the inventors studied the effect of activated Notch3 using a lung-specific, human SP-C promoter (Glasser et al., 1991; Lardelli et al., 1996). The constitutively-activate Notch3 allowed the inventors to assess the effect of ectopic expression of Notch3 without depending on ligand expression in the epithelium, since Jagged1 expression becomes restricted to endothelium as the lung matures (Taichman et al., 2002). Furthermore, constitutive expression of Notch3 also better mimics the many dysregulated pathways observed in cancer. The inventors observed perinatal lethality, and thus no surviving animals expresses the N3IC transgene.

Because of the crucial role of the Notch family in development, expression of a constitutively active Notch3 transgene could potentially disturb normal lung development. Therefore, the transgenic mice were sacrificed prior to birth, at E18.5. Of the 182 embryos at E18.5 gestation collected from 32 pregnant mothers, 10 were transgenic, as determined by PCR and Southern blot analysis. The inventors observed altered lung morphogenesis, altered terminal sac morphology, and abnormally abundant mesenchyme, and no type I pneumocytes when compared with control mice (FIGS. 4A-D). Despite the important role of the Notch signaling pathway in vascular development, no alteration in vasculogenesis was observed in the transgenics using the PECAM-1 antibody (data not shown), suggesting that the mesenchymal differentiation was influenced by the abnormally developing epithelium, and not by alterations of angiogenesis. While the majority of cuboidal cells lining the peripheral airways are pneumocytes based on their TTF1 positivity, they failed to demonstrate markers of mature type II pneumocytes, such as surfactant proteins C and B, markers for Clara cells (Clara cells secretory protein), or neuroendocrine cells (calcitonin gene-related peptide) suggesting that they were immature type II cells (data not shown).

Thus, this transgenic model provides evidence that dysregulation of Notch3 signaling in the developing lung affects morphogenesis and terminal differentiation of the lung epithelium. Prenatal activation of Notch3 in the peripheral epithelium of the lung in our SP-C-N3IC mouse model leads to nonviable newborn pups, making it impossible to evaluate tumor progression. An inducible transgenic model that allows activation of Notch3 signaling in the postnatal period will be more effectively recapitulate the somatic activation of potential oncogenes observed in human lung cancer. This approach is part of the proposal in our R01 funding. Regardless, the ectopic expression of Notch3 appears to inhibit terminal differentiation of type I pneumocytes and results in metaplasia of the immature respiratory epithelium, supporting a potential role of Notch3 in lung cancer formation.

Notch3 Inhibition Inhibits the Tumor Phenotype. To test their hypothesis that Notch3 plays an important role in the pathogenesis of lung cancer, the inventors used the approach of uncoupling its ligand binding and signaling functions (Rebay et al., 1993). To inhibit Notch3 activation, the inventors created a dominant-negative (DN) construct. One characteristic feature of malignant transformation is the ability of tumor cells to proliferate in the absence of adhesion, as measured by the soft-agar assay for colony formation. The inventors demonstrated that inhibition of Notch3 signaling by the DN construct dramatically decreases the ability of HCC2429 and H460 to form colonies in soft agar (FIG. 5A). Furthermore, colonies formed by the DN clones are markedly smaller than those seen with the vector control (VC). Transformed cells often have a relaxed serum or growth factor requirement for proliferation in monolayer culture (Holley, 1975). In serum-free medium, the DN clones failed to proliferate when compared to the vector controls (FIG. 5B). In summary, these observations demonstrated that inhibiting the Notch pathway using DN constructs reduces the tumor phenotype, supporting an oncogenic role for Notch3 in lung cancer.

Figure 6:
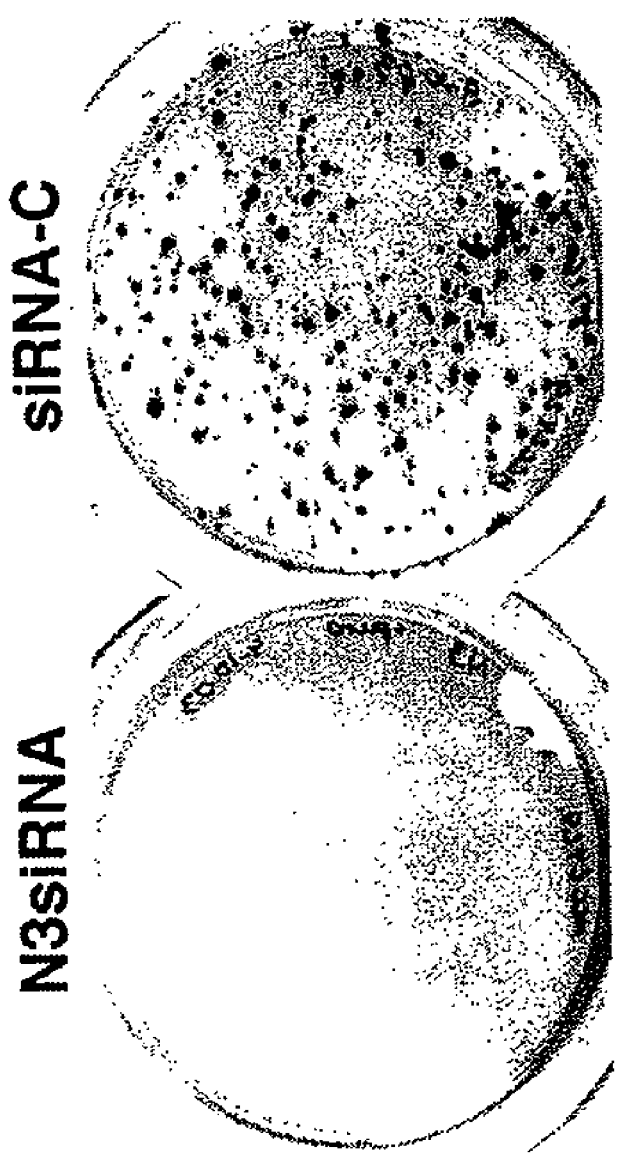
FIG. 6. Knocking out Notch3 with siRNA reduces focus formation. The pSuper vectors expressing Notch3 siRNA and a mouse Notch3 sequence were transfected into HCC2429, a human lung cancer cell line. The cells were selected with puramycin, then stained with crystal violet after 4 weeks.

Since Jagged1 is known to bind to other Notch receptors, it is possible that the antitumor effect observed when DN receptor is not Notch3-specific, since its mechanism of action is to sequester ligand (Shimizu et al., 2000). To determine whether specific inhibition of Notch3 activation can inhibit tumor phenotype, the inventors used siRNA to specifically knock down Notch3 expression. The inventors show that inhibiting Notch3 results in the lack of focus formation, further supporting the role of Notch3 in lung cancer pathogenesis (FIG. 6).

Figure 7:
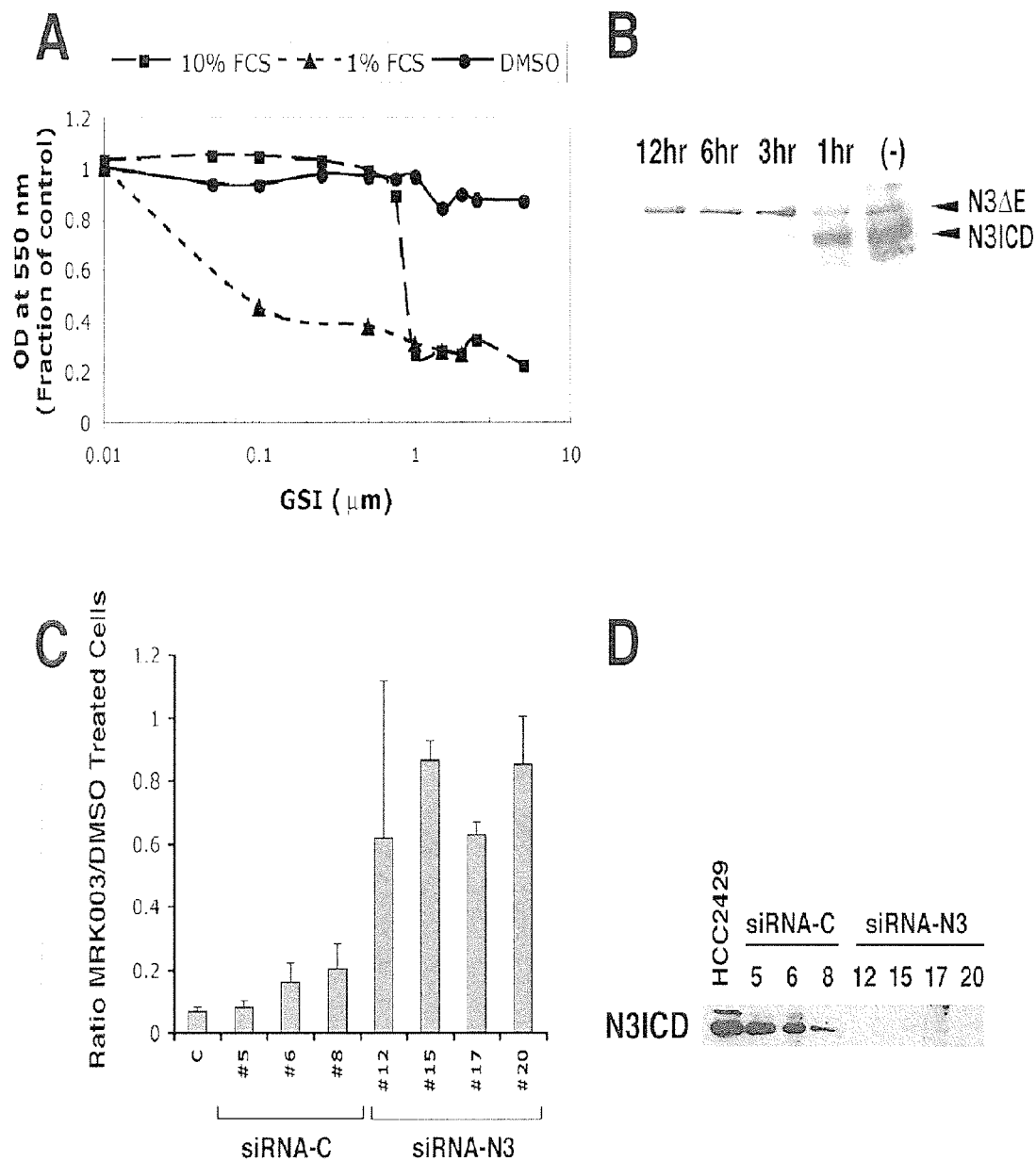
FIGS. 7A-D. A γ-secretase inhibitor inhibits tumor cells and Notch3 processing.
Figure 8:
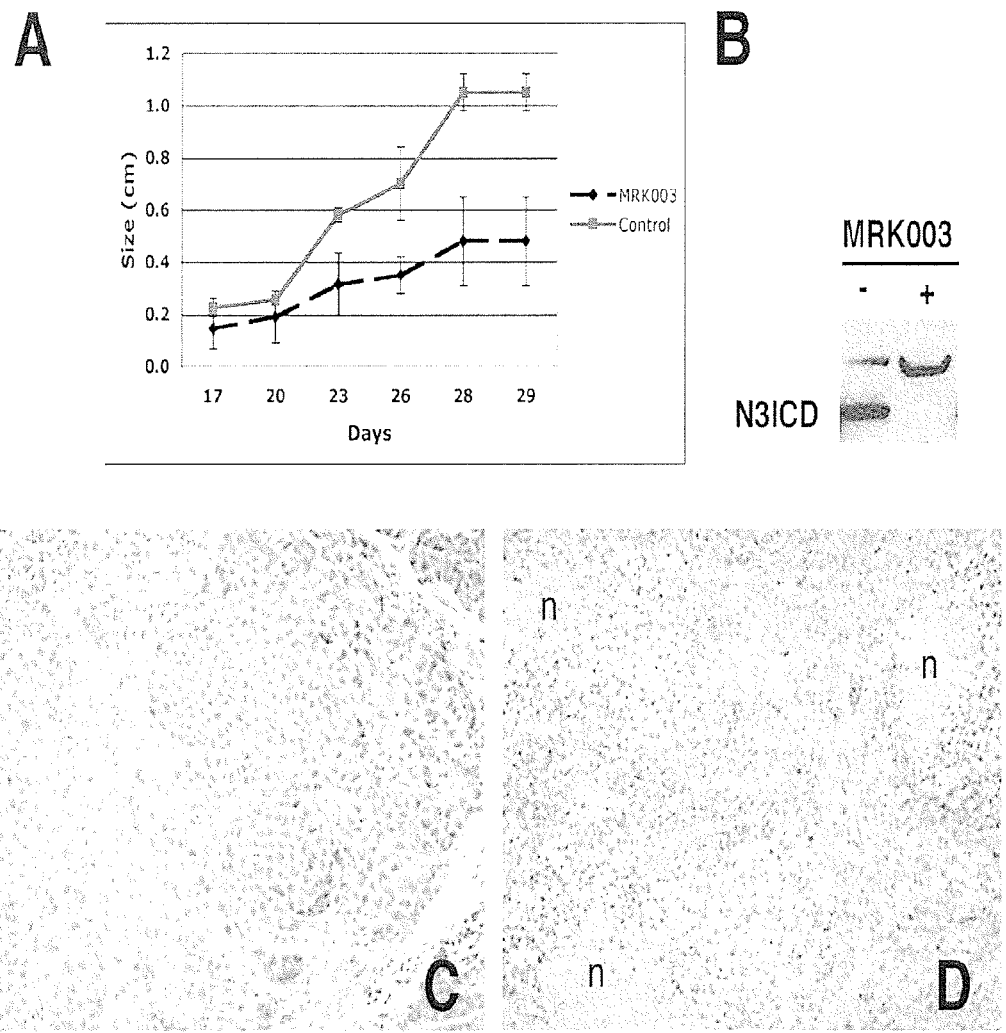
FIGS. 8A-D. γ-secretase inhibitor MRK003 demonstrates anti-tumor activity in vivo.

A γ-Secretase Inhibitor Reduces Proliferation in Lung Cancer Cells. Proteolytic processing of Notch receptors is required for activation. As previously described, three proteolytic cleavage sites are involved in enabling Notch signaling. In the final step, the membrane-associated Notch fragment is cleaved within its transmembrane domain by a γ-secretase-containing protein complex. Mammalian presenilins (PS-1 and PS-2) are polytopic transmembrane proteins that appear to function as aspartyl proteases within a multiprotein, γ-secretase complex (Wolfe and Kopan, 2004). Presenilins provide the active site of the proteolytic activity. This last cleavage releases the Notch intracellular domain, initiating CBF-1-mediated signaling. Thus, pharmacologic intervention that inhibits the activity of the γ-secretase proteases can potentially inhibit tumor growth in Notch-dependent cancer. Interestingly, at the same time that presenilins were shown to be essential for Notch signaling, they were discovered as susceptibility loci for Alzheimer's disease (Levitan and Greenwald, 1995). The pathogenesis of Alzheimer's disease is believed to be the accumulation of amyloid β-peptide (Aβ), which is derived from proteolytic processing of the β-amyloid precursor protein (APP) by β- and γ-secretases. Since inhibition of the Notch3 pathway using the DN construct resulted in the loss of the tumor phenotype, the inventors wanted to examine the effect of γ-secretase inhibitors on tumor growth. The inventors treated HCC2429 cells with GSI (Gamma Secretase Inhibitor), a commercially available γ-secretase inhibitor (Calbiochem). The inventors observed that GSI inhibits tumor proliferation with an $IC_{50}$ of about 1 μM in comparison to DMSO (FIG. 7A). However, in the presence of low serum the inhibition increases almost 1 log. This finding is similar to what was observed when the DN construct was used in HCC2429. This observation suggests that the antiproliferative activity observed is Notch-dependent. The inventors also observed inhibition of proliferation in other lung cancer cell lines expressing Notch3 (data not shown). Biochemically, treatment with these inhibitors also resulted in the loss of activated Notch3, as measured by the levels of the N3ICD (FIG. 7B). Stable expression of Notch3 siRNA also leads to loss of sensitivity to γ-secretase inhibition (FIGS. 7C, 7D).

To assess the effect of pharmacologically inhibiting Notch activation in vivo, the inventors treated subcutaneous xenografts with MRK003, a γ-secretase inhibitor from Merck, Inc. & Co. Based on the manufacturer's recommended dose, the mice were treated with 100 mg/kg orally for 3 consecutives days per week once the tumors were palpable. At the end of a 2-week treatment, the animals were then euthanized, and the tumors were harvested. A reduction of tumor size was seen in animals treated with the inhibitor, with a concomitant reduction in activated Notch3 (N3ICD) (FIGS. 8A-D).

Figure 9:
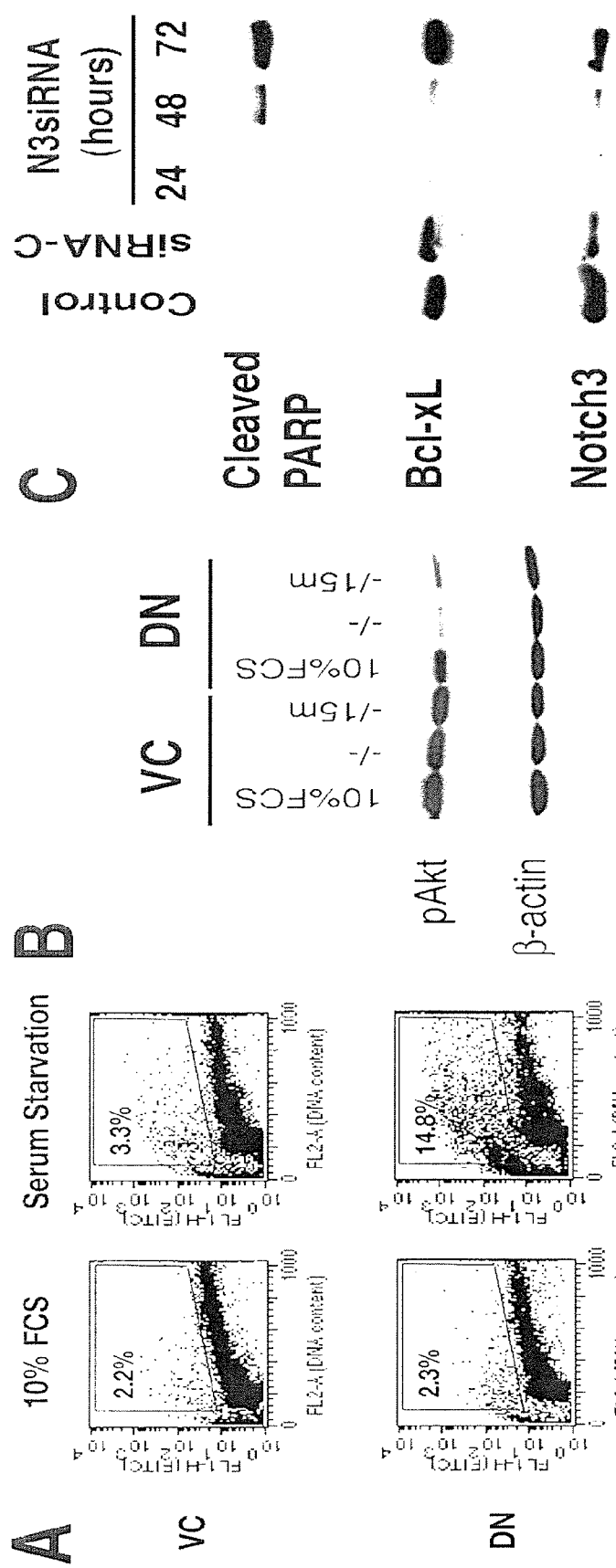
FIGS. 9A-C. Inhibition of Notch3 increases apoptosis.

Notch3 Inhibition Induces Apoptosis. One hallmark of cancer is resistance to apoptosis. Genetic and pharmacologic inhibition of the Notch pathway in other tumors has been shown to induce apoptosis (Qin et al., 2004; Curry et al., 2005; Shelly et al., 1999). The inventors examined whether inhibiting the Notch3 pathway can induce apoptosis. The inventors noted that in the HCC2429 clone expressing the dominant-negative receptor, the inhibition of the Notch3 pathway appears to render the tumor cells sensitive to apoptosis in the presence of serum starvation compared to vector control (FIG. 9A). One mechanism of apoptosis induction is the down-regulation of Akt phosphorylation. FIG. 9B shows that the level of phosphorylated Akt does indeed decrease when the DN Notch3 construct is used. The inventors also demonstrated that inhibition of Notch3 using siRNA results in the down-regulation of Bcl-xL (24 and 48 hours) and enhances the upregulation of cleaved PARP (48 hours), suggesting that Notch3 plays and important role in tumor survival (FIG. 9C).

Figure 10:
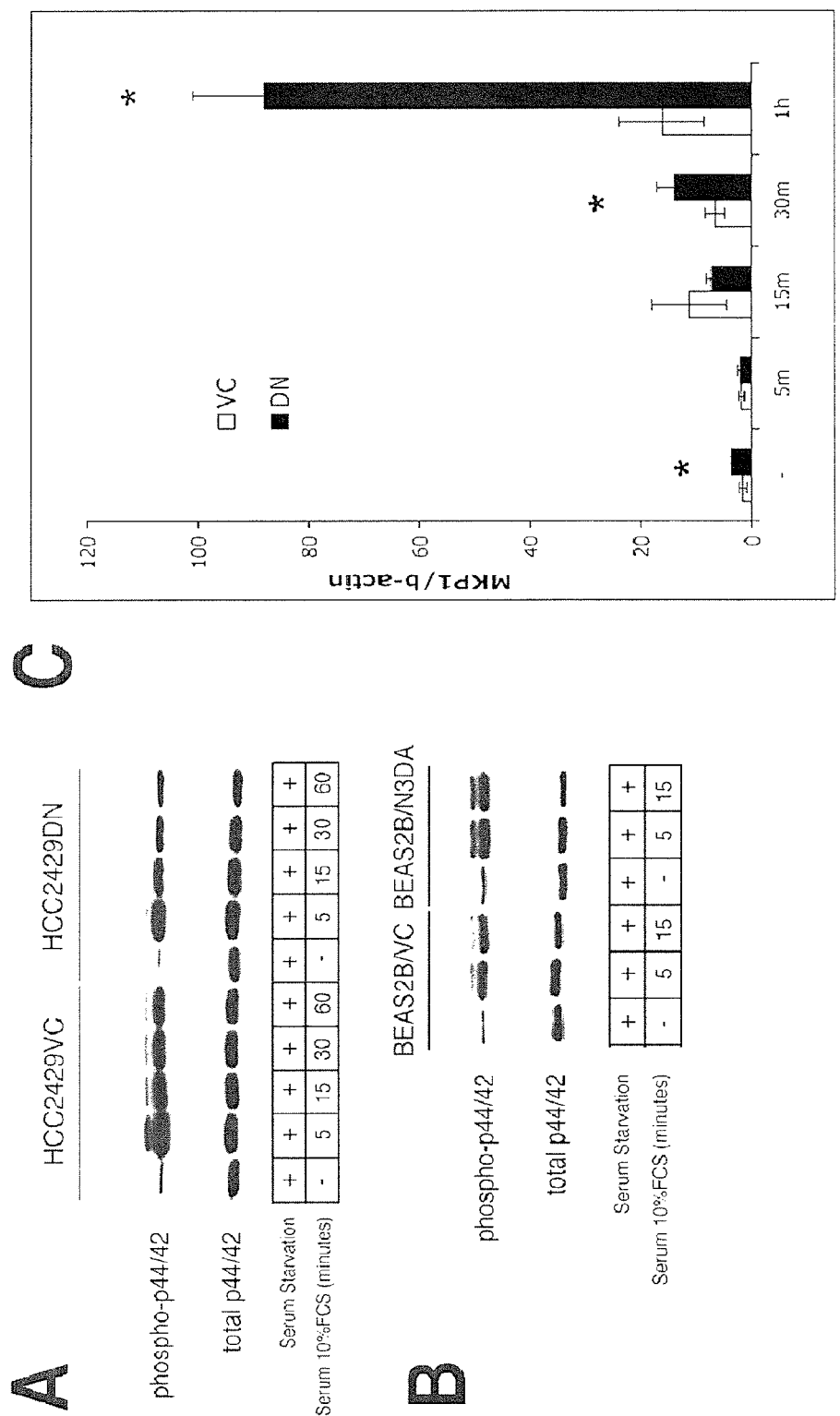
FIGS. 10A-C. Notch3 crosstalks with the MAPK pathway.

Notch3 Crosstalks with the MAPK Pathway. In mammals, Notch receptors signal primarily by binding to CBF-1 and related transcription co-activators. However, as mentioned previously, the Notch and EGF/MAPK pathways are known to interact in developing vertebrates and invertebrates. Thus, since the MAPK pathway, and in particular the ERK subfamily, also plays a prominent role in cellular response to growth factors, and is often altered in cancer, The inventors examined whether Notch3 alters ERK signaling in lung cancer cells. Using the DN receptor, they showed that inhibiting Notch3 downregulates MAPK, and conversely, that MAPK is upregulated when the cells were transfected with activated Notch3 intracellular domain (FIGS. 10A, 10B). Moreover, lower levels of activated MAPK (p44/p42) expression in the unstimulated DN clones and a markedly higher level of activation with growth factor induction in the VC in comparison to the DN clone suggest that the disruption of the Notch3 signaling pathway renders lung cancer cells more resistant to growth-factor-dependent MAPK activation. This observation has been confirmed in two other lung cancer cell lines, H460 and H1819, transfected with the DN construct.

Interestingly, with prolonged exposure to serum (60 minutes), the HCC2429 clone expressing the dominant-negative construct shows that p44/p42 phosphorylation was attenuated significantly compared to vector control (FIG. 10A). Prolonged exposure to growth factors and activation of the p44/p42 cascade can induce the expression of MAPK phosphatases-1 and -2 (MKP-1/-2) as part of a negative feedback loop and result in the down-regulation of the MAPK pathway (Traverse et al., 1992; Plows et al., 2002; Haneda et al., 1999; Brondello et al., 1997). Down-regulation of MKPs or resistance to dephosphorylation by MKPs are often observed in human tumors, and Notch3 may have a role in suppressing MKP expression (Sivaraman et al., 1997; Magi-galluzzi et al., 1997; Barry et al., 2001). Recent data demonstrate that one mechanism by which Notch antagonizes EGF in developing *C. elegans* is the upregulation of LIP-1, a homolog of mammalian MAPK phosphatases (Berset et al., 2001). Since *Drosophila* and *C. elegans* Notch have the highest homology to human Notch1, and Notch3 appears to antagonize Notch1, it follows that Notch3 might suppress MAPK phosphatase expression in cancer cells. To test this hypothesis, the inventors quantitated the level of MKP-1 using real-time PCR following serum induction in HCC2429 stably transfected with DN and VC. Higher levels of MKP-1 were observed in the DN clones (FIG. 10C). This finding suggests that Notch3 also modulates MAPK activation through MKP-1 transcriptional control.

Figure 11:
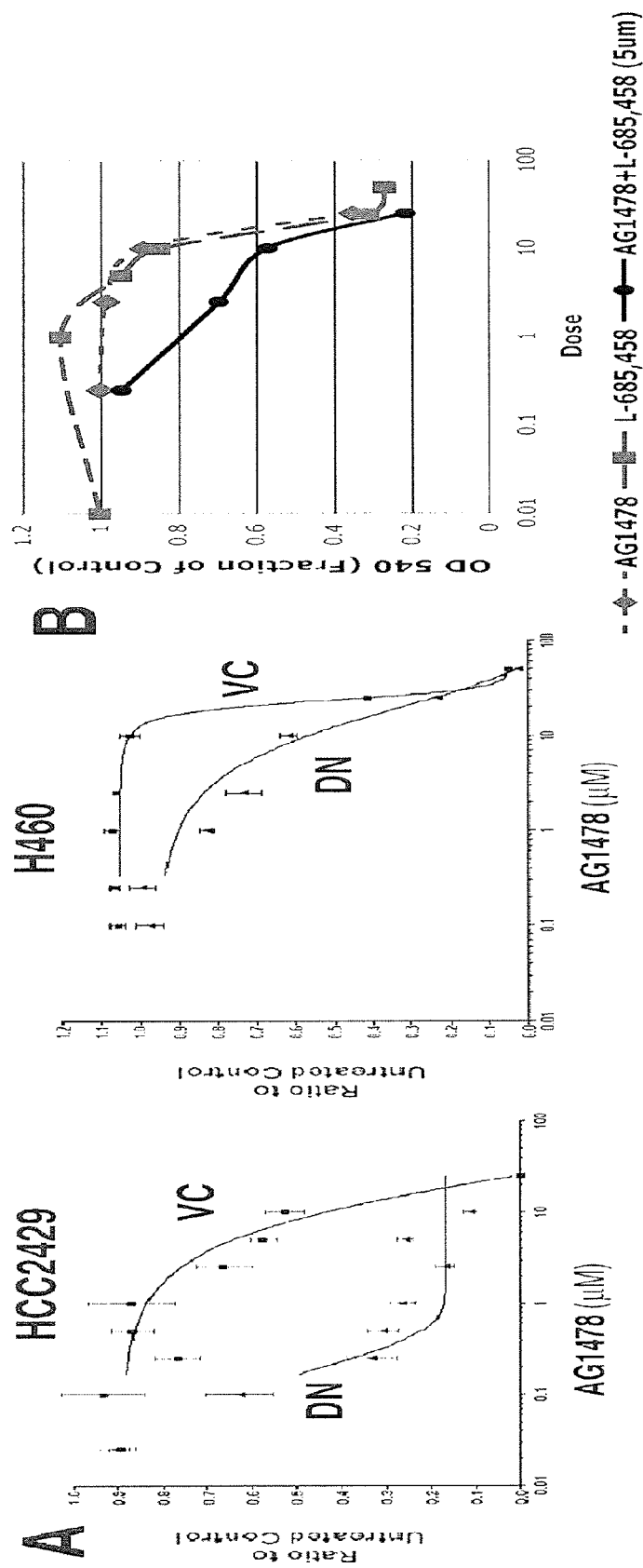
FIGS. 11A-B. Notch3 modulates the EGF pathway and increases sensitivity to an EGFr inhibitor.
Figure 12:
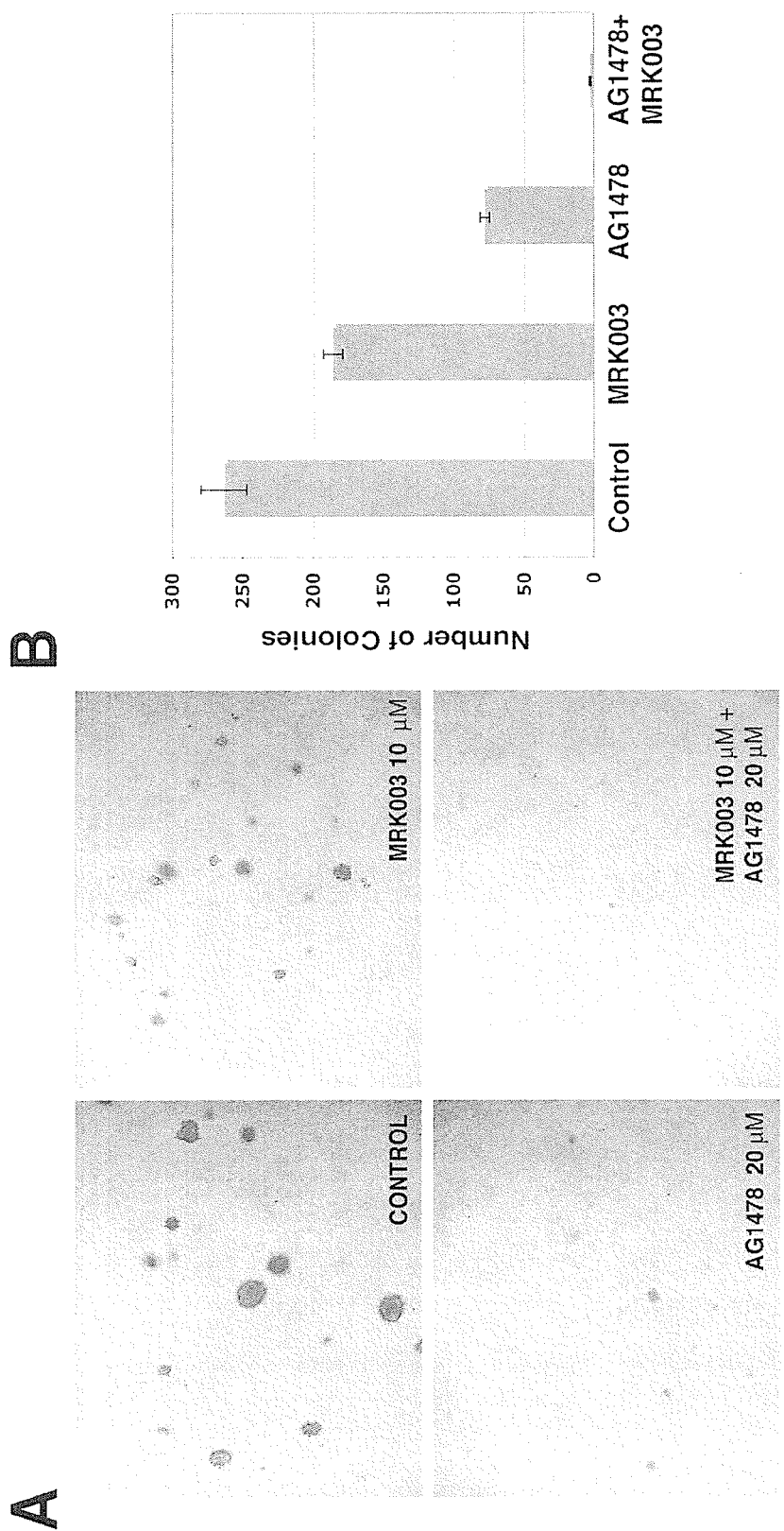
FIGS. 12A-B. In HCC2429 lung cancer cell line, Notch inhibitor MRK003 enhances the effect of EGFR inhibitor AG1478 on colony formation in soft agar.

EGFr Inhibitors Enhance the Anti-proliferation Effect of Notch3 Inhibition. The inventors previously showed that Notch3 expression positively correlates with EGFR expression in our tumor tissue array. The also showed that Notch3 cooperates with the MAPK pathway. Based on existing literature and their observations, the inventors hypothesized that Notch3 acts synergistically with the EGFR pathway in the promotion and the survival of lung cancer cells and that combining inhibitors of both pathways will have synergistic therapeutic value. To test this hypothesis, the inventors examined whether inhibiting the Notch3 pathway increases tumor inhibition when lung cancer cells are treated with an EGFR tyrosine kinase inhibitor, AG1478. When HCC2429 cells were maintained in EGF-supplemented media and treated with increasing doses of AG1478, the clones transfected with the DN construct showed a 40-fold increase in sensitivity to EGFR inhibitors, that is, the $IC_{50}$ was reduced from 8.3 µM to 0.2 µM (FIG. 11A). In H460, a lung cancer cell line that has lower Notch3 expression as well as a k-Ras mutation (data not shown) and is more resistant to AG1478 ($IC_{50}$ of 23.8 µM), the inhibition of the Notch3 pathway also reduces cancer cell survival by approximately two-fold ($IC_{50}$ of 12.1 µM, FIG. 10A). These data provide evidence that Notch3 activation may decrease a tumor's dependence on the EGF pathway and thus further decrease the sensitivity to EGFR tyrosine kinase inhibitors. Synergism can also be observed when the γ-secretase inhibitor L-685,458 is added to AG1478 (FIG. 11B). Using the soft-agar colony assay, the inventors also demonstrate additive effects by combining MRK003, another γ-secretase inhibitor, with an EGFR inhibitor (FIGS. 12A, 12B). From a therapeutic standpoint, Notch3 is a good target for therapeutic intervention both alone and in combination with growth factor receptor inhibitors. Since about 80% of lung carcinomas express EGFR, but far fewer respond to kinase inhibition, our data suggest that adding a Notch3 inhibitor will improve the response rate in patients treated with EGFR inhibitors.

Figure 13:
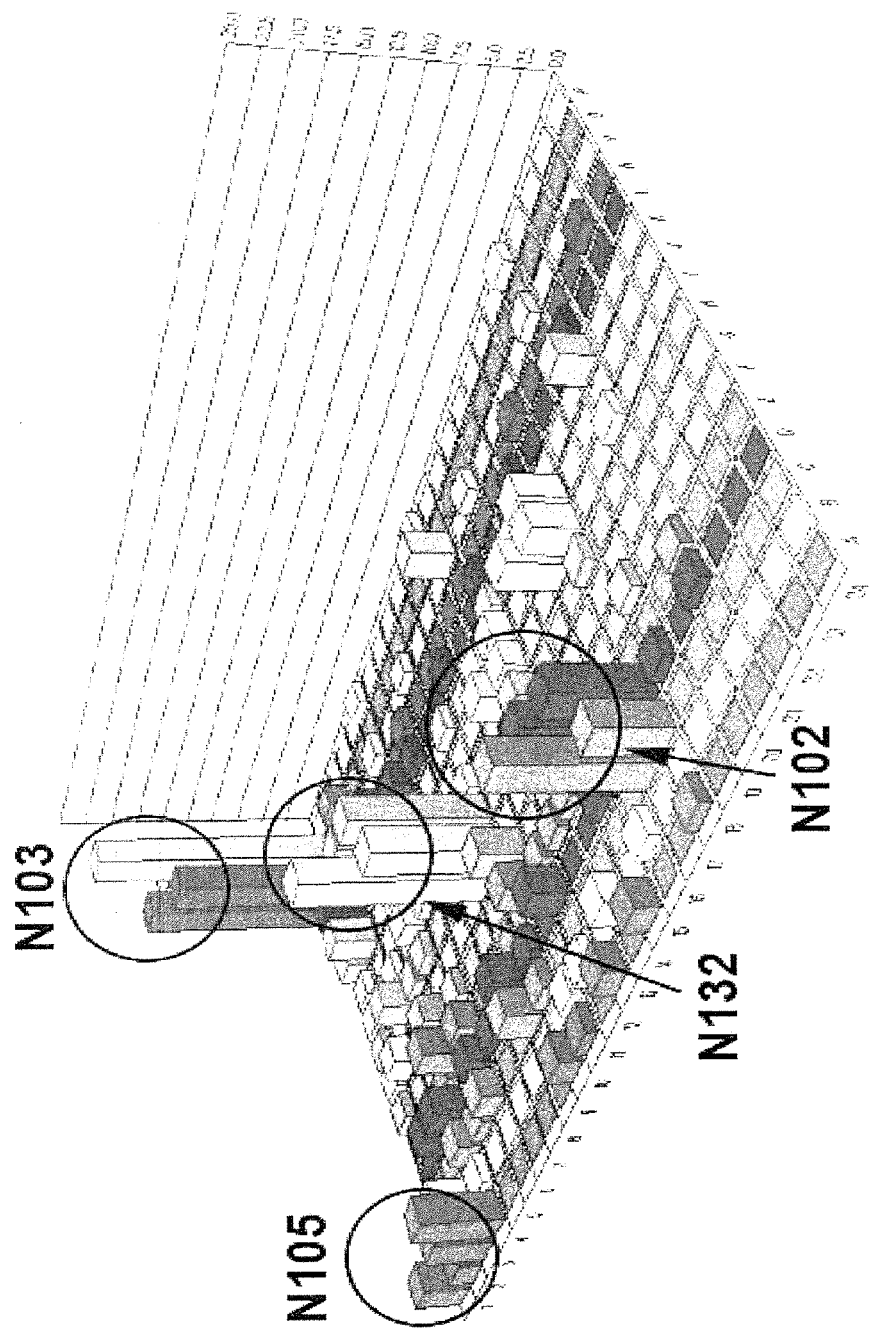
FIG. 13. Notch3 peptides induce apoptosis. Representative experiment showing that the peptides induce apoptosis by Annexin V staining through screening using an FMAT system. Each of 155 different peptides were assayed in quadruplicate, and only those peptides that produced a significant increase of fluorescence signal in all 4 wells were considered potentially positive or capable of inducing apoptosis. The bar graphs here reflect fluorescence counts. Sequences N102: CATAV, N103: CFHGAT, N105: CVSNP, N132: CLNGGS.
Figure 14:
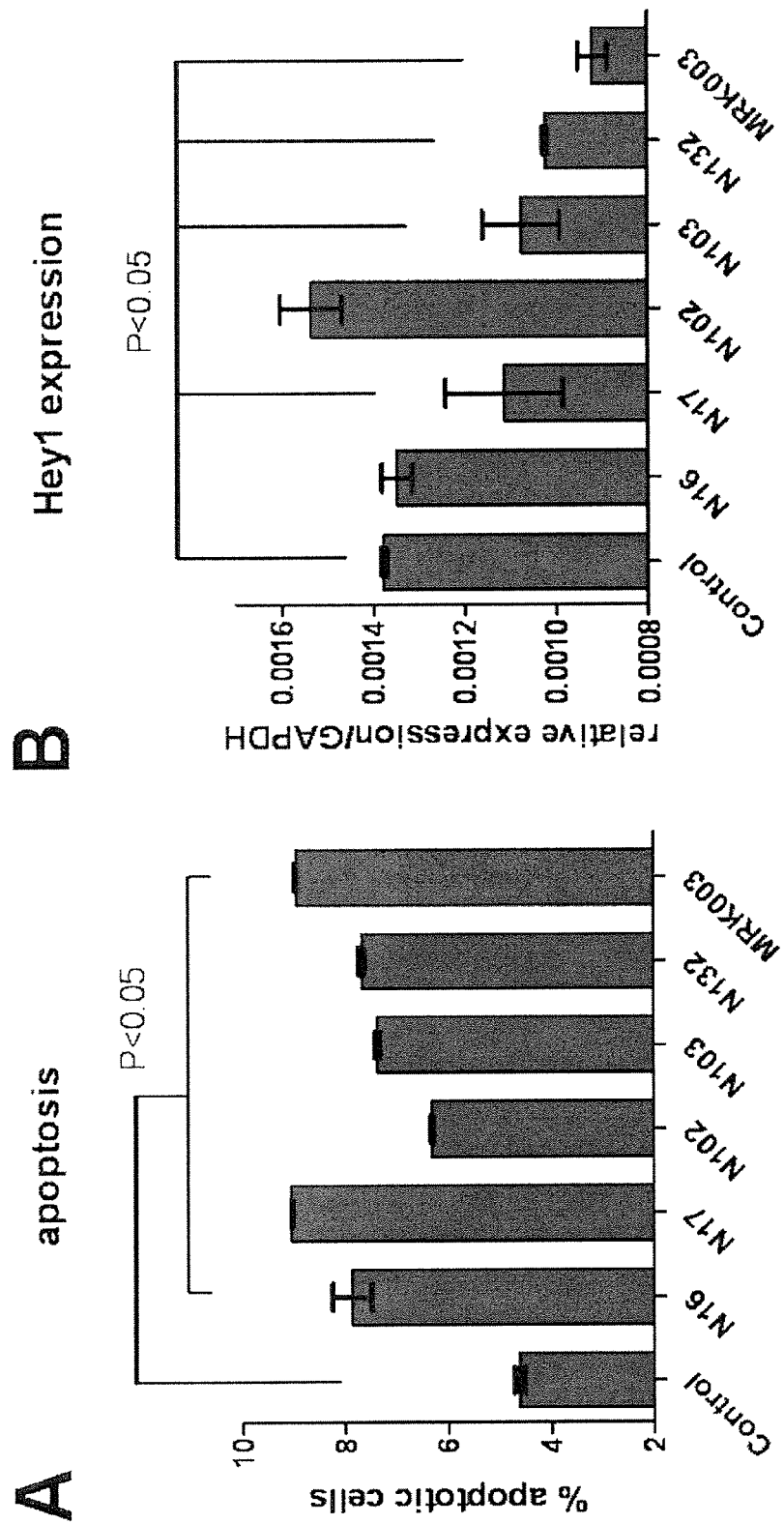
FIG. 14A-B. Notch3 peptides induce apoptosis and inhibit Notch3-regulated gene Hey1.
Figure 15:
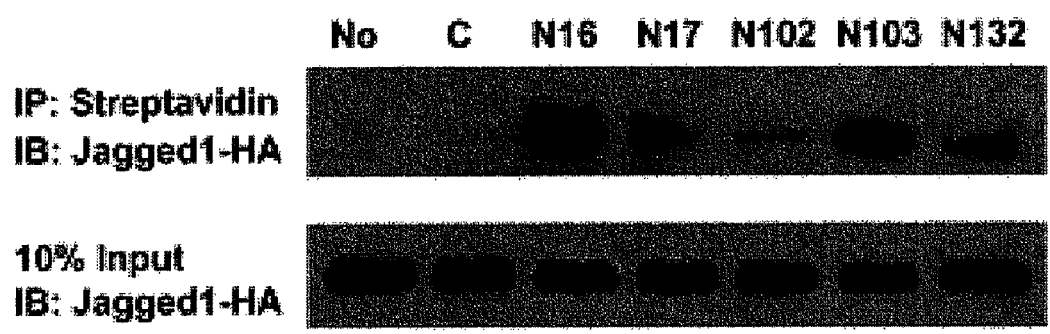
FIG. 15. Notch3 Peptides interrupt signaling through binding to ligand Jagged1. HEK cells were transfected with Jagged1-HA and treated with Notch3 peptides. The peptides were then immunoprecipitated from cell lysate with streptavidin beads and immunoblotted with anti-HA antibody. No: no input; C: control peptide. Sequences N16: CFNTLGGHS, N17: CVCVNGWTGES, N102: CATAV, N103: CFHGAT, N132: CLNGGS.

Notch3 peptides induce apoptosis, inhibit Notch3-regulated gene Hey1, and interrupt signaling through binding to ligand Jagged1. FIG. 13 is a representative experiment showing that the peptides induce apoptosis by Annexin V staining through screening using an FMAT system. Each of 155 different peptides were assayed in quadruplicate, and only those peptides that produced a significant increase of fluorescence signal in all 4 wells were considered potentially positive or capable of inducing apoptosis. The bar graphs here reflect fluorescence counts. FIG. 14A shows HCC2429 treated with Notch3 peptides N16, N17, N102, N103, N132, with induction of apoptosis by peptides compared to control. Treatment with peptides also reduced transcription of Notch3-dependent gene Hey1 as determined by real-time RT-PCR (FIG. 14B). Of note, N17 peptide both demonstrates highest apoptotic activity and best reduction in Hey1 transcription. FIG. 15 shows HEK cells transfected with Jagged1-HA and treated with Notch3 peptides. The peptides were then immunoprecipitated from cell lysate with streptavidin beads and immunoblotted with anti-HA antibody. This suggests that peptide induces apoptosis via binding to ligand Jagged1 and preventing activation of Notch3 receptor.

Figure 16:
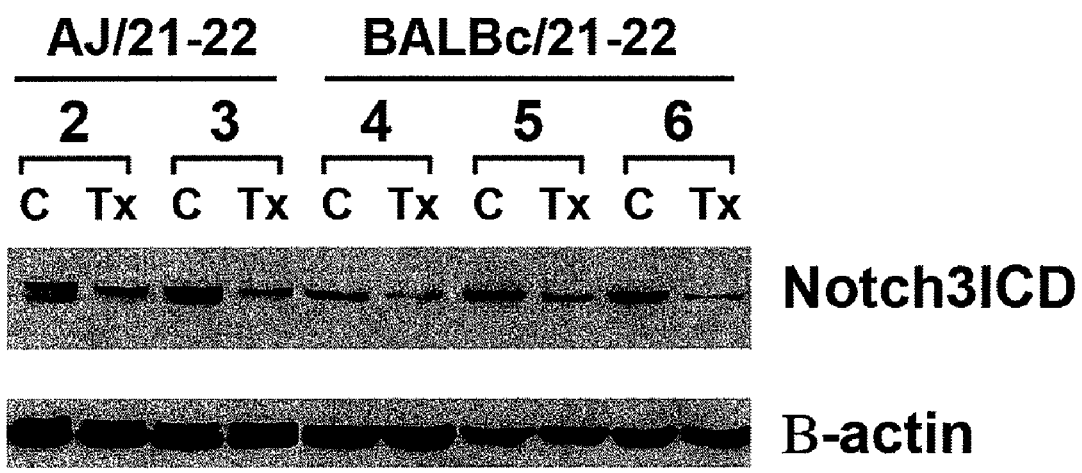
FIG. 16. Sera from mice immunized with Notch3 recombindant protein inhibit Notch3 activation. Immunoblot demonstrates sera from mice #2, 3, 4, 5, 6 can reduced cleavage of Notch3 ICD (Tx) in Notch3 expressing cell line HCC2429 as compared control (C). Recombinant protein representing EGF-like repeats 21-22 and encompassing sequence CTNLAGSFSCTCHGGYTGPSCDQDIND-CDPNPCLNGGS was used to immunize AJ and BALB/c mice. HCC2429 was plated in a 6-well plates and treated 1 µl/ml sera for 24 hr before harvesting.

Sera from mice immunized with Notch3 recombinant protein inhibit Notch3 activation. FIG. 16 shows an immunoblot that demonstrates that sera from mice #2, 3, 4, 5, 6 can reduced cleavage of Notch3 ICD (Tx) in Notch3 expressing cell line HCC2429 as compared a control (C). Recombinant protein representing EGF-like repeats 21-22 and encompassing sequence CTNLAGSFSCTCHGGYTGPSCDQDIND-CDPNPCLNGGS (SEQ. ID NO: 10) was used to immunize AJ and BALB/c mice.

Recombinant Fc-fusion Notch3 proteins inhibit Notch3 activation and induces apoptosis in vitro. FIG. 17A shows Fc-fusion protein comprised for N16-17 and N132 sequences inhibits Notch3 activation, while FIG. 17B shows that purified recombinant N16-17-Fc protein induces apoptosis as compared to control and Fc control after 40 hrs treatment. This study further supports the hypothesis that these regions of Notch3 are important for ligand interaction, and that disruption of this interaction using decoy recombinant receptor can inhibit Notch3 activation.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

IX. References

The following references, to the extent that they provide exemplary procedural or other details supplementary to those set forth herein, are specifically incorporated herein by reference:

U.S. Pat. No. 4,196,265
U.S. Pat. No. 4,554,101
U.S. Pat. No. 4,683,202
U.S. Pat. No. 4,684,611
U.S. Pat. No. 4,879,236
U.S. Pat. No. 4,952,500
U.S. Pat. No. 5,217,879
U.S. Pat. No. 5,302,523
U.S. Pat. No. 5,322,783
U.S. Pat. No. 5,384,253
U.S. Pat. No. 5,464,765
U.S. Pat. No. 5,506,138
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,610,042
U.S. Pat. No. 5,656,610

U.S. Pat. No. 5,670,488
U.S. Pat. No. 5,702,932
U.S. Pat. No. 5,736,524
U.S. Pat. No. 5,739,018
U.S. Pat. No. 5,780,448
U.S. Pat. No. 5,789,215,
U.S. Pat. No. 5,824,544
U.S. Pat. No. 5,830,725
U.S. Pat. No. 5,849,304
U.S. Pat. No. 5,851,826
U.S. Pat. No. 5,858,744
U.S. Pat. No. 5,871,982
U.S. Pat. No. 5,871,983
U.S. Pat. No. 5,871,986
U.S. Pat. No. 5,879,934
U.S. Pat. No. 5,888,502
U.S. Pat. No. 5,925,565
U.S. Pat. No. 5,928,906
U.S. Pat. No. 5,932,210
U.S. Pat. No. 5,935,819
U.S. Pat. No. 5,945,100
U.S. Pat. No. 5,955,331
U.S. Pat. No. 5,981,274
U.S. Pat. No. 5,994,136
U.S. Pat. No. 5,994,624
U.S. Pat. No. 6,013,516
Ahmad et al., *Dev. Biol.*, 194:86-98, 1998.
Almendro et al., *J. Immunol.*, 157(12):5411-5421, 1996.
Alves da Costa et al., *J. Neurochem.*, 90:800-806, 2004.
Amado and Chen, *Science*, 285(5428):674-676, 1999.
Angel et al., *Cell*, 49:729, 1987b.
Angel et al., *Mol. Cell. Biol.*, 7:2256, 1987a.
Armentano et al., *Proc. Natl. Acad. Sci. USA*, 87(16):6141-6145, 1990.
Artavanis-Tsakonas et al., *Science*, 284:770-776, 1999.
Atchison and Perry, *Cell*, 46:253, 1986.
Atchison and Perry, *Cell*, 48:121, 1987.
Ausubel et al., In: *Current Protocols in Molecular Biology*, John, Wiley & Sons, Inc, New York, 1994.
Banerji et al., *Cell*, 27(2 Pt 1):299-308, 1981.
Banerji et al., *Cell*, 33(3):729-740, 1983.
Barany and Merrifield, In: *The Peptides*, Gross and Meienhofer (Eds.), Academic Press, NY, 1-284, 1979.
Barry et al., *J. Biol. Chem.*, 276:15537-15546, 2001.
Bates, *Mol. Biotechnol.*, 2(2):135-145, 1994.
Batra et al., *Am. J. Respir. Cell Mol. Biol.*, 21(2):238-245, 1999.
Battraw and Hall, *Theor. App. Genet.*, 82(2):161-168, 1991.
Beatus and Lendahl, *J. Neurosci. Res.*, 54:125-136, 1998.
Bellavia et al., *Embo. J*, 19:3337-3348, 2000.
Bellavia et al., *Proc. Natl. Acad. Sci. USA*, 99:3788-3793, 2002.
Berkhout et al., *Cell*, 59:273-282, 1989.
Berset et al., *Science*, 291:1055-1058, 2001.
Bett et al., *J. Virololgy*, 67(10):5911-5921, 1993.
Bhattacharjee et al., *J. Plant Bioch. Biotech.*, 6(2):69-73. 1997.
Bilbao et al., *Transplant Proc.*, 31(1-2):792-793, 1999.
Blackwell et al., *Arch. Otolaryngol. Head. Neck Surg.*, 125(8):856-863, 1999.
Blanar et al, *EMBO J.*, 8:1139, 1989.
Blomer et al., *J. Virol.*, 71(9):6641-6649, 1997.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Brondello et al., *J. Biol. Chem.*, 272:1368-1376, 1997.

Bulla and Siddiqui, *J. Virol.*, 62:1437, 1986.
Callahan and Egan, *J. Mammary Gland Biol. Neoplasia.*, 9:145-163, 2004.
Campbell and Villarreal, *Mol. Cell. Biol.*, 8:1993, 1988.
Campbell et al., *Am. Rev. Respir. Dis.*, 130(3):417-423, 1984.
Campere and Tilghman, *Genes and Dev.*, 3:537, 1989.
Campo et al., *Nature*, 303:77, 1983.
Campos et al., *Circ. Res.*, 91:999-1006, 2002.
Capaldi et al., *Biochem. Biophys. Res. Comm.*, 76:425, 1977.
Caplen et al., *Gene Ther.*, 6(3):454-459, 1999.
Carbonelli et al., *FEMS Microbiol Lett.*, 177(1):75-82, 1999.
Case et al., *Proc. Natl. Acad. Sci. USA*, 96(6):2988-2893, 1999.
Celander and Haseltine, *J. Virology*, 61:269, 1987.
Celander et al., *J. Virology*, 62:1314, 1988.
Chandler et al., *Cell*, 33:489, 1983.
Chandler et al., *Proc. Natl. Acad. Sci. USA*, 94(8):3596-601, 1997.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell. Biol.* 7:2745-2752, 1987.
Chen et al., *Genes Dev.*, 10:2438-2451, 1996.
Chillon et al., *J. Virol.*, 73(3):2537-2540, 1999.
Christou et al., *Proc. Natl. Acad. Sci. USA*, 84(12):3962-3966, 1987.
Clay et al., *Pathol. Oncol. Res.*, 5(1):3-15, 1999.
Cocea, *Biotechniques*, 23(5):814-816, 1997.
Coffey et al., *Science*, 282(5392):1332-1334, 1998.
Cohen et al., *J. Cell. Physiol.*, 5:75, 1987.
Cook et al., *Cell*, 27:487-496, 1981.
Costa et al., *Mol. Cell. Biol.*, 8:81, 1988.
Cripe et al., *EMBO J.*, 6:3745, 1987.
Culotta and Hamer, *Mol. Cell. Biol.*, 9:1376, 1989.
Culver et al., *Science*, 256(5063):1550-1552, 1992.
Curry et al., *Oncogene*, 24:6333-6344, 2005.
D'Halluin et al., *Plant Cell*, 4(12):1495-1505, 1992.
Dandolo et al., *J. Virology*, 47:55-64, 1983.
Dang et al., *J. Natl. Cancer Inst.*, 92:1355-1357, 2000.
De Villiers et al., *Nature*, 312(5991):242-246, 1984.
DeLuca et al., *J. Virol.*, 56(2):558-570, 1985.
Deng et al., *Cell*, 82:675-684, 1995.
Derby et al., *Hear Res.*, 134(1-2):1-8, 1999.
Deschamps et al., *Science*, 230:1174-1177, 1985.
Domenga et al., *Genes Dev.*, 18:2730-2735, 2004.
Dorai et al., *Int. J. Cancer*, 82(6):846-852, 1999.
Dovey et al., *J. Neurochem.*, 76:173-181, 2001.
Edbrooke et al., *Mol. Cell. Biol.*, 9:1908, 1989.
Ellisen et al., *Cell*, 66:649-661, 1991.
Engel and Kohn, *Front Biosci.*, 4:e26-33, 1999.
EPO 0273085
Faux et al., *J. Neurosci.*, 21:5587-5596, 2001.
Fechheimer, et al., *Proc Natl. Acad. Sci. USA*, 84:8463-8467, 1987.
Feldman et al., *Semin. Interv. Cardiol.*, 1(3):203-208, 1996.
Feng and Holland, *Nature*, 334:6178, 1988.
Feng et al., *Nat. Biotechnol.*, 15(9):866-870, 1997.
Firak and Subramanian, *Mol. Cell. Biol.*, 6:3667, 1986.
Fisher et al., *Virology*, 217(1):11-22, 1996.
Fitzgerald et al., *Oncogene*, 19:4191-4198, 2000.
Foder et al., *Science*, 251:767-773, 1991.
Foecking and Hofstetter, *Gene*, 45(1):101-105, 1986.
Forster and Symons, *Cell*, 49:211-220, 1987.
Fraley et al., *Proc. Natl. Acad. Sci. USA*, 76:3348-3352, 1979.
Freifelder, In: *Physical Biochemistry Applications to Biochemistry and Molecular Biology*, 2nd Ed. Wm. Freeman and Co., NY, 1982.

Frohman, In: *PCR Protocols: A Guide To Methods And Applications*, Academic Press, N.Y., 1990.
Fujita et al., *Cell*, 49:357, 1987.
Fujiwara and Tanaka, *Nippon Geka Gakkai Zasshi*, 99(7):463-468, 1998.
Garoff and Li, *Curr. Opin. Biotechnol.*, 9(5):464-469, 1998.
Gamido et al., *J. Neurovirol.*, 5(3):280-288, 1999.
Gefter et al., *Somatic Cell Genet.*, 3:231-236, 1977.
Gerlach et al., *Nature (London)*, 328:802-805, 1987.
Ghosh and Bachhawat, In: *Liver Diseases, Targeted Diagnosis and Therapy Using Specific Receptors and Ligands*, Wu and Wu (Eds.), Marcel Dekker, New York, 87-104, 1991.
Gilles et al., *Cell*, 33:717, 1983.
Glasser et al., *Am. J. Physiol.*, 261:L349-356, 1991.
Gloss et al., *EMBO J.*, 6:3735, 1987.
Gnant et al., *Cancer Res.*, 59(14):3396-403, 1999.
Gnant et al., *J. Natl. Cancer Inst.*, 91(20):1744-1750, 1999.
Godbout et al., *Mol. Cell. Biol.*, 8:1169, 1988.
Goding, In: *Monoclonal Antibodies: Principles and Practice*, 2d ed., Orlando, Fla., Academic Press, 60-61, 65-66, 71-74, 1986.
Goodbourn and Maniatis, *Proc. Natl. Acad. Sci. USA*, 85:1447, 1988.
Goodbourn et al., *Cell*, 45:601, 1986.
Gopal, *Mol. Cell. Biol.*, 5:1188-1190, 1985.
Graham and Prevec *Mol. Biotechnol.*, 3(3):207-220, 1995.
Graham and Van Der Eb, *Virology* 52:456-467, 1973
Greene et al., *Immunology Today*, 10:272, 1989
Grosschedl and Baltimore, *Cell*, 41:885, 1985.
Hacia et al., *Nature Genet.*, 14:441-449, 1996.
Haecker et al., *Hum. Gene Ther.*, 7(15):1907-1914, 1996.
Han et al., *Euro. J Surgical Oncology*, 25:194-198, 1999.
Haneda et al., *Eur. J. Pharmacol.*, 365:1-7, 1999.
Harland and Weintraub, *J. Cell Biol.*, 101: 1094-1099, 1985.
Harlow and Lane, In: *Antibodies: A laboratory Manual*, Cold Spring Harbor Laboratories, Cold Spring Harbor, N.Y., 1988.
Haruki et al., *Cancer Res.*, 65:3555-3561, 2005.
Haslinger and Karin, *Proc. Natl. Acad. Sci. USA*, 82:8572, 1985.
Hauber and Cullen, *J. Virology*, 62:673, 1988.
Hayashi et al., *Neurosci. Lett.*, 267(1):37-40, 1999.
He et al., *Plant Cell Reports*, 14 (2-3):192-196, 1994.
Hen et al., *Nature*, 321:249, 1986.
Hensel et al., *Lymphokine Res.*, 8:347, 1989.
Hermens and Verhaagen, *Prog. Neurobiol.*, 55(4):399-432, 1998.
Herr and Clarke, *Cell*, 45:461, 1986.
Hirochika et al., *J. Virol.*, 61:2599, 1987.
Hirsch et al., *Br. J. Cancer*, 86:1449-1456, 2002.
Hirsch et al., *Mol. Cell. Biol.*, 10:1959, 1990.
Hogan et al., In: *Manipulating the Mouse Embryo: A Laboratory Manual*, 2nd ed., Cold Spring Harbor Laboratory Press, 1994.
Holbrook et al., *Virology*, 157:211, 1987.
Holley, *Nature*, 258:487-490, 1975.
Holzer et al., *Virology*, 253(1):107-114, 1999.
Horlick and Benfield, *Mol. Cell. Biol.*, 9:2396, 1989.
Hou and Lin, *Plant Physiology*, 111:166, 1996.
Howard et al., *Ann. NY Acad. Sci.*, 880:352-365, 1999.
Hrabe de Angelis et al., *Nature*, 386:717-721, 1997.
Huang et al., *Cell*, 27:245, 1981.
Huard et al., *Neuromuscul Disord.*, 7(5):299-313, 1997.
Hug et al., *Mol. Cell. Biol.*, 8:3065, 1988.
Hwang et al., *Mol. Cell. Biol.*, 10:585, 1990.
Imagawa et al., *Cell*, 51:251, 1987.
Imai et al., *J. Virol.*, 72(5):4371-4378, 1998.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Innis et al., *Proc Natl Acad Sci USA*, 85(24):9436-9440, 1988.
Irie et al., *Antisense Nucleic Acid Drug Dev.*, 9(4):341-349, 1999.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Jemal et al., *CA Cancer J. Clin.*, 55:10-30, 2005.
Jhappan et al., *Genes Dev.*, 6:345-355, 1992.
Johnson et al., IN: *Biotechnology And Pharmacy*, Pezzuto et al., (Eds.), Chapman and Hall, New York, 1993.
Johnson et al., *Mol. Cell. Biol.*, 9:3393, 1989.
Johnston and Edgar, *Nature*, 394:82-84, 1998.
Johnston et al., *J. Virol.*, 73(6):4991-5000, 1999.
Joutel et al., *J. Clin. Invest.*, 105:597-605, 2000.
Joyce, *Nature*, 338:217-244, 1989.
Kadesch and Berg, *Mol. Cell. Biol.*, 6:2593, 1986.
Kaeppler et al., *Plant Cell Reports*, 9:415-418, 1990.
Kaneda et al., *Science*, 243:375-378, 1989.
Karin et al., *Mol. Cell. Biol.*, 7:606, 1987.
Katinka et al., *Cell*, 20:393, 1980.
Kato et al, *J. Biol. Chem.*, 266(6):3361-3364, 1991.
Kaufman et al., *Surv. Opthalmol.*, 43 Suppl 1: S91-97, 1999.
Kawamoto et al., *Mol. Cell. Biol.*, 8:267, 1988.
Kay, *Haemophilia*, 4(4):389-392, 1998.
Kiledjian et al., *Mol. Cell. Biol.*, 8:145, 1988.
Kim and Cech, *Proc. Natl. Acad. Sci. USA*, 84:8788-8792, 1987.
Klamut et al., *Mol. Cell. Biol.*, 10: 193, 1990.
Klimatcheva et al., *Front Biosci.*, 4:D481-96, 1999.
Koch et al., *Mol. Cell. Biol.*, 9:303, 1989.
Kohler and Milstein, *Eur. J. Immunol.*, 6:511-519, 1976.
Kohler and Milstein, *Nature*, 256:495-497, 1975.
Kohut et al., *Am. J. Physiol.*, 275(6 Pt 1):L1089-94, 1998.
Kooby et al., *FASEB J*, 13(11):1325-1334, 1999.
Kornberg, In: *DNA Replication*, W. H. Freeman and Company, New York, 1992.
Kraus et al., *FEBS Lett.*, 428(3):165-170, 1998.
Krebs et al., *Genes Dev.*, 14:1343-1352, 2000.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Krisky et al., *Gene Ther*, 5(11):1517-1530, 1998a.
Krisky et al., *Gene Ther*, 5(12):1593-1603, 1998b.
Kuhl et al., *Cell*, 50:1057, 1987.
Kunz et al., *Nucl. Acids Res.*, 17:1121, 1989.
Kwoh et al., *Proc. Natl. Acad. Sci. USA*, 86(4):1173-1177, 1989.
Kyte and Doolittle, *J. Mol. Biol.*, 157(1):105-132, 1982.
Lachmann and Efstathiou, *Clin. Sci. (Colch)*, 96(6):533-541, 1999.
Lanford et al., *Nat. Genet.*, 21:289-292, 1999.
Lardelli et al., *Mech Dev.*, 59:177-190, 1996.
Lareyre et al., *J. Biol. Chem.*, 274(12):8282-8290, 1999.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Lazzeri, *Methods Mol. Biol.*, 49:95-106, 1995.
Lee et al., *J. Auton. Nerv. Syst.*, 74(2-3):86-90, 1997.
Lee et al., *Korean J. Genet.*, 11(2):65-72, 1989.
Lee et al., *Nature*, 294:228, 1981.

Lee et al., *Nature*, 329(6140):642-645, 1987.
Lee et al., *Nucleic Acids Res.*, 12:4191-206, 1984.
Leibowitz et al., *Diabetes*, 48(4):745-753, 1999.
Leonhardt et al., *J. Cell Biol.*, 149:271-280, 2000.
Lesch, *Biol. Psychiatry*, 45(3):247-253, 1999.
Levenson et al., *Human Gene Therapy*, 9:1233-1236, 1998.
Levinson et al., *Nature*, 295:79, 1982.
Levitan and Greenwald, *Nature*, 377:351-354, 1995.
Li et al., *Science*, 275:1943-1947, 1997.
Liang and Pardee, *Nature Reviews Cancer*, 3:869-876, 2003.
Liang, *Biotechniques*, 33:338-346, 2002.
Lin et al., *Mol. Cell. Biol.*, 10:850, 1990.
Linggi et al., *Oncogene*, 25:160-163, 2006.
Lu et al., *Clin. Cancer Res.*, 10:3291-3300, 2004.
Lundstrom, *J. Recept. Signal Transduct. Res.*, 19(1-4):673-686, 1999.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Ma et al., *Hematol. Oncol.*, 17:91-105, 1997.
Macejak and Sarnow, *Nature*, 353:90-94, 1991.
Magi-Galluzzi et al., *Lab Invest.*, 76:37-51, 1997.
Majors and Varmus, *Proc. Natl. Acad. Sci. USA*, 80:5866, 1983.
Marienfeld et al., *Gene Ther.*, 6(6): 1101-1113, 1999.
Mastrangelo et al., *Cancer Gene Ther.*, 6(5):409-422 1999.
McNeall et al., *Gene*, 76:81, 1989.
Meert et al., *Eur. Respir. J.*, 20:975-981, 2002.
Merrifield, *Science*, 232(4748):341-347 1986.
Michel and Westhof, *J. Mol. Biol.*, 216:585-610, 1990.
Miksicek et al., *Cell*, 46:203, 1986.
Miller et al., *Methods Enzymol.*, 217:581-599, 1993.
Mitsiadis et al. *Dev. Biol.*, 204:420-431, 1998.
Miyamoto et al., *Cancer Cell*, 3:565-576, 2003.
Miyatake et al., *Gene Ther.*, 6(4):564-572, 1999.
Moldawer et al., *Shock*, 12(2):83-101, 1999.
Mordacq and Linzer, *Genes and Dev.*, 3:760, 1989.
Moreau et al., *Nucl. Acids Res.*, 9:6047, 1981.
Moriuchi et al., *Cancer Res.*, 58(24):5731-5737, 1998.
Morrison et al., *J. Gen. Virol.*, 78(Pt 4):873-878, 1997.
Muesing et al., *Cell*, 48:691, 1987.
Mumm and Kopan, *Dev. Biol.*, 228:151-165, 2000.
Nahle et al., *Nat. Cell Biol.*, 4:859-864, 2002.
Naldini et al., *Proc. Natl. Acad. Sci. USA*, 93(21):11382-11388, 1996.
Neumann et al., *Proc. Natl. Acad. Sci. USA*, 96(16):9345-9350, 1999.
Ng et al., *Nuc. Acids Res.*, 17:601, 1989.
Nicolau and Sene, *Biochim. Biophys. Acta*, 721:185-190, 1982.
Nicolau et al., *Methods Enzymol.*, 149:157-176, 1987
Nomoto et al., *Gene*, 236(2):259-271, 1999.
Ohara et al., *Proc. Natl. Acad. Sci. USA*, 86:5673-5677, 1989.
Omirulleh et al., *Plant Mol. Biol.*, 21(3):415-28, 1993.
Ondek et al., *EMBO J.*, 6:1017, 1987.
Ornitz et al., *Mol. Cell. Biol.*, 7:3466, 1987.
Oswald et al., *Mol. Cell. Biol.*, 18:2077-2088, 1998.
Palmiter et al., *Nature*, 300:611, 1982.
Paris et al., *Eur. J. Pharmacol.*, 514:1-15, 2005.
Parks et al., *J. Virol.*, 71(4):3293-8, 1997.
PCT Appln. WO 9217598
PCT Appln. WO 94/09699
PCT Appln. WO 95/06128
Pear et al., *J. Exp. Med.*, 183:2283-2291, 1996.
Pease et al., *Proc. Natl. Acad. Sci. USA*, 91:5022-5026, 1994.
Pech et al., *Mol. Cell. Biol.*, 9:396, 1989.
Pelletier and Sonenberg, *Nature*, 334:320-325, 1988.
Pelletier et al., *Cancer Res.*, 66:3681-3687, 2006.
Perales et al., *Proc. Natl. Acad. Sci. USA*, 91:4086-4090, 1994.
Perez-Stable and Constantini, *Mol. Cell. Biol.*, 10:1116, 1990.
Petrof, *Eur. Respir. J.*, 11(2):492-497, 1998.
Picard and Schaffner, *Nature*, 307:83, 1984.
Pignon J et al., *Hum. Mutat.*, 3(2):126-132, 1994.
Pinkert et al., *Genes and Dev.*, 1:268, 1987.
Plows et al., *Biochem J.*, 362:305-315, 2002.
Polyak et al., *Genes Dev.*, 10:1945-1952, 1996.
Ponta et al., *Proc. Natl. Acad. Sci. USA*, 82:1020, 1985.
Porton et al., *Mol. Cell. Biol.*, 10: 1076, 1990.
Potrykus et al., *Mol. Gen. Genet.*, 199:183-188, 1985.
Potter et al., *Proc. Natl. Acad. Sci. USA*, 81:7161-7165, 1984.
Purow et al., *Cancer Res.*, 65:2353-2363, 2005.
Qin et al., *Mol. Cancer. Ther.*, 3:895-902, 2004.
Queen and Baltimore, *Cell*, 35:741, 1983.
Quinn et al., *Mol. Cell. Biol.*, 9:4713, 1989.
Rabinovitch et al., *Diabetes*, 48(6):1223-1229, 1999.
Rebay et al., *Cell*, 74:319-329, 1993.
Reddy et al., *J. Virol.*, 72(2):1394-1402, 1998.
Redondo et al., *Science*, 247:1225, 1990.
Reinhold-Hurek and Shub, *Nature*, 357:173-176, 1992.
Reisman and Rotter, *Mol. Cell. Biol.*, 9:3571, 1989.
Remington's Pharmaceutical Sciences, 15$^{th}$ Ed., 33:624-652, 1990.
Remington's Pharmaceutical Sciences, 15$^{th}$ Ed., 1035-1038 and 1570-1580, 1990.
Resendez Jr. et al., *Mol. Cell. Biol.*, 8:4579, 1988.
Rhodes et al., *Methods Mol. Biol.*, 55:121-131, 1995.
Ripe et al., *Mol. Cell. Biol.*, 9:2224, 1989.
Rippe et al., *Mol. Cell. Biol.*, 10:689-695, 1990.
Rittling et al., *Nuc. Acids Res.*, 17:1619, 1989.
Robbins and Ghivizzani, *Pharmacol. Ther.*, 80(1):35-47, 1998.
Robbins et al., *Proc. Natl. Acad. Sci. USA*, 95(17):10182-10187 1998.
Robbins et al., *Trends Biotechnol.*, 16(1):35-40, 1998.
Robey et al., *Cell*, 87:483-492, 1996.
Rodenhuis et al., *J. Clin. Oncol.*, 15:285-291, 1997.
Rohn et al., *J. Virol.*, 70:8071-8080, 1996.
Rosen et al., *Cell*, 41:813, 1988.
Sakai et al., *Genes and Dev.*, 2:1144, 1988.
Sambrook et al., In: *Molecular Cloning: A Laboratory Manual*, Cold Spring Harbor Laboratory Press, Cold Spring Harbor, N.Y., 1(7):7.19-17.29, 1989.
Santagata et al., *Cancer Res.*, 64:6854-6857, 2004.
Sarver et al., *Science*, 247:1222-1225, 1990.
Satake et al., *J. Virology*, 62:970, 1988.
Sawai et al., *Mol. Genet. Metab.*, 67(1):36-42, 1999.
Scanlon et al., *Proc. Natl. Acad. Sci. USA*, 88:10591-10595, 1991.
Schaffner et al., *J. Mol. Biol.*, 201:81, 1988.
Searle et al., *Mol. Cell. Biol.*, 5:1480, 1985.
Sharp and Marciniak, *Cell*, 59:229, 1989.
Shaul and Ben-Levy, *EMBO J.*, 6:1913, 1987.
Shelly et al., *J. Cell Biochem.*, 73:164-175, 1999.
Sherman et al., *Mol. Cell. Biol.*, 9:50, 1989.
Shimizu et al., *Mol. Cell. Biol.*, 20:6913-6922, 2000.
Shoemaker et al., *Nature Genetics*, 14:450-456, 1996.
Sivaraman et al., *J. Clin. Invest.*, 99:1478-1483, 1997.
Sleigh and Lockett, *J. EMBO*, 4:3831, 1985.
Small et al., *J. Biol. Chem.*, 278:16405-16413, 2003.
Smith, *Arch. Neurol.*, 55(8):1061-1064, 1998.
Spalholz et al., *Cell*, 42:183, 1985.

Spandau and Lee, *J. Virology*, 62:427, 1988.
Spandidos and Wilkie, *EMBO J.*, 2:1193, 1983.
Stambolic et al., *Mol. Cell*, 8:317-325, 2001.
Steck et al., *Nat. Genet.*, 15:356-362, 1997.
Stein et al., *J. Biol. Chem.*, 279:48930-48940, 2004.
Stephens and Hentschel, *Biochem. J*, 248:1, 1987.
Stewart and Young, In: *Solid Phase Peptide Synthesis*, 2nd Ed., Pierce Chemical Co., 1984.
Stewart et al., *Gene Ther.*, 6(3):350-363, 1999.
Stuart et al., *Nature*, 317:828, 1985.
Sullivan and Peterlin, *Mol. Cell. Biol.*, 7:3315, 1987.
Sundaram, *Genes Dev.*, 19:1825-1839, 2005.
Suzuki et al., *Biochem. Biophys. Res. Commun.*, 252(3):686-690, 1998.
Swartzendruber and Lehman, *J. Cell. Physiology*, 85:179, 1975.
Sweeney et al., *Faseb. J.*, 18:1421-1423, 2004.
Taichman et al., *Dev. Dyn.*, 225:166-175, 2002.
Takebe et al., *Mol. Cell. Biol.*, 8:466, 1988.
Tam et al., *J. Am. Chem. Soc.*, 105:6442, 1983.
Tanaka et al., *Oncogene*, 8:2253-2258, 1993.
Taniura et al., *J. Biol. Chem.*, 274:16242-16248, 1999.
Tavernier et al., *Nature*, 301:634, 1983.
Taylor and Kingston, *Mol. Cell. Biol.*, 10:165, 1990a.
Taylor and Kingston, *Mol. Cell. Biol*, 10:176, 1990b.
Taylor and Stark, *Oncogene*, 20:1803-1815, 2001.
Taylor et al., *J. Biol. Chem.*, 264:15160, 1989.
Thiesen et al., *J. Virology*, 62:614, 1988.
Timiryasova et al., *Int. J. Oncol.*, 14(5):845-854, 1999.
Timiryasova et al., *Oncol. Res.;* 11(3):133-144, 1999.
Traverse et al., *Biochem. J*, 288 (Pt 2):351-355, 1992.
Treisman, *Cell*, 42:889, 1985.
Tronche et al., *Mol. Biol. Med.*, 7:173, 1990.
Trudel and Constantini, *Genes and Dev.*, 6:954, 1987.
Tsukada et al., *Plant Cell Physiol.*, 30(4)599-604, 1989.
Tsumaki et al., *J. Biol. Chem.*, 273(36):22861-22864, 1998.
Tur-Kaspa et al., *Mol. Cell. Biol.*, 6:716-718, 1986.
Tyndell et al., *Nuc. Acids. Res.*, 9:6231, 1981.
Vanderkwaak et al., *Gynecol. Oncol.*, 74(2):227-234, 1999.
Vannice and Levinson, *J. Virology*, 62:1305, 1988.
Vasseur et al., *Proc Natl. Acad. Sci. USA*, 77:1068, 1980.
Vogelstein et al., *Nature*, 408(6810):307-310, 2000.
Vogelstein, *Nature*, 348(6303):681-682, 1990.
Vousden and Lu, *Nat. Rev. Cancer*, 2:594-604, 2002.
Vousden and Prives, *Cell*, 120:7-10, 2005.
Wagner et al., *Science*, 260:1510-1513, 1990.
Walker et al., *Nucleic Acids Res.*, 20(7):1691-1696, 1992.
Wang and Calame, *Cell*, 47:241, 1986.
Wang et al., *Gynecol. Oncol.*, 71(2):278-287, 1998.
Wang et al., *J. Biol. Chem.*, 277:23165-23171, 2002.
Weber et al., *Cell*, 36:983, 1984.
Weihl et al., *Neurosurgery*, 44(2):239-252, 1999.
Weinberg et al., *Biochemistry*, 28:8263-8269, 1989.
Weinberger et al., *Mol. Cell. Biol.*, 8:988, 1984.
Weng et al., *Science*, 306:269-271, 2004.
White et al., *J. Virol.*, 73(4):2832-28340, 1999.
Williams et al., *Blood*, 107(3):931-939, 2006.
Wilson, *J. Clin. Invest.*, 98(11):2435, 1996.
Winoto and Baltimore, *Cell*, 59:649, 1989.
Wolfe and Kopan, *Science*, 305:1119-1123, 2004.
Wong et al., *Gene*, 10:87-94, 1980.
Wu and Wallace, *Genomics*, 4:560-569, 1989.
Wu and Wu, *Adv. Drug Delivery Rev.*, 12:159-167, 1993.
Wu and Wu, *J. Biol. Chem.*, 262:4429-4432, 1987.
Wu et al., *Biochem. Biophys. Res. Commun.*, 233(1):221-226, 1997.
Wu, *Chung Hua Min Kuo Hsiao Erh Ko I Hsueh Hui Tsa Chih*, 39(5):297-300, 1998.
Xue et al., *Hum Mol Genet.*, 8:723-730, 1999.
Yamada et al., *Proc. Natl. Acad. Sci. USA*, 96(7):4078-4083, 1999.
Yang and Liang, *Mol. Biotechnol.*, 3:197-208, 2004.
Yeung et al., *Gene Ther.*, 6(9):1536-1544, 1999.
Yoo et al., *Science*, 303:663-666, 2004.
Yoon et al., *J. Gastrointest. Surg.*, 3(1):34-48, 1999.
Yu and Zhang, *Biochem. Biophys. Res. Commun.*, 331:851-858, 2005.
Yu et al., *Proc. Natl. Acad. Sci. USA*, 100:1931-1936, 2003.
Yu et al., *Proc. Natl. Acad. Sci. USA*, 96:14517-14522, 1999.
Yutzey et al., *Mol. Cell. Biol.*, 9:1397, 1989.
Zeng et al., *Cancer Cell*, 8:13-23, 2005.
Zhao-Emonet et al., *Biochim. Biophys. Acta*, 1442(2-3):109-119, 1998.
Zheng et al., *J. Gen. Virol.*, 80(Pt 7):1735-1742, 1999.
Zhou et al., *Exp. Hematol*, 21:928-933, 1993.
Zufferey et al., *Nat. Biotechnol.*, 15(9):871-875, 1997.

What is claimed is:

1. An isolated and purified peptide comprising CFNTLGGHS (SEQ ID NO:3) or CVCVNGWTGES (SEQ ID NO:4), wherein the length of the peptide is no more than 50 residues.

2. The isolated and purified peptide of claim 1, wherein the peptide comprises SEQ ID NO:3.

3. The isolated and purified peptide of claim 1, wherein the peptide comprises SEQ ID NO:4.

4. The isolated and purified peptide of claim 1, wherein the peptide comprises CFNTLGGHSCVCVNGWTGESCSQNIDDCATAVCFHGAT (SEQ ID NO:9).

5. An isolated and purified peptide comprising CTNLAGSFSCTCHGGYTGPSCDQDINDCDPNPCLNGGS (SEQ ID NO:10), wherein the length of the peptide is no more than 50 residues.

6. The isolated and purified peptide of claim 1, wherein the length of said peptide is no more than 25 residues.

7. The isolated and purified peptide of claim 1, wherein the length of said peptide is no more than 20 residues.

8. The isolated and purified peptide of claim 1, wherein the length of said peptide is no more than 15 residues.

9. An isolated and purified peptide consisting of CFNTLGGHS (SEQ ID NO:3), CVCVNGWTGES (SEQ ID NO:4), CATAV (SEQ ID NO:5), CFHGAT (SEQ ID NO:6), CVSNP (SEQ ID NO:7), CLNGGS (SEQ ID NO:8), CFNTLGGHSCVCVNGWTGESCSQNIDDCATAVCFHGAT (SEQ ID NO:9) or CTNLAGSFSCTCHGGYTGPSCDQDINDCDPNPCLNGGS (SEQ ID NO:10).

10. A composition comprising the isolated and purified peptide of claim 1, 5 or 9, and a pharmaceutically acceptable diluent, buffer or excipient.

11. A method of inhibiting Notch3 receptor signaling comprising contacting a cell expressing Notch3 with a peptide comprising CFNTLGGHS (SEQ ID NO:3) or CVCVNGWTGES (SEQ ID NO:4), wherein the length of the peptide is no more than 50 residues.

12. The method of claim 11, wherein said cell is a cancer cell.

13. The method of claim 12, wherein said cancer cell is a lung cancer cell.

14. The method of claim 12, wherein said cancer cell is an adenocarcinoma cell.

15. The method of claim 11, further comprising contacting said cell with one or more peptides comprising CATAV (SEQ ID NO:5), CFHGAT (SEQ ID NO:6), CVSNP (SEQ ID NO:7) or CLNGGS (SEQ ID NO:8).

16. The method of claim 11, wherein the length of said peptide is no more than 25 residues, 20 residues or 15 residues.

17. A method of inhibiting Notch3 receptor signaling comprising contacting a cell expressing Notch3 with a peptide comprising CFNTLGGHSCVCVGWTGESCSQNIDDCATAVCFHGAT (SEQ ID NO:9) or CTNLAGSFSCTCHGGYTGPSCDQDINDCDPNPCLNGGS (SEQ ID NO:10), wherein the length of said peptide is no more than 50 residues.

18. A method of inhibiting Notch3 receptor signaling comprising contacting a cell expressing Notch3 with a peptide consisting of CFNTLGGHS (SEQ ID NO:3), CVCVNGWTGES (SEQ ID NO:4), CATAV (SEQ ID NO:5), CFHGAT (SEQ ID NO:6), CVSNP (SEQ ID NO:7), CLNGGS (SEQ ID NO:8), CFNTLGGHSCVCVNGWTGESCSQNIDDCATAVCFHGAT (SEQ ID NO:9) or CTNLAGSFSCTCHGGYTGPSCDQDINDCDPNPCLNGGS (SEQ ID NO:10).

19. The method of claim 11, further comprising contacting said cell with a second agent that inhibits cancer cell growth, differentiation, metastasis or drug resistance.

20. A pharmaceutical formulation comprising one or both of the peptides CFNTLGGHS (SEQ ID NO:3) and CVCVNGWTGES (SEQ ID NO:4).

21. The pharmaceutical formulation of claim 20, further comprising one, two, three, four, five, or six of the peptides selected from the group consisting of: CATAV (SEQ ID NO:5), CFHGAT (SEQ ID NO:6), CVSNP (SEQ ID NO:7), CLNGGS (SEQ ID NO:8), CFNTLGGHSCVCVNGWTGESCSQNIDDCATAVCFHGAT (SEQ ID NO:9) and CTNLAGSFSCTCHGGYTGPSCDQDINDCDPNPCLNGGS (SEQ ID NO:10).

* * * * *

SEQUENCE LISTING

```
<160> NUMBER OF SEQ ID NOS: 10

<210> SEQ ID NO 1
<211> LENGTH: 8091
<212> TYPE: DNA
<213> ORGANISM: Homo sapiens
<220> FEATURE:
<221> NAME/KEY: CDS
<222> LOCATION: (79)..(7044)

<400> SEQUENCE: 1
acgcggcgcg gaggctggcc cgggacgcgc ccggagccca gggaaggagg gaggagggga       60
gggtcgcggc cggccgcc atg ggg ccg ggg gcc cgt ggc cgc cgc cgc cgc        111
                    Met Gly Pro Gly Ala Arg Gly Arg Arg Arg
                    1               5                   10 cgt cgc ccg atg tcg ccg cca ccg cca ccg ccc gtg cgg gcg ctg            159
Arg Arg Pro Met Ser Pro Pro Pro Pro Pro Val Arg Ala Leu
            15                  20                  25
```

-continued

| | |
|---|---|
| ccc ctg ctg ctg ctg cta gcg ggg ccg ggg gct gca gcc ccc cct tgc<br>Pro Leu Leu Leu Leu Leu Ala Gly Pro Gly Ala Ala Ala Pro Pro Cys<br>           30                      35                        40 | 207 |
| ctg gac gga agc ccg tgt gca aat gga ggt cgt tgc acc cag ctg ccc<br>Leu Asp Gly Ser Pro Cys Ala Asn Gly Gly Arg Cys Thr Gln Leu Pro<br>45                       50                        55 | 255 |
| tcc cgg gag gct gcc tgc ctg tgc ccg cct ggc tgg gtg ggt gag cgg<br>Ser Arg Glu Ala Ala Cys Leu Cys Pro Pro Gly Trp Val Gly Glu Arg<br>60                       65                       70                        75 | 303 |
| tgt cag ctg gag gac ccc tgt cac tca ggc ccc tgt gct ggc cgt ggt<br>Cys Gln Leu Glu Asp Pro Cys His Ser Gly Pro Cys Ala Gly Arg Gly<br>                    80                        85                        90 | 351 |
| gtc tgc cag agt tca gtg gtg gct ggc acc gcc cga ttc tca tgc cgg<br>Val Cys Gln Ser Ser Val Val Ala Gly Thr Ala Arg Phe Ser Cys Arg<br>               95                        100                      105 | 399 |
| tgc ccc cgt ggc ttc cga ggc cct gac tgc tcc ctg cca gat ccc tgc<br>Cys Pro Arg Gly Phe Arg Gly Pro Asp Cys Ser Leu Pro Asp Pro Cys<br>            110                        115                      120 | 447 |
| ctc agc agc cct tgt gcc cac ggt gcc cgc tgc tca gtg ggg ccc gat<br>Leu Ser Ser Pro Cys Ala His Gly Ala Arg Cys Ser Val Gly Pro Asp<br>125                      130                        135 | 495 |
| gga cgc ttc ctc tgc tcc tgc cca cct ggc tac cag ggc cgc agc tgc<br>Gly Arg Phe Leu Cys Ser Cys Pro Pro Gly Tyr Gln Gly Arg Ser Cys<br>140                      145                        150                      155 | 543 |
| cga agc gac gtg gat gag tgc cgg gtg ggt gag ccc tgc cgc cat ggt<br>Arg Ser Asp Val Asp Glu Cys Arg Val Gly Glu Pro Cys Arg His Gly<br>                    160                        165                      170 | 591 |
| ggc acc tgc ctc aac aca cct ggc tcc ttc cgc tgc cag tgt cca gct<br>Gly Thr Cys Leu Asn Thr Pro Gly Ser Phe Arg Cys Gln Cys Pro Ala<br>                  175                        180                      185 | 639 |
| ggc tac aca ggg cca cta tgt gag aac ccc gcg gtg ccc tgt gcg ccc<br>Gly Tyr Thr Gly Pro Leu Cys Glu Asn Pro Ala Val Pro Cys Ala Pro<br>190                      195                        200 | 687 |
| tca cca tgc cgt aac ggg ggc acc tgc agg cag agt ggc gac ctc act<br>Ser Pro Cys Arg Asn Gly Gly Thr Cys Arg Gln Ser Gly Asp Leu Thr<br>205                      210                        215 | 735 |
| tac gac tgt gcc tgt ctt cct ggg ttt gag ggt cag aat tgt gaa gtg<br>Tyr Asp Cys Ala Cys Leu Pro Gly Phe Glu Gly Gln Asn Cys Glu Val<br>220                      225                        230                      235 | 783 |
| aac gtg gac gac tgt cca gga cac cga tgt ctc aat ggg ggg aca tgc<br>Asn Val Asp Asp Cys Pro Gly His Arg Cys Leu Asn Gly Gly Thr Cys<br>                    240                        245                      250 | 831 |
| gtg gat ggc gtc aac acc tat aac tgc cag tgc cct cct gag tgg aca<br>Val Asp Gly Val Asn Thr Tyr Asn Cys Gln Cys Pro Pro Glu Trp Thr<br>                  255                        260                      265 | 879 |
| ggc cag ttc tgc acg gag gac gtg gat gag tgt cag ctg cag ccc aac<br>Gly Gln Phe Cys Thr Glu Asp Val Asp Glu Cys Gln Leu Gln Pro Asn<br>                    270                        275                      280 | 927 |
| gcc tgc cac aat ggg ggt acc tgc ttc aac acg ctg ggt ggc cac agc<br>Ala Cys His Asn Gly Gly Thr Cys Phe Asn Thr Leu Gly Gly His Ser<br>285                      290                        295 | 975 |
| tgc gtg tgt gtc aat ggc tgg aca ggt gag agc tgt agt cag aat atc<br>Cys Val Cys Val Asn Gly Trp Thr Gly Glu Ser Cys Ser Gln Asn Ile<br>300                      305                        310                      315 | 1023 |
| gat gac tgt gcc aca gcc gtg tgc ttc cat ggg gcc acc tgc cat gac<br>Asp Asp Cys Ala Thr Ala Val Cys Phe His Gly Ala Thr Cys His Asp<br>                    320                        325                      330 | 1071 |
| cgc gtg gct tct ttc tac tgt gcc tgc ccc atg ggc aag act ggc ctc<br>Arg Val Ala Ser Phe Tyr Cys Ala Cys Pro Met Gly Lys Thr Gly Leu | 1119 |

-continued

```
                335                 340                 345
ctg tgt cac ctg gat gac gcc tgt gtc agc aac ccc tgc cac gag gat      1167
Leu Cys His Leu Asp Asp Ala Cys Val Ser Asn Pro Cys His Glu Asp
            350                 355                 360 gct atc tgt gac aca aat ccg gtg aac ggc cgg gcc att tgc acc tgt      1215
Ala Ile Cys Asp Thr Asn Pro Val Asn Gly Arg Ala Ile Cys Thr Cys
365                 370                 375 cct ccc ggc ttc acg ggt ggg gca tgt gac cag gat gtg gac gag tgc      1263
Pro Pro Gly Phe Thr Gly Gly Ala Cys Asp Gln Asp Val Asp Glu Cys
380                 385                 390                 395 tct atc ggc gcc aac ccc tgc gag cac ttg ggc agg tgc gtg aac acg      1311
Ser Ile Gly Ala Asn Pro Cys Glu His Leu Gly Arg Cys Val Asn Thr
            400                 405                 410 cag ggc tcc ttc ctg tgc cag tgc ggt cgt ggc tac act gga cct cgc      1359
Gln Gly Ser Phe Leu Cys Gln Cys Gly Arg Gly Tyr Thr Gly Pro Arg
            415                 420                 425 tgt gag acc gat gtc aac gag tgt ctg tcg ggg ccc tgc cga aac cag      1407
Cys Glu Thr Asp Val Asn Glu Cys Leu Ser Gly Pro Cys Arg Asn Gln
            430                 435                 440 gcc acg tgc ctc gac cgc ata ggc cag ttc acc tgt atc tgt atg gca      1455
Ala Thr Cys Leu Asp Arg Ile Gly Gln Phe Thr Cys Ile Cys Met Ala
445                 450                 455 ggc ttc aca gga acc tat tgc gag gtg gac att gac gag tgt cag agt      1503
Gly Phe Thr Gly Thr Tyr Cys Glu Val Asp Ile Asp Glu Cys Gln Ser
460                 465                 470                 475 agc ccc tgt gtc aac ggt ggg gtc tgc aag gac cga gtc aat ggc ttc      1551
Ser Pro Cys Val Asn Gly Gly Val Cys Lys Asp Arg Val Asn Gly Phe
            480                 485                 490 agc tgc acc tgc ccc tcg ggc ttc agc ggc tcc acg tgt cag ctg gac      1599
Ser Cys Thr Cys Pro Ser Gly Phe Ser Gly Ser Thr Cys Gln Leu Asp
            495                 500                 505 gtg gac gaa tgc gcc agc acg ccc tgc agg aat ggc gcc aaa tgc gtg      1647
Val Asp Glu Cys Ala Ser Thr Pro Cys Arg Asn Gly Ala Lys Cys Val
            510                 515                 520 gac cag ccc gat ggc tac gag tgc cgc tgt gcc gag ggc ttt gag ggc      1695
Asp Gln Pro Asp Gly Tyr Glu Cys Arg Cys Ala Glu Gly Phe Glu Gly
525                 530                 535 acg ctg tgt gat cgc aac gtg gac gac tgc tcc cct gac cca tgc cac      1743
Thr Leu Cys Asp Arg Asn Val Asp Asp Cys Ser Pro Asp Pro Cys His
540                 545                 550                 555 cat ggt cgc tgc gtg gat ggc atc gcc agc ttc tca tgt gcc tgt gct      1791
His Gly Arg Cys Val Asp Gly Ile Ala Ser Phe Ser Cys Ala Cys Ala
            560                 565                 570 cct ggc tac acg ggc aca cgc tgc gag agc cag gtg gac gaa tgc cgc      1839
Pro Gly Tyr Thr Gly Thr Arg Cys Glu Ser Gln Val Asp Glu Cys Arg
            575                 580                 585 agc cag ccc tgc cgc cat ggc ggc aaa tgc cta gac ctg gtg gac aag      1887
Ser Gln Pro Cys Arg His Gly Gly Lys Cys Leu Asp Leu Val Asp Lys
            590                 595                 600 tac ctc tgc cgc tgc cct tct ggg acc aca ggt gtg aac tgc gaa gtg      1935
Tyr Leu Cys Arg Cys Pro Ser Gly Thr Thr Gly Val Asn Cys Glu Val
605                 610                 615 aac att gac gac tgt gcc agc aac ccc tgc acc ttt gga gtc tgc cgt      1983
Asn Ile Asp Asp Cys Ala Ser Asn Pro Cys Thr Phe Gly Val Cys Arg
620                 625                 630                 635 gat ggc atc aac cgc tac gac tgt gtc tgc caa cct ggc ttc aca ggg      2031
Asp Gly Ile Asn Arg Tyr Asp Cys Val Cys Gln Pro Gly Phe Thr Gly
            640                 645                 650 ccc ctt tgt aac gtg gag atc aat gag tgt gct tcc agc cca tgc ggc      2079
```

-continued

```
            Pro Leu Cys Asn Val Glu Ile Asn Glu Cys Ala Ser Ser Pro Cys Gly
                    655                 660                 665 gag gga ggt tcc tgt gtg gat ggg gaa aat ggc ttc cgc tgc ctc tgc              2127
Glu Gly Gly Ser Cys Val Asp Gly Glu Asn Gly Phe Arg Cys Leu Cys
            670                 675                 680 ccg cct ggc tcc ttg ccc cca ctc tgc ctc ccc ccg agc cat ccc tgt              2175
Pro Pro Gly Ser Leu Pro Pro Leu Cys Leu Pro Pro Ser His Pro Cys
685                 690                 695 gcc cat gag ccc tgc agt cac ggc atc tgc tat gat gca cct ggc ggg              2223
Ala His Glu Pro Cys Ser His Gly Ile Cys Tyr Asp Ala Pro Gly Gly
700                 705                 710                 715 ttc cgc tgt gtg tgt gag cct ggc tgg agt ggc ccc cgc tgc agc cag              2271
Phe Arg Cys Val Cys Glu Pro Gly Trp Ser Gly Pro Arg Cys Ser Gln
                720                 725                 730 agc ctg gcc cga gac gcc tgt gag tcc cag ccg tgc agg gcc ggt ggg              2319
Ser Leu Ala Arg Asp Ala Cys Glu Ser Gln Pro Cys Arg Ala Gly Gly
                735                 740                 745 aca tgc agc agc gat gga atg ggt ttc cac tgc acc tgc ccg cct ggt              2367
Thr Cys Ser Ser Asp Gly Met Gly Phe His Cys Thr Cys Pro Pro Gly
            750                 755                 760 gtc cag gga cgt cag tgt gaa ctc ctc tcc ccc tgc acc ccg aac ccc              2415
Val Gln Gly Arg Gln Cys Glu Leu Leu Ser Pro Cys Thr Pro Asn Pro
765                 770                 775 tgt gag cat ggg ggc cgc tgc gag tct gcc cct ggc cag ctg cct gtc              2463
Cys Glu His Gly Gly Arg Cys Glu Ser Ala Pro Gly Gln Leu Pro Val
780                 785                 790                 795 tgc tcc tgc ccc cag ggc tgg caa gga cca cga tgc cag cag gat gtg              2511
Cys Ser Cys Pro Gln Gly Trp Gln Gly Pro Arg Cys Gln Gln Asp Val
                800                 805                 810 gac gag tgt gct ggc ccc gca ccc tgt ggc cct cat ggt atc tgc acc              2559
Asp Glu Cys Ala Gly Pro Ala Pro Cys Gly Pro His Gly Ile Cys Thr
                815                 820                 825 aac ctg gca ggg agt ttc agc tgc acc tgc cat gga ggg tac act ggc              2607
Asn Leu Ala Gly Ser Phe Ser Cys Thr Cys His Gly Gly Tyr Thr Gly
            830                 835                 840 cct tcc tgt gat cag gac atc aat gac tgt gac ccc aac cca tgc ctg              2655
Pro Ser Cys Asp Gln Asp Ile Asn Asp Cys Asp Pro Asn Pro Cys Leu
845                 850                 855 aac ggt ggc tcg tgc caa gac ggc gtg ggc tcc ttt tcc tgc tcc tgc              2703
Asn Gly Gly Ser Cys Gln Asp Gly Val Gly Ser Phe Ser Cys Ser Cys
860                 865                 870                 875 ctc cct ggt ttc gcc ggc cca cga tgc gcc cgc gat gtg gat gag tgc              2751
Leu Pro Gly Phe Ala Gly Pro Arg Cys Ala Arg Asp Val Asp Glu Cys
                880                 885                 890 ctg agc aac ccc tgc ggc ccg ggc acc tgt acc gac cac gtg gcc tcc              2799
Leu Ser Asn Pro Cys Gly Pro Gly Thr Cys Thr Asp His Val Ala Ser
            895                 900                 905 ttc acc tgc acc tgc ccg ccg ggc tac gga ggc ttc cac tgc gaa cag              2847
Phe Thr Cys Thr Cys Pro Pro Gly Tyr Gly Gly Phe His Cys Glu Gln
            910                 915                 920 gac ctg ccc gac tgc agc ccc agc tcc tgc ttc aat ggc ggg acc tgt              2895
Asp Leu Pro Asp Cys Ser Pro Ser Ser Cys Phe Asn Gly Gly Thr Cys
925                 930                 935 gtg gac ggc gtg aac tcg ttc agc tgc ctg tgc cgt ccc ggc tac aca              2943
Val Asp Gly Val Asn Ser Phe Ser Cys Leu Cys Arg Pro Gly Tyr Thr
940                 945                 950                 955 gga gcc cac tgc caa cat gag gca gac ccc tgc ctc tcg cgg ccc tgc              2991
Gly Ala His Cys Gln His Glu Ala Asp Pro Cys Leu Ser Arg Pro Cys
                960                 965                 970
```

-continued

| | | |
|---|---|---|
| cta cac ggg ggc gtc tgc agc gcc gcc cac cct ggc ttc cgc tgc acc<br>Leu His Gly Gly Val Cys Ser Ala Ala His Pro Gly Phe Arg Cys Thr<br>                975                    980                  985 | 3039 |
| tgc ctc gag agc ttc acg ggc ccg cag tgc cag acg ctg gtg gat tgg<br>Cys Leu Glu Ser Phe Thr Gly Pro Gln Cys Gln Thr Leu Val Asp Trp<br>     990                    995                  1000 | 3087 |
| tgc agc cgc cag cct tgt caa aac ggg ggt cgc tgc gtc cag act<br>Cys Ser Arg Gln Pro Cys Gln Asn Gly Gly Arg Cys Val Gln Thr<br>1005                    1010                  1015 | 3132 |
| ggg gcc tat tgc ctt tgt ccc cct gga tgg agc gga cgc ctc tgt<br>Gly Ala Tyr Cys Leu Cys Pro Pro Gly Trp Ser Gly Arg Leu Cys<br>1020                    1025                  1030 | 3177 |
| gac atc cga agc ttg ccc tgc agg gag gcc gca gcc cag atc ggg<br>Asp Ile Arg Ser Leu Pro Cys Arg Glu Ala Ala Ala Gln Ile Gly<br>1035                    1040                  1045 | 3222 |
| gtg cgg ctg gag cag ctg tgt cag gcg ggt ggg cag tgt gtg gat<br>Val Arg Leu Glu Gln Leu Cys Gln Ala Gly Gly Gln Cys Val Asp<br>1050                    1055                  1060 | 3267 |
| gaa gac agc tcc cac tac tgc gtg tgc cca gag ggc cgt act ggt<br>Glu Asp Ser Ser His Tyr Cys Val Cys Pro Glu Gly Arg Thr Gly<br>1065                    1070                  1075 | 3312 |
| agc cac tgt gag cag gag gtg gac ccc tgc ttg gcc cag ccc tgc<br>Ser His Cys Glu Gln Glu Val Asp Pro Cys Leu Ala Gln Pro Cys<br>1080                    1085                  1090 | 3357 |
| cag cat ggg ggg acc tgc cgt ggc tat atg ggg ggc tac atg tgt<br>Gln His Gly Gly Thr Cys Arg Gly Tyr Met Gly Gly Tyr Met Cys<br>1095                    1100                  1105 | 3402 |
| gag tgt ctt cct ggc tac aat ggt gat aac tgt gag gac gac gtg<br>Glu Cys Leu Pro Gly Tyr Asn Gly Asp Asn Cys Glu Asp Asp Val<br>1110                    1115                  1120 | 3447 |
| gac gag tgt gcc tcc cag ccc tgc cag cac ggg ggt tca tgc att<br>Asp Glu Cys Ala Ser Gln Pro Cys Gln His Gly Gly Ser Cys Ile<br>1125                    1130                  1135 | 3492 |
| gac ctc gtg gcc cgc tat ctc tgc tcc tgt ccc cca gga acg ctg<br>Asp Leu Val Ala Arg Tyr Leu Cys Ser Cys Pro Pro Gly Thr Leu<br>1140                    1145                  1150 | 3537 |
| ggg gtg ctc tgc gag att aat gag gat gac tgc ggc cca ggc cca<br>Gly Val Leu Cys Glu Ile Asn Glu Asp Asp Cys Gly Pro Gly Pro<br>1155                    1160                  1165 | 3582 |
| ccg ctg gac tca ggg ccc cgg tgc cta cac aat ggc acc tgc gtg<br>Pro Leu Asp Ser Gly Pro Arg Cys Leu His Asn Gly Thr Cys Val<br>1170                    1175                  1180 | 3627 |
| gac ctg gtg ggt ggt ttc cgc tgc acc tgt ccc cca gga tac act<br>Asp Leu Val Gly Gly Phe Arg Cys Thr Cys Pro Pro Gly Tyr Thr<br>1185                    1190                  1195 | 3672 |
| ggt ttg cgc tgc gag gca gac atc aat gag tgt cgc tca ggt gcc<br>Gly Leu Arg Cys Glu Ala Asp Ile Asn Glu Cys Arg Ser Gly Ala<br>1200                    1205                  1210 | 3717 |
| tgc cac gcg gca cac acc cgg gac tgc ctg cag gac cca ggc gga<br>Cys His Ala Ala His Thr Arg Asp Cys Leu Gln Asp Pro Gly Gly<br>1215                    1220                  1225 | 3762 |
| ggt ttc cgt tgc ctt tgt cat gct ggc ttc tca ggt cct cgc tgt<br>Gly Phe Arg Cys Leu Cys His Ala Gly Phe Ser Gly Pro Arg Cys<br>1230                    1235                  1240 | 3807 |
| cag act gtc ctg tct ccc tgc gag tcc cag cca tgc cag cat gga<br>Gln Thr Val Leu Ser Pro Cys Glu Ser Gln Pro Cys Gln His Gly<br>1245                    1250                  1255 | 3852 |
| ggc cag tgc cgt cct agc ccg ggt cct ggg ggt ggg ctg acc ttc<br>Gly Gln Cys Arg Pro Ser Pro Gly Pro Gly Gly Gly Leu Thr Phe<br>1260                    1265                  1270 | 3897 |

-continued

| | | |
|---|---|---|
| acc tgt cac tgt gcc cag ccg ttc tgg ggt ccg cgt tgc gag cgg<br>Thr Cys His Cys Ala Gln Pro Phe Trp Gly Pro Arg Cys Glu Arg<br>1275                        1280                        1285 | 3942 |
| gtg gcg cgc tcc tgc cgg gag ctg cag tgc ccg gtg ggc gtc cca<br>Val Ala Arg Ser Cys Arg Glu Leu Gln Cys Pro Val Gly Val Pro<br>1290                        1295                        1300 | 3987 |
| tgc cag cag acg ccc cgc ggg ccg cgc tgc gcc tgc ccc cca ggg<br>Cys Gln Gln Thr Pro Arg Gly Pro Arg Cys Ala Cys Pro Pro Gly<br>1305                        1310                        1315 | 4032 |
| ttg tcg gga ccc tcc tgc cgc agc ttc ccg ggg tcg ccg ccg ggg<br>Leu Ser Gly Pro Ser Cys Arg Ser Phe Pro Gly Ser Pro Pro Gly<br>1320                        1325                        1330 | 4077 |
| gcc agc aac gcc agc tgc gcg gcc gcc ccc tgt ctc cac ggg ggc<br>Ala Ser Asn Ala Ser Cys Ala Ala Ala Pro Cys Leu His Gly Gly<br>1335                        1340                        1345 | 4122 |
| tcc tgc cgc ccc gcg ccg ctc gcg ccc ttc ttc cgc tgc gct tgc<br>Ser Cys Arg Pro Ala Pro Leu Ala Pro Phe Phe Arg Cys Ala Cys<br>1350                        1355                        1360 | 4167 |
| gcg cag ggc tgg acc ggg ccg cgc tgc gag gcg ccc gcc gcg gca<br>Ala Gln Gly Trp Thr Gly Pro Arg Cys Glu Ala Pro Ala Ala Ala<br>1365                        1370                        1375 | 4212 |
| ccc gag gtc tcg gag gag ccg cgg tgc ccg cgc gcc gcc tgc cag<br>Pro Glu Val Ser Glu Glu Pro Arg Cys Pro Arg Ala Ala Cys Gln<br>1380                        1385                        1390 | 4257 |
| gcc aag cgc ggg gac cag cgc tgc gac cgc gag tgc aac agc cca<br>Ala Lys Arg Gly Asp Gln Arg Cys Asp Arg Glu Cys Asn Ser Pro<br>1395                        1400                        1405 | 4302 |
| ggc tgc ggc tgg gac ggc ggc gac tgc tcg ctg agc gtg ggc gac<br>Gly Cys Gly Trp Asp Gly Gly Asp Cys Ser Leu Ser Val Gly Asp<br>1410                        1415                        1420 | 4347 |
| ccc tgg cgg caa tgc gag gcg ctg cag tgc tgg cgc ctc ttc aac<br>Pro Trp Arg Gln Cys Glu Ala Leu Gln Cys Trp Arg Leu Phe Asn<br>1425                        1430                        1435 | 4392 |
| aac agc cgc tgc gac ccc gcc tgc agc tcg ccc gcc tgc ctc tac<br>Asn Ser Arg Cys Asp Pro Ala Cys Ser Ser Pro Ala Cys Leu Tyr<br>1440                        1445                        1450 | 4437 |
| gac aac ttc gac tgc cac gcc ggt ggc cgc gag cgc act tgc aac<br>Asp Asn Phe Asp Cys His Ala Gly Gly Arg Glu Arg Thr Cys Asn<br>1455                        1460                        1465 | 4482 |
| ccg gtg tac gag aag tac tgc gcc gac cac ttt gcc gac ggc cgc<br>Pro Val Tyr Glu Lys Tyr Cys Ala Asp His Phe Ala Asp Gly Arg<br>1470                        1475                        1480 | 4527 |
| tgc gac cag ggc tgc aac acg gag gag tgc ggc tgg gat ggg ctg<br>Cys Asp Gln Gly Cys Asn Thr Glu Glu Cys Gly Trp Asp Gly Leu<br>1485                        1490                        1495 | 4572 |
| gat tgt gcc agc gag gtg ccg gcc ctg ctg gcc cgc ggc gtg ctg<br>Asp Cys Ala Ser Glu Val Pro Ala Leu Leu Ala Arg Gly Val Leu<br>1500                        1505                        1510 | 4617 |
| gtg ctc aca gtg ctg ctg ccg ccg gag gag cta ctg cgt tcc agc<br>Val Leu Thr Val Leu Leu Pro Pro Glu Glu Leu Leu Arg Ser Ser<br>1515                        1520                        1525 | 4662 |
| gcc gac ttt ctg cag cgg ctc agc gcc atc ctg cgc acc tcg ctg<br>Ala Asp Phe Leu Gln Arg Leu Ser Ala Ile Leu Arg Thr Ser Leu<br>1530                        1535                        1540 | 4707 |
| cgc ttc cgc ctg gac gcg cac ggc cag gcc atg gtc ttc cct tac<br>Arg Phe Arg Leu Asp Ala His Gly Gln Ala Met Val Phe Pro Tyr<br>1545                        1550                        1555 | 4752 |
| cac cgg cct agt cct ggc tcc gaa ccc cgg gcc cgt cgg gag ctg<br>His Arg Pro Ser Pro Gly Ser Glu Pro Arg Ala Arg Arg Glu Leu | 4797 |

-continued

|  | 1560 |  |  |  | 1565 |  |  |  | 1570 |  |  |  |  |  |
|---|---|---|---|---|---|---|---|---|---|---|---|---|---|---|
| gcc | ccc | gag | gtg | atc | ggc | tcg | gta | gta | atg | ctg | gag | att | gac | aac | 4842 |
| Ala | Pro | Glu | Val | Ile | Gly | Ser | Val | Val | Met | Leu | Glu | Ile | Asp | Asn | |
|  | 1575 |  |  |  | 1580 |  |  |  | 1585 |  |  |  |  |  |
| cgg | ctc | tgc | ctg | cag | tcg | cct | gag | aat | gat | cac | tgc | ttc | ccc | gat | 4887 |
| Arg | Leu | Cys | Leu | Gln | Ser | Pro | Glu | Asn | Asp | His | Cys | Phe | Pro | Asp | |
|  | 1590 |  |  |  | 1595 |  |  |  | 1600 |  |  |  |  |  |
| gcc | cag | agc | gcc | gct | gac | tac | ctg | gga | gcg | ttg | tca | gcg | gtg | gag | 4932 |
| Ala | Gln | Ser | Ala | Ala | Asp | Tyr | Leu | Gly | Ala | Leu | Ser | Ala | Val | Glu | |
|  | 1605 |  |  |  | 1610 |  |  |  | 1615 |  |  |  |  |  |
| cgc | ctg | gac | ttc | ccg | tac | cca | ctg | cgg | gac | gtg | cgg | ggg | gag | ccg | 4977 |
| Arg | Leu | Asp | Phe | Pro | Tyr | Pro | Leu | Arg | Asp | Val | Arg | Gly | Glu | Pro | |
|  | 1620 |  |  |  | 1625 |  |  |  | 1630 |  |  |  |  |  |
| ctg | gag | cct | cca | gaa | ccc | agc | gtc | ccg | ctg | ctg | cca | ctg | cta | gtg | 5022 |
| Leu | Glu | Pro | Pro | Glu | Pro | Ser | Val | Pro | Leu | Leu | Pro | Leu | Leu | Val | |
|  | 1635 |  |  |  | 1640 |  |  |  | 1645 |  |  |  |  |  |
| gcg | ggc | gct | gtc | ttg | ctg | ctg | gtc | att | ctc | gtc | ctg | ggt | gtc | atg | 5067 |
| Ala | Gly | Ala | Val | Leu | Leu | Leu | Val | Ile | Leu | Val | Leu | Gly | Val | Met | |
|  | 1650 |  |  |  | 1655 |  |  |  | 1660 |  |  |  |  |  |
| gtg | gcc | cgg | cgc | aag | cgc | gag | cac | agc | acc | ctc | tgg | ttc | cct | gag | 5112 |
| Val | Ala | Arg | Arg | Lys | Arg | Glu | His | Ser | Thr | Leu | Trp | Phe | Pro | Glu | |
|  | 1665 |  |  |  | 1670 |  |  |  | 1675 |  |  |  |  |  |
| ggc | ttc | tca | ctg | cac | aag | gac | gtg | gcc | tct | ggt | cac | aag | ggc | cgg | 5157 |
| Gly | Phe | Ser | Leu | His | Lys | Asp | Val | Ala | Ser | Gly | His | Lys | Gly | Arg | |
|  | 1680 |  |  |  | 1685 |  |  |  | 1690 |  |  |  |  |  |
| cgg | gaa | ccc | gtg | ggc | cag | gac | gcg | ctg | ggc | atg | aag | aac | atg | gcc | 5202 |
| Arg | Glu | Pro | Val | Gly | Gln | Asp | Ala | Leu | Gly | Met | Lys | Asn | Met | Ala | |
|  | 1695 |  |  |  | 1700 |  |  |  | 1705 |  |  |  |  |  |
| aag | ggt | gag | agc | ctg | atg | ggg | gag | gtg | gcc | aca | gac | tgg | atg | gac | 5247 |
| Lys | Gly | Glu | Ser | Leu | Met | Gly | Glu | Val | Ala | Thr | Asp | Trp | Met | Asp | |
|  | 1710 |  |  |  | 1715 |  |  |  | 1720 |  |  |  |  |  |
| aca | gag | tgc | cca | gag | gcc | aag | cgg | cta | aag | gta | gag | gag | cca | ggc | 5292 |
| Thr | Glu | Cys | Pro | Glu | Ala | Lys | Arg | Leu | Lys | Val | Glu | Glu | Pro | Gly | |
|  | 1725 |  |  |  | 1730 |  |  |  | 1735 |  |  |  |  |  |
| atg | ggg | gct | gag | gag | gct | gtg | gat | tgc | cgt | cag | tgg | act | caa | cac | 5337 |
| Met | Gly | Ala | Glu | Glu | Ala | Val | Asp | Cys | Arg | Gln | Trp | Thr | Gln | His | |
|  | 1740 |  |  |  | 1745 |  |  |  | 1750 |  |  |  |  |  |
| cat | ctg | gtt | gct | gct | gac | atc | cgc | gtg | gca | cca | gcc | atg | gca | ctg | 5382 |
| His | Leu | Val | Ala | Ala | Asp | Ile | Arg | Val | Ala | Pro | Ala | Met | Ala | Leu | |
|  | 1755 |  |  |  | 1760 |  |  |  | 1765 |  |  |  |  |  |
| aca | cca | cca | cag | ggc | gac | gca | gat | gct | gat | ggc | atg | gat | gtc | aat | 5427 |
| Thr | Pro | Pro | Gln | Gly | Asp | Ala | Asp | Ala | Asp | Gly | Met | Asp | Val | Asn | |
|  | 1770 |  |  |  | 1775 |  |  |  | 1780 |  |  |  |  |  |
| gtg | cgt | ggc | cca | gat | ggc | ttc | acc | ccg | cta | atg | ctg | gct | tcc | ttc | 5472 |
| Val | Arg | Gly | Pro | Asp | Gly | Phe | Thr | Pro | Leu | Met | Leu | Ala | Ser | Phe | |
|  | 1785 |  |  |  | 1790 |  |  |  | 1795 |  |  |  |  |  |
| tgt | ggg | ggg | gct | ctg | gag | cca | atg | cca | act | gaa | gag | gat | gag | gca | 5517 |
| Cys | Gly | Gly | Ala | Leu | Glu | Pro | Met | Pro | Thr | Glu | Glu | Asp | Glu | Ala | |
|  | 1800 |  |  |  | 1805 |  |  |  | 1810 |  |  |  |  |  |
| gat | gac | aca | tca | gct | agc | atc | atc | tcc | gac | ctg | atc | tgc | cag | ggg | 5562 |
| Asp | Asp | Thr | Ser | Ala | Ser | Ile | Ile | Ser | Asp | Leu | Ile | Cys | Gln | Gly | |
|  | 1815 |  |  |  | 1820 |  |  |  | 1825 |  |  |  |  |  |
| gct | cag | ctt | ggg | gca | cgg | act | gac | cgt | act | ggc | gag | act | gct | ttg | 5607 |
| Ala | Gln | Leu | Gly | Ala | Arg | Thr | Asp | Arg | Thr | Gly | Glu | Thr | Ala | Leu | |
|  | 1830 |  |  |  | 1835 |  |  |  | 1840 |  |  |  |  |  |
| cac | ctg | gct | gcc | cgt | tat | gcc | cgt | gct | gat | gca | gcc | aag | cgg | ctg | 5652 |
| His | Leu | Ala | Ala | Arg | Tyr | Ala | Arg | Ala | Asp | Ala | Ala | Lys | Arg | Leu | |
|  | 1845 |  |  |  | 1850 |  |  |  | 1855 |  |  |  |  |  |
| ctg | gat | gct | ggg | gca | gac | acc | aat | gcc | cag | gac | cac | tca | ggc | cgc | 5697 |

| | | | | | | | | | | |
|---|---|---|---|---|---|---|---|---|---|---|
| Leu | Asp | Ala | Gly | Ala | Asp | Thr | Asn | Ala | Gln | Asp | His | Ser | Gly | Arg |
| 1860 | | | | | 1865 | | | | | 1870 | | | | |

| | | | | | | | | | | | |
|---|---|---|---|---|---|---|---|---|---|---|---|
| act | ccc | ctg | cac | aca | gct | gtc | aca | gcc | gat | gcc | cag | ggt | gtc | ttc | 5742 |
| Thr | Pro | Leu | His | Thr | Ala | Val | Thr | Ala | Asp | Ala | Gln | Gly | Val | Phe |
| 1875 | | | | | 1880 | | | | | 1885 | | | | |

| cag | att | ctc | atc | cga | aac | cgc | tct | aca | gac | ttg | gat | gcc | cgc | atg | 5787 |
|---|---|---|---|---|---|---|---|---|---|---|---|---|---|---|---|
| Gln | Ile | Leu | Ile | Arg | Asn | Arg | Ser | Thr | Asp | Leu | Asp | Ala | Arg | Met |
| 1890 | | | | | 1895 | | | | | 1900 | | | | |

| gca | gat | ggc | tca | acg | gca | ctg | atc | ctg | gcg | gcc | cgc | ctg | gca | gta | 5832 |
|---|---|---|---|---|---|---|---|---|---|---|---|---|---|---|---|
| Ala | Asp | Gly | Ser | Thr | Ala | Leu | Ile | Leu | Ala | Ala | Arg | Leu | Ala | Val |
| 1905 | | | | | 1910 | | | | | 1915 | | | | |

| gag | ggc | atg | gtg | gaa | gag | ctc | atc | gcc | agc | cat | gct | gat | gtc | aat | 5877 |
|---|---|---|---|---|---|---|---|---|---|---|---|---|---|---|---|
| Glu | Gly | Met | Val | Glu | Glu | Leu | Ile | Ala | Ser | His | Ala | Asp | Val | Asn |
| 1920 | | | | | 1925 | | | | | 1930 | | | | |

| gct | gtg | gat | gag | ctt | ggg | aaa | tca | gcc | tta | cac | tgg | gct | gcg | gct | 5922 |
|---|---|---|---|---|---|---|---|---|---|---|---|---|---|---|---|
| Ala | Val | Asp | Glu | Leu | Gly | Lys | Ser | Ala | Leu | His | Trp | Ala | Ala | Ala |
| 1935 | | | | | 1940 | | | | | 1945 | | | | |

| gtg | aac | aac | gtg | gaa | gcc | act | ttg | gcc | ctg | ctc | aaa | aat | gga | gcc | 5967 |
|---|---|---|---|---|---|---|---|---|---|---|---|---|---|---|---|
| Val | Asn | Asn | Val | Glu | Ala | Thr | Leu | Ala | Leu | Leu | Lys | Asn | Gly | Ala |
| 1950 | | | | | 1955 | | | | | 1960 | | | | |

| aat | aag | gac | atg | cag | gat | agc | aag | gag | gag | acc | ccc | cta | ttc | ctg | 6012 |
|---|---|---|---|---|---|---|---|---|---|---|---|---|---|---|---|
| Asn | Lys | Asp | Met | Gln | Asp | Ser | Lys | Glu | Glu | Thr | Pro | Leu | Phe | Leu |
| 1965 | | | | | 1970 | | | | | 1975 | | | | |

| gcc | gcc | cgc | gag | ggc | agc | tat | gag | gct | gcc | aag | ctg | ctg | ttg | gac | 6057 |
|---|---|---|---|---|---|---|---|---|---|---|---|---|---|---|---|
| Ala | Ala | Arg | Glu | Gly | Ser | Tyr | Glu | Ala | Ala | Lys | Leu | Leu | Leu | Asp |
| 1980 | | | | | 1985 | | | | | 1990 | | | | |

| cac | ttt | gcc | aac | cgt | gag | atc | acc | gac | cac | ctg | gac | agg | ctg | ccg | 6102 |
|---|---|---|---|---|---|---|---|---|---|---|---|---|---|---|---|
| His | Phe | Ala | Asn | Arg | Glu | Ile | Thr | Asp | His | Leu | Asp | Arg | Leu | Pro |
| 1995 | | | | | 2000 | | | | | 2005 | | | | |

| cgg | gac | gta | gcc | cag | gag | aga | ctg | cac | cag | gac | atc | gtg | cgc | ttg | 6147 |
|---|---|---|---|---|---|---|---|---|---|---|---|---|---|---|---|
| Arg | Asp | Val | Ala | Gln | Glu | Arg | Leu | His | Gln | Asp | Ile | Val | Arg | Leu |
| 2010 | | | | | 2015 | | | | | 2020 | | | | |

| ctg | gat | caa | ccc | agt | ggg | ccc | cgc | agc | ccc | ccc | ggt | ccc | cac | ggc | 6192 |
|---|---|---|---|---|---|---|---|---|---|---|---|---|---|---|---|
| Leu | Asp | Gln | Pro | Ser | Gly | Pro | Arg | Ser | Pro | Pro | Gly | Pro | His | Gly |
| 2025 | | | | | 2030 | | | | | 2035 | | | | |

| ctg | ggg | cct | ctg | ctc | tgt | cct | cca | ggg | gcc | ttc | ctc | cct | ggc | ctc | 6237 |
|---|---|---|---|---|---|---|---|---|---|---|---|---|---|---|---|
| Leu | Gly | Pro | Leu | Leu | Cys | Pro | Pro | Gly | Ala | Phe | Leu | Pro | Gly | Leu |
| 2040 | | | | | 2045 | | | | | 2050 | | | | |

| aaa | gcg | gca | cag | tcg | ggg | tcc | aag | aag | agc | agg | agg | ccc | ccc | ggg | 6282 |
|---|---|---|---|---|---|---|---|---|---|---|---|---|---|---|---|
| Lys | Ala | Ala | Gln | Ser | Gly | Ser | Lys | Lys | Ser | Arg | Arg | Pro | Pro | Gly |
| 2055 | | | | | 2060 | | | | | 2065 | | | | |

| aag | gcg | ggg | ctg | ggg | ccg | cag | ggg | ccc | cgg | ggg | cgg | ggc | aag | aag | 6327 |
|---|---|---|---|---|---|---|---|---|---|---|---|---|---|---|---|
| Lys | Ala | Gly | Leu | Gly | Pro | Gln | Gly | Pro | Arg | Gly | Arg | Gly | Lys | Lys |
| 2070 | | | | | 2075 | | | | | 2080 | | | | |

| ctg | acg | ctg | gcc | tgc | ccg | ggc | ccc | ctg | gct | gac | agc | tcg | gtc | acg | 6372 |
|---|---|---|---|---|---|---|---|---|---|---|---|---|---|---|---|
| Leu | Thr | Leu | Ala | Cys | Pro | Gly | Pro | Leu | Ala | Asp | Ser | Ser | Val | Thr |
| 2085 | | | | | 2090 | | | | | 2095 | | | | |

| ctg | tcg | ccc | gtg | gac | tcg | ctg | gac | tcc | ccg | cgg | cct | ttc | ggt | ggg | 6417 |
|---|---|---|---|---|---|---|---|---|---|---|---|---|---|---|---|
| Leu | Ser | Pro | Val | Asp | Ser | Leu | Asp | Ser | Pro | Arg | Pro | Phe | Gly | Gly |
| 2100 | | | | | 2105 | | | | | 2110 | | | | |

| ccc | cct | gct | tcc | cct | ggt | ggc | ttc | ccc | ctt | gag | ggg | ccc | tat | gca | 6462 |
|---|---|---|---|---|---|---|---|---|---|---|---|---|---|---|---|
| Pro | Pro | Ala | Ser | Pro | Gly | Gly | Phe | Pro | Leu | Glu | Gly | Pro | Tyr | Ala |
| 2115 | | | | | 2120 | | | | | 2125 | | | | |

| gct | gcc | act | gcc | act | gca | gtg | tct | ctg | gca | cag | ctt | ggt | ggc | cca | 6507 |
|---|---|---|---|---|---|---|---|---|---|---|---|---|---|---|---|
| Ala | Ala | Thr | Ala | Thr | Ala | Val | Ser | Leu | Ala | Gln | Leu | Gly | Gly | Pro |
| 2130 | | | | | 2135 | | | | | 2140 | | | | |

| ggc | cgg | gca | ggt | cta | ggg | cgc | cag | ccc | cct | gga | gga | tgt | gta | ctc | 6552 |
|---|---|---|---|---|---|---|---|---|---|---|---|---|---|---|---|
| Gly | Arg | Ala | Gly | Leu | Gly | Arg | Gln | Pro | Pro | Gly | Gly | Cys | Val | Leu |
| 2145 | | | | | 2150 | | | | | 2155 | | | | |

| | | | | | | | | | | | | |
|---|---|---|---|---|---|---|---|---|---|---|---|---|
| agc | ctg | ggc | ctg | ctg | aac | cct | gtg | gct | gtg | ccc | ctc | gat tgg gcc | 6597 |
| Ser | Leu | Gly | Leu | Leu | Asn | Pro | Val | Ala | Val | Pro | Leu | Asp Trp Ala |
| | 2160 | | | | 2165 | | | | 2170 | | | |
| cgg | ctg | ccc | cca | cct | gcc | cct | cca | ggc | ccc | tcg | ttc | ctg ctg cca | 6642 |
| Arg | Leu | Pro | Pro | Pro | Ala | Pro | Pro | Gly | Pro | Ser | Phe | Leu Leu Pro |
| | 2175 | | | | 2180 | | | | 2185 | | | |
| ctg | gcg | ccg | gga | ccc | cag | ctg | ctc | aac | cca | ggg | acc | ccc gtc tcc | 6687 |
| Leu | Ala | Pro | Gly | Pro | Gln | Leu | Leu | Asn | Pro | Gly | Thr | Pro Val Ser |
| | 2190 | | | | 2195 | | | | 2200 | | | |
| ccg | cag | gag | cgg | ccc | ccg | cct | tac | ctg | gca | gtc | cca | gga cat ggc | 6732 |
| Pro | Gln | Glu | Arg | Pro | Pro | Pro | Tyr | Leu | Ala | Val | Pro | Gly His Gly |
| | 2205 | | | | 2210 | | | | 2215 | | | |
| gag | gag | tac | ccg | gtg | gct | ggg | gca | cac | agc | agc | ccc | cca aag gcc | 6777 |
| Glu | Glu | Tyr | Pro | Val | Ala | Gly | Ala | His | Ser | Ser | Pro | Pro Lys Ala |
| | 2220 | | | | 2225 | | | | 2230 | | | |
| cgc | ttc | ctg | cgg | gtt | ccc | agt | gag | cac | cct | tac | ctg | acc cca tcc | 6822 |
| Arg | Phe | Leu | Arg | Val | Pro | Ser | Glu | His | Pro | Tyr | Leu | Thr Pro Ser |
| | 2235 | | | | 2240 | | | | 2245 | | | |
| ccc | gaa | tcc | cct | gag | cac | tgg | gcc | agc | cct | tca | cct | ccc tcc ctc | 6867 |
| Pro | Glu | Ser | Pro | Glu | His | Trp | Ala | Ser | Pro | Ser | Pro | Pro Ser Leu |
| | 2250 | | | | 2255 | | | | 2260 | | | |
| tca | gac | tgg | tcc | gaa | tcc | acg | cct | agc | cca | gcc | act | gcc act ggg | 6912 |
| Ser | Asp | Trp | Ser | Glu | Ser | Thr | Pro | Ser | Pro | Ala | Thr | Ala Thr Gly |
| | 2265 | | | | 2270 | | | | 2275 | | | |
| gcc | atg | gcc | acc | acc | act | ggg | gca | ctg | cct | gcc | cag | cca ctt ccc | 6957 |
| Ala | Met | Ala | Thr | Thr | Thr | Gly | Ala | Leu | Pro | Ala | Gln | Pro Leu Pro |
| | 2280 | | | | 2285 | | | | 2290 | | | |
| ttg | tct | gtt | ccc | agc | tcc | ctt | gct | cag | gcc | cag | acc | cag ctg ggg | 7002 |
| Leu | Ser | Val | Pro | Ser | Ser | Leu | Ala | Gln | Ala | Gln | Thr | Gln Leu Gly |
| | 2295 | | | | 2300 | | | | 2305 | | | |
| ccc | cag | ccg | gaa | gtt | acc | ccc | aag | agg | caa | gtg | ttg | gcc tga | 7044 |
| Pro | Gln | Pro | Glu | Val | Thr | Pro | Lys | Arg | Gln | Val | Leu | Ala |
| | 2310 | | | | 2315 | | | | 2320 | | | |

```
gacgctcgtc agttcttaga tcttgggggc ctaaagagac ccccgtcctg cctcctttct      7104
ttctctgtct cttccttcct tttagtcttt ttcatcctct tctctttcca ccaaccctcc      7164
tgcatccttg ccttgcagcg tgaccgagat aggtcatcag cccagggctt cagtcttcct      7224
ttatttataa tgggtggggg ctaccaccca ccctctcagt cttgtgaaga gtctgggacc      7284
tccttcttcc ccacttctct cttccctcat tcctttctct ctccttctgg cctctcattt      7344
ccttacactc tgacatgaat gaattattat tattttttctt tttctttttt tttttacatt      7404
ttgtatagaa acaaattcat ttaaacaaac ttattattat tattttttac aaaatatata      7464
tatggagatg ctccctcccc ctgtgaaccc cccagtgccc ccgtggggct gagtctgtgg      7524
gcccattcgg ccaagctgga ttctgtgtac ctagtacaca ggcatgactg ggatcccgtg      7584
taccgagtac acgacccagg tatgtaccaa gtaggcaccc ttgggcgcac ccactggggc      7644
cagggggtcgg gggagtgttg ggagcctcct ccccacccca cctccctcac ttcactgcat      7704
tccagattgg acatgttcca tagccttgct ggggaagggc ccactgccaa ctccctctgc      7764
cccagcccca cccttggcca tctcccttg ggaactaggg ggctgctggt gggaaatggg      7824
agccagggca gatgtatgca ttcctttatg tccctgtaaa tgtgggacta caagaagagg      7884
agctgcctga gtggtacttt ctcttcctgg taatcctctg gcccagcctt atggcagaat      7944
agaggtattt ttaggctatt tttgtaatat ggcttctggt caaaatccct gtgtagctga      8004
attcccaagc cctgcattgt acagccccccc actcccctca ccacctaata aaggaatagt      8064
taacactcaa aaaaaaaaaa aaaaaaa                                          8091
```

<210> SEQ ID NO 2
<211> LENGTH: 2321
<212> TYPE: PRT
<213> ORGANISM: Homo sapiens

<400> SEQUENCE: 2

```
Met Gly Pro Gly Ala Arg Gly Arg Arg Arg Arg Pro Met Ser
1               5                   10                  15

Pro Pro Pro Pro Pro Pro Val Arg Ala Leu Pro Leu Leu Leu Leu
            20                  25                  30

Leu Ala Gly Pro Gly Ala Ala Pro Pro Cys Leu Asp Gly Ser Pro
            35                  40                  45

Cys Ala Asn Gly Gly Arg Cys Thr Gln Leu Pro Ser Arg Glu Ala Ala
        50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                        85                  90                  95

Val Val Ala Gly Thr Ala Arg Phe Ser Cys Arg Cys Pro Arg Gly Phe
                100                 105                 110

Arg Gly Pro Asp Cys Ser Leu Pro Asp Pro Cys Leu Ser Ser Pro Cys
            115                 120                 125

Ala His Gly Ala Arg Cys Ser Val Gly Pro Asp Gly Arg Phe Leu Cys
        130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                    165                 170                 175

Thr Pro Gly Ser Phe Arg Cys Gln Cys Pro Ala Gly Tyr Thr Gly Pro
                180                 185                 190

Leu Cys Glu Asn Pro Ala Val Pro Cys Ala Pro Ser Pro Cys Arg Asn
            195                 200                 205

Gly Gly Thr Cys Arg Gln Ser Gly Asp Leu Thr Tyr Asp Cys Ala Cys
        210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                    245                 250                 255

Thr Tyr Asn Cys Gln Cys Pro Pro Glu Trp Thr Gly Gln Phe Cys Thr
                260                 265                 270

Glu Asp Val Asp Glu Cys Gln Leu Gln Pro Asn Ala Cys His Asn Gly
            275                 280                 285

Gly Thr Cys Phe Asn Thr Leu Gly Gly His Ser Cys Val Cys Val Asn
        290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
                    325                 330                 335

Tyr Cys Ala Cys Pro Met Gly Lys Thr Gly Leu Leu Cys His Leu Asp
                340                 345                 350

Asp Ala Cys Val Ser Asn Pro Cys His Glu Asp Ala Ile Cys Asp Thr
            355                 360                 365

Asn Pro Val Asn Gly Arg Ala Ile Cys Thr Cys Pro Pro Gly Phe Thr
```

```
            370                 375                 380
Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
                405                 410                 415

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
        435                 440                 445

Arg Ile Gly Gln Phe Thr Cys Ile Cys Met Ala Gly Phe Thr Gly Thr
450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
                485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
        515                 520                 525

Tyr Glu Cys Arg Cys Ala Glu Gly Phe Glu Gly Thr Leu Cys Asp Arg
530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
        595                 600                 605

Pro Ser Gly Thr Thr Gly Val Asn Cys Glu Val Asn Ile Asp Asp Cys
610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655

Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
        675                 680                 685

Pro Pro Leu Cys Leu Pro Pro Ser His Pro Cys Ala His Glu Pro Cys
690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
        755                 760                 765

Cys Glu Leu Leu Ser Pro Cys Thr Pro Asn Pro Cys Glu His Gly Gly
770                 775                 780

Arg Cys Glu Ser Ala Pro Gly Gln Leu Pro Val Cys Ser Cys Pro Gln
785                 790                 795                 800
```

-continued

```
Gly Trp Gln Gly Pro Arg Cys Gln Gln Asp Val Asp Glu Cys Ala Gly
            805                 810                 815
Pro Ala Pro Cys Gly Pro His Gly Ile Cys Thr Asn Leu Ala Gly Ser
            820                 825                 830
Phe Ser Cys Thr Cys His Gly Gly Tyr Thr Gly Pro Ser Cys Asp Gln
            835                 840                 845
Asp Ile Asn Asp Cys Asp Pro Asn Pro Cys Leu Asn Gly Gly Ser Cys
            850                 855                 860
Gln Asp Gly Val Gly Ser Phe Ser Cys Ser Cys Leu Pro Gly Phe Ala
865                 870                 875                 880
Gly Pro Arg Cys Ala Arg Asp Val Asp Glu Cys Leu Ser Asn Pro Cys
            885                 890                 895
Gly Pro Gly Thr Cys Thr Asp His Val Ala Ser Phe Thr Cys Thr Cys
            900                 905                 910
Pro Pro Gly Tyr Gly Gly Phe His Cys Glu Gln Asp Leu Pro Asp Cys
            915                 920                 925
Ser Pro Ser Ser Cys Phe Asn Gly Gly Thr Cys Val Asp Gly Val Asn
            930                 935                 940
Ser Phe Ser Cys Leu Cys Arg Pro Gly Tyr Thr Gly Ala His Cys Gln
945                 950                 955                 960
His Glu Ala Asp Pro Cys Leu Ser Arg Pro Cys Leu His Gly Gly Val
            965                 970                 975
Cys Ser Ala Ala His Pro Gly Phe Arg Cys Thr Cys Leu Glu Ser Phe
            980                 985                 990
Thr Gly Pro Gln Cys Gln Thr Leu Val Asp Trp Cys Ser Arg Gln Pro
            995                 1000                1005
Cys Gln Asn Gly Gly Arg Cys Val Gln Thr Gly Ala Tyr Cys Leu
        1010                1015                1020
Cys Pro Pro Gly Trp Ser Gly Arg Leu Cys Asp Ile Arg Ser Leu
        1025                1030                1035
Pro Cys Arg Glu Ala Ala Ala Gln Ile Gly Val Arg Leu Glu Gln
        1040                1045                1050
Leu Cys Gln Ala Gly Gly Gln Cys Val Asp Glu Asp Ser Ser His
        1055                1060                1065
Tyr Cys Val Cys Pro Glu Gly Arg Thr Gly Ser His Cys Glu Gln
        1070                1075                1080
Glu Val Asp Pro Cys Leu Ala Gln Pro Cys Gln His Gly Gly Thr
        1085                1090                1095
Cys Arg Gly Tyr Met Gly Gly Tyr Met Cys Glu Cys Leu Pro Gly
        1100                1105                1110
Tyr Asn Gly Asp Asn Cys Glu Asp Asp Val Asp Glu Cys Ala Ser
        1115                1120                1125
Gln Pro Cys Gln His Gly Gly Ser Cys Ile Asp Leu Val Ala Arg
        1130                1135                1140
Tyr Leu Cys Ser Cys Pro Pro Gly Thr Leu Gly Val Leu Cys Glu
        1145                1150                1155
Ile Asn Glu Asp Asp Cys Gly Pro Gly Pro Pro Leu Asp Ser Gly
        1160                1165                1170
Pro Arg Cys Leu His Asn Gly Thr Cys Val Asp Leu Val Gly Gly
        1175                1180                1185
Phe Arg Cys Thr Cys Pro Pro Gly Tyr Thr Gly Leu Arg Cys Glu
        1190                1195                1200
```

-continued

Ala Asp Ile Asn Glu Cys Arg Ser Gly Ala Cys His Ala Ala His
1205                1210                1215

Thr Arg Asp Cys Leu Gln Asp Pro Gly Gly Phe Arg Cys Leu
1220                1225                1230

Cys His Ala Gly Phe Ser Gly Pro Arg Cys Gln Thr Val Leu Ser
1235                1240                1245

Pro Cys Glu Ser Gln Pro Cys Gln His Gly Gly Gln Cys Arg Pro
1250                1255                1260

Ser Pro Gly Pro Gly Gly Gly Leu Thr Phe Thr Cys His Cys Ala
1265                1270                1275

Gln Pro Phe Trp Gly Pro Arg Cys Glu Arg Val Ala Arg Ser Cys
1280                1285                1290

Arg Glu Leu Gln Cys Pro Val Gly Val Pro Cys Gln Gln Thr Pro
1295                1300                1305

Arg Gly Pro Arg Cys Ala Cys Pro Pro Gly Leu Ser Gly Pro Ser
1310                1315                1320

Cys Arg Ser Phe Pro Gly Ser Pro Pro Gly Ala Ser Asn Ala Ser
1325                1330                1335

Cys Ala Ala Ala Pro Cys Leu His Gly Gly Ser Cys Arg Pro Ala
1340                1345                1350

Pro Leu Ala Pro Phe Phe Arg Cys Ala Cys Ala Gln Gly Trp Thr
1355                1360                1365

Gly Pro Arg Cys Glu Ala Pro Ala Ala Ala Pro Glu Val Ser Glu
1370                1375                1380

Glu Pro Arg Cys Pro Arg Ala Ala Cys Gln Ala Lys Arg Gly Asp
1385                1390                1395

Gln Arg Cys Asp Arg Glu Cys Asn Ser Pro Gly Cys Gly Trp Asp
1400                1405                1410

Gly Gly Asp Cys Ser Leu Ser Val Gly Asp Pro Trp Arg Gln Cys
1415                1420                1425

Glu Ala Leu Gln Cys Trp Arg Leu Phe Asn Asn Ser Arg Cys Asp
1430                1435                1440

Pro Ala Cys Ser Ser Pro Ala Cys Leu Tyr Asp Asn Phe Asp Cys
1445                1450                1455

His Ala Gly Gly Arg Glu Arg Thr Cys Asn Pro Val Tyr Glu Lys
1460                1465                1470

Tyr Cys Ala Asp His Phe Ala Asp Gly Arg Cys Asp Gln Gly Cys
1475                1480                1485

Asn Thr Glu Glu Cys Gly Trp Asp Gly Leu Asp Cys Ala Ser Glu
1490                1495                1500

Val Pro Ala Leu Leu Ala Arg Gly Val Leu Val Leu Thr Val Leu
1505                1510                1515

Leu Pro Pro Glu Glu Leu Leu Arg Ser Ser Ala Asp Phe Leu Gln
1520                1525                1530

Arg Leu Ser Ala Ile Leu Arg Thr Ser Leu Arg Phe Arg Leu Asp
1535                1540                1545

Ala His Gly Gln Ala Met Val Phe Pro Tyr His Arg Pro Ser Pro
1550                1555                1560

Gly Ser Glu Pro Arg Ala Arg Arg Glu Leu Ala Pro Glu Val Ile
1565                1570                1575

Gly Ser Val Val Met Leu Glu Ile Asp Asn Arg Leu Cys Leu Gln
1580                1585                1590

Ser Pro Glu Asn Asp His Cys Phe Pro Asp Ala Gln Ser Ala Ala

-continued

```
             1595                1600                1605

Asp  Tyr  Leu  Gly  Ala  Leu  Ser  Ala  Val  Glu  Arg  Leu  Asp  Phe  Pro
     1610                1615                1620

Tyr  Pro  Leu  Arg  Asp  Val  Arg  Gly  Glu  Pro  Leu  Glu  Pro  Pro  Glu
     1625                1630                1635

Pro  Ser  Val  Pro  Leu  Leu  Pro  Leu  Leu  Val  Ala  Gly  Ala  Val  Leu
     1640                1645                1650

Leu  Leu  Val  Ile  Leu  Val  Leu  Gly  Val  Met  Val  Ala  Arg  Arg  Lys
     1655                1660                1665

Arg  Glu  His  Ser  Thr  Leu  Trp  Phe  Pro  Glu  Gly  Phe  Ser  Leu  His
     1670                1675                1680

Lys  Asp  Val  Ala  Ser  Gly  His  Lys  Gly  Arg  Arg  Glu  Pro  Val  Gly
     1685                1690                1695

Gln  Asp  Ala  Leu  Gly  Met  Lys  Asn  Met  Ala  Lys  Gly  Glu  Ser  Leu
     1700                1705                1710

Met  Gly  Glu  Val  Ala  Thr  Asp  Trp  Met  Asp  Thr  Glu  Cys  Pro  Glu
     1715                1720                1725

Ala  Lys  Arg  Leu  Lys  Val  Glu  Glu  Pro  Gly  Met  Gly  Ala  Glu  Glu
     1730                1735                1740

Ala  Val  Asp  Cys  Arg  Gln  Trp  Thr  Gln  His  His  Leu  Val  Ala  Ala
     1745                1750                1755

Asp  Ile  Arg  Val  Ala  Pro  Ala  Met  Ala  Leu  Thr  Pro  Pro  Gln  Gly
     1760                1765                1770

Asp  Ala  Asp  Ala  Asp  Gly  Met  Asp  Val  Asn  Val  Arg  Gly  Pro  Asp
     1775                1780                1785

Gly  Phe  Thr  Pro  Leu  Met  Leu  Ala  Ser  Phe  Cys  Gly  Gly  Ala  Leu
     1790                1795                1800

Glu  Pro  Met  Pro  Thr  Glu  Glu  Asp  Glu  Ala  Asp  Asp  Thr  Ser  Ala
     1805                1810                1815

Ser  Ile  Ile  Ser  Asp  Leu  Ile  Cys  Gln  Gly  Ala  Gln  Leu  Gly  Ala
     1820                1825                1830

Arg  Thr  Asp  Arg  Thr  Gly  Glu  Thr  Ala  Leu  His  Leu  Ala  Ala  Arg
     1835                1840                1845

Tyr  Ala  Arg  Ala  Asp  Ala  Ala  Lys  Arg  Leu  Leu  Asp  Ala  Gly  Ala
     1850                1855                1860

Asp  Thr  Asn  Ala  Gln  Asp  His  Ser  Gly  Arg  Thr  Pro  Leu  His  Thr
     1865                1870                1875

Ala  Val  Thr  Ala  Asp  Ala  Gln  Gly  Val  Phe  Gln  Ile  Leu  Ile  Arg
     1880                1885                1890

Asn  Arg  Ser  Thr  Asp  Leu  Asp  Ala  Arg  Met  Ala  Asp  Gly  Ser  Thr
     1895                1900                1905

Ala  Leu  Ile  Leu  Ala  Ala  Arg  Leu  Ala  Val  Glu  Gly  Met  Val  Glu
     1910                1915                1920

Glu  Leu  Ile  Ala  Ser  His  Ala  Asp  Val  Asn  Ala  Val  Asp  Glu  Leu
     1925                1930                1935

Gly  Lys  Ser  Ala  Leu  His  Trp  Ala  Ala  Ala  Val  Asn  Asn  Val  Glu
     1940                1945                1950

Ala  Thr  Leu  Ala  Leu  Leu  Lys  Asn  Gly  Ala  Asn  Lys  Asp  Met  Gln
     1955                1960                1965

Asp  Ser  Lys  Glu  Glu  Thr  Pro  Leu  Phe  Leu  Ala  Ala  Arg  Glu  Gly
     1970                1975                1980

Ser  Tyr  Glu  Ala  Ala  Lys  Leu  Leu  Leu  Asp  His  Phe  Ala  Asn  Arg
     1985                1990                1995
```

-continued

Glu Ile Thr Asp His Leu Asp Arg Leu Pro Arg Asp Val Ala Gln
2000                2005                 2010

Glu Arg Leu His Gln Asp Ile Val Arg Leu Leu Asp Gln Pro Ser
    2015                2020                2025

Gly Pro Arg Ser Pro Pro Gly Pro His Gly Leu Gly Pro Leu Leu
2030                2035                 2040

Cys Pro Pro Gly Ala Phe Leu Pro Gly Leu Lys Ala Ala Gln Ser
    2045                2050                2055

Gly Ser Lys Lys Ser Arg Arg Pro Pro Gly Lys Ala Gly Leu Gly
2060                2065                 2070

Pro Gln Gly Pro Arg Gly Arg Gly Lys Lys Leu Thr Leu Ala Cys
    2075                2080                2085

Pro Gly Pro Leu Ala Asp Ser Ser Val Thr Leu Ser Pro Val Asp
2090                2095                 2100

Ser Leu Asp Ser Pro Arg Pro Phe Gly Gly Pro Pro Ala Ser Pro
    2105                2110                2115

Gly Gly Phe Pro Leu Glu Gly Pro Tyr Ala Ala Ala Thr Ala Thr
2120                2125                 2130

Ala Val Ser Leu Ala Gln Leu Gly Gly Pro Gly Arg Ala Gly Leu
    2135                2140                2145

Gly Arg Gln Pro Pro Gly Gly Cys Val Leu Ser Leu Gly Leu Leu
2150                2155                 2160

Asn Pro Val Ala Val Pro Leu Asp Trp Ala Arg Leu Pro Pro Pro
    2165                2170                2175

Ala Pro Pro Gly Pro Ser Phe Leu Leu Pro Leu Ala Pro Gly Pro
2180                2185                 2190

Gln Leu Leu Asn Pro Gly Thr Pro Val Ser Pro Gln Glu Arg Pro
    2195                2200                2205

Pro Pro Tyr Leu Ala Val Pro Gly His Gly Glu Glu Tyr Pro Val
2210                2215                 2220

Ala Gly Ala His Ser Ser Pro Pro Lys Ala Arg Phe Leu Arg Val
    2225                2230                2235

Pro Ser Glu His Pro Tyr Leu Thr Pro Ser Pro Glu Ser Pro Glu
2240                2245                 2250

His Trp Ala Ser Pro Ser Pro Pro Ser Leu Ser Asp Trp Ser Glu
    2255                2260                2265

Ser Thr Pro Ser Pro Ala Thr Ala Thr Gly Ala Met Ala Thr Thr
2270                2275                 2280

Thr Gly Ala Leu Pro Ala Gln Pro Leu Pro Leu Ser Val Pro Ser
    2285                2290                2295

Ser Leu Ala Gln Ala Gln Thr Gln Leu Gly Pro Gln Pro Glu Val
2300                2305                 2310

Thr Pro Lys Arg Gln Val Leu Ala
    2315                2320

<210> SEQ ID NO 3
<211> LENGTH: 9
<212> TYPE: PRT
<213> ORGANISM: Artificial
<220> FEATURE:
<223> OTHER INFORMATION: Synthetic peptide

<400> SEQUENCE: 3

Cys Phe Asn Thr Leu Gly Gly His Ser
1               5

```
<210> SEQ ID NO 4
<211> LENGTH: 11
<212> TYPE: PRT
<213> ORGANISM: Artificial
<220> FEATURE:
<223> OTHER INFORMATION: Synthetic peptide

<400> SEQUENCE: 4

Cys Val Cys Val Asn Gly Trp Thr Gly Glu Ser
1               5                   10

<210> SEQ ID NO 5
<211> LENGTH: 5
<212> TYPE: PRT
<213> ORGANISM: Artificial
<220> FEATURE:
<223> OTHER INFORMATION: Synthetic peptide

<400> SEQUENCE: 5

Cys Ala Thr Ala Val
1               5

<210> SEQ ID NO 6
<211> LENGTH: 6
<212> TYPE: PRT
<213> ORGANISM: Artificial
<220> FEATURE:
<223> OTHER INFORMATION: Synthetic peptide

<400> SEQUENCE: 6

Cys Phe His Gly Ala Thr
1               5

<210> SEQ ID NO 7
<211> LENGTH: 5
<212> TYPE: PRT
<213> ORGANISM: Artificial
<220> FEATURE:
<223> OTHER INFORMATION: Synthetic peptide

<400> SEQUENCE: 7

Cys Val Ser Asn Pro
1               5

<210> SEQ ID NO 8
<211> LENGTH: 6
<212> TYPE: PRT
<213> ORGANISM: Artificial
<220> FEATURE:
<223> OTHER INFORMATION: Synthetic peptide

<400> SEQUENCE: 8

Cys Leu Asn Gly Gly Ser
1               5

<210> SEQ ID NO 9
<211> LENGTH: 38
<212> TYPE: PRT
<213> ORGANISM: Artificial
<220> FEATURE:
<223> OTHER INFORMATION: Synthetic peptide

<400> SEQUENCE: 9

Cys Phe Asn Thr Leu Gly Gly His Ser Cys Val Cys Val Asn Gly Trp
1               5                   10                  15
```

```
-continued

Thr Gly Glu Ser Cys Ser Gln Asn Ile Asp Asp Cys Ala Thr Ala Val
            20                  25                  30

Cys Phe His Gly Ala Thr
            35

<210> SEQ ID NO 10
<211> LENGTH: 38
<212> TYPE: PRT
<213> ORGANISM: Artificial
<220> FEATURE:
<223> OTHER INFORMATION: Synthetic peptide

<400> SEQUENCE: 10

Cys Thr Asn Leu Ala Gly Ser Phe Ser Cys Thr Cys His Gly Gly Tyr
1               5                   10                  15

Thr Gly Pro Ser Cys Asp Gln Asp Ile Asn Asp Cys Asp Pro Asn Pro
            20                  25                  30

Cys Leu Asn Gly Gly Ser
            35
```